US008025865B2

(12) United States Patent
Pastorekova et al.

(10) Patent No.: US 8,025,865 B2
(45) Date of Patent: Sep. 27, 2011

(54) CA IX-SPECIFIC INHIBITORS

(75) Inventors: Silvia Pastorekova, Bratislava (SK); Jaromir Pastorek, Bratislava (SK)

(73) Assignee: Institute of Virology of the Slovak Academy of Sciences, Bratislava (SK)

( * ) Notice: Subject to any disclaimer, the term of this patent is extended or adjusted under 35 U.S.C. 154(b) by 548 days.

(21) Appl. No.: 11/929,652

(22) Filed: Oct. 30, 2007

(65) Prior Publication Data

US 2008/0213180 A1 Sep. 4, 2008

Related U.S. Application Data

(63) Continuation of application No. 11/222,986, filed on Sep. 8, 2005, now Pat. No. 7,833,734, which is a continuation-in-part of application No. 10/723,795, filed on Nov. 26, 2003, now Pat. No. 7,550,424.

(60) Provisional application No. 60/609,103, filed on Sep. 9, 2004, provisional application No. 60/429,089, filed on Nov. 26, 2002, provisional application No. 60/489,473, filed on Jul. 22, 2003, provisional application No. 60/515,104, filed on Oct. 28, 2003.

(51) Int. Cl.
*A61K 51/10* (2006.01)

(52) U.S. Cl. ..................... 424/1.49

(58) Field of Classification Search .................. 424/1.49
See application file for complete search history.

(56) References Cited

U.S. PATENT DOCUMENTS

| 6,027,887 | A | * | 2/2000 | Zavada et al. .............. 435/6 |
| 6,034,099 | A | | 3/2000 | Pamukcu et al. ........... 514/330 |

OTHER PUBLICATIONS

Sigma® Product Information for Fluoresceine Isothiocynate (Dec. 2000).*
Casey et al., "Carbonic Anhydrase Inhibitors. Design of Selective, Membrane-Impermeant Inhibitors Targeting the Human Tumor-Associated Isozyme IX," *J. Med Chem.*, 47: 2337-2347 (2004).
Gerweck, L.E., "Tumor pH: Implications for Treatment and Novel Drug Design," *Seminars in Radiation Oncology*, 8(3): 176-182 (Jul. 1998).
Casini et al., "Carbonic Anhydrase Inhibitors: Water-Soluble 4-Sulfamoylphenylthioureas as Topical Intraocular Pressure-Lowering Agents with Long-Lasting Effects," *J. Med. Chem.*, 43: 4884-4892 (2000).
Chegwidden et al., "The Roles of Carbonic Anhydrase Isozymes in Cancer," *Gene Families: Studies of DNA, RNA, Enzymes and Proteins*. Proceedings of the International Isozymes, 10th, Beijing, China, Oct. 5-10, 1999, Meeting Date 1999, 157-169 (Xue, G. ed.; World Scientific Pub. Co.; 2001).
Clare and Supuran, "Carbonic anhydrase inhibitors. Part 61. Quantum chemical QSAR of a group of benzenedisulfonamides." *Eur. J. Med. Chem.*, 34: 463-474 (1999).

Cuthbert et al., "Bicarbonate-dependent chloride secretion in Calu-3 epithelia In response to 7,8-benzoquinoline," *J Physiol.*, 551(Pt 1): 79-92 (Aug. 15, 2003).
Franchi et al., "Carbonic Anhydrase Inhibitors. Inhibition of Cytosolic Isozymes I and II and Transmembrane, Cancer-associated Isozyme IX with Lipophillic Sulfonamides," *Journal of Enzyme Inhbition and Medicinal Chemistry*, 18(4): 333-338 (Aug. 2003).
Ilies et al., "Carbonic Anhydrase Inhibitors. Inhibition of Tumor-Associated Isozyme IX by Halogenosulfanilamide and Halogenophenylaminobenzolamide Derivatives," *J. Med. Chem.*, 46: 2187-2196 (2003).
Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).
Scozzafava and Supuran, "Carbonic Anhydrase Inhibitors: Synthesis of *N*-Morpholythiocarbonylsulfenylamino Aromatic/Heterocyclic Sulfonamides and their Interaction with Isozymes I, II and IV," *Bioorganic & Medicinal Chemistry Letters*, 10: 1117-1120 (2000).
Scozzafava et al., "Carbonic Anhydrase Inhibitors. Synthesis of Water-Soluble, Topically Effective, Intraocular Pressure-Lowering Aromatic/Heterocyclic Sulfonamides Containing Cationic or Anionic Moieties: Is the Tail More Important than the Ring?" *J. Med. Chem.*, 42: 2641-2650 (1999).
Scozzafava et al., "Carbonic Anhydrase Inhibitors: Synthesis of Membrane-Impermeant Low Molecular Weight Sulfonamides Possessing In Vivo Selectivity for the Membrane-Bound versus Cytosolic Isozymes," *J. Med. Chem.*, 43: 292-300 (Jan. 27, 2000).
Sterling et al., "The functional and physical relationship between the DRA bicarbonate transporter and carbonic anhydrase II," *Am. J. Physiol. Cell Physiol.*, 283(5): C1522-C1529 (Nov. 2002).
Supuran and Clare, "Carbonic anhydrase inhibitors. Part 24. A quantitative structure-activity relationship study of positively charged sulfonamide inhibitors," *Eur. J. Med. Chem.*, 30: 687-696 (1995).
Supuran and Clare, "Carbonic anhydrase inhibitors—Part 57: Quantum chemical QSAR of a group of 1,3,4-thiadiazole-and 1,3,4-thiadiazoline disulfonamides with carbonic anhydrase inhibitory properties," *Eur. J. Med. Chem.*, 34: 41-50 (1999).
Supuran and Scozzafava, "Carbonic Anhydrase Inhibitors: Aromatic Sulfonamides and Disulfonamides Act as Efficient Tumor Growth Inhbitors," *J. Enzyme Inhib.*, 15(6): 597-610 (2000).

(Continued)

*Primary Examiner* — Misook Yu
*Assistant Examiner* — Brad Duffy
(74) *Attorney, Agent, or Firm* — Leona L. Lauder; Joan C. Harland; Barbara A. Shimei

(57) ABSTRACT

Therapeutic methods for inhibiting the growth of preneoplastic/neoplastic vertebrate cells that abnormally express MN protein are disclosed. Screening assays are provided for identifying compounds, preferably organic compounds, preferably aromatic and heterocylic sulfonamides, which inhibit the enzymatic activity of MN/CA IX and that are useful for treating patients with preneoplastic/neoplastic disease. Further, the CA IX-specific inhibitors when labeled can also be used diagnostically/prognostically for preneoplastic/neoplastic disease, and for imaging use, for example, to detect hypoxic precancerous cells, tumors and/or metastases, by selectively binding to activated CA IX, preferably CA IX activated under hypoxic conditions, and not to inactive CA IX. Such detection of hypoxic conditions can be helpful in determining effective treatment options, and in predicting treatment outcome and the prognosis of disease development.

13 Claims, 19 Drawing Sheets

OTHER PUBLICATIONS

Supuran and Scozzafava, "Carbonic anhydrase inhibitors—Part 94. 1,3,4-Thiadiazole-2-sulfonamide derivatives as antitumor agents?," *Eur. J. Med. Chem.*, 35(9):867-874 (Sep. 2000).

Supuran et al., "Carbonic anhydrase inhibitors—Part 53. Synthesis of substituted-pyridinium derivatives of aromatic sulfonamides: The first non-polymeric membrane-impermeable inhibitors with selectivity for isozyme IV," *Eur. J. Med. Chem.*, 33:577-594 (1998).

Supuran et al., "Carbonic anhydrase inhibitors—Part 29: Interaction of isozymes I, II, and IV with benzolamide-like derivatives." *Eur. J. Med. Chem.*, 33: 739-751 (1998).

Supuran et al., "Carbonic Anhydrase Inhibitors: Synthesis of Sulfonamides Incorporating 2,4,6-Trisubstituted-Pyridinium-Ethylcarboxamido Moieties Possessing Membrane-Impermeability and In Vivo Selectivity for the Membrane-Bound (CA IV) Versus the Cytosolic (CA I and CA II) Isozymes," *J. Enzyme Inhibition*, 15(4): 381-401 (2000).

Supuran et al., "Carbonic Anhydrase Inhibitors: Sulfonamides as Antitumor Agents?," *Bioorganic & Medicinal Chemistry*, 9(3): 703-714 (Mar. 2001).

Supuran et al., "Carbonic Anhydrase Inhibitors," *Medicinal Research Reviews*, 23(2): 146-189 (Mar. 2003).

Teicher et al., "A Carbonic Anhydrase Inhibitor as a Potential Modulator of Cancer Therapies," *Anticancer Research*, 13: 1549-1556 (1993).

Vullo et al., "Carbonic Anhydrase Inhibitors. Inhibition of Cytosolic Isozymes I and II and Transmembrane, Cancer-associated Isozyme IX with Anions," *Journal of Enzyme Inhibition and Medicinal Chemistry*, 18(5): 403-406 (Oct. 2003).

Vullo et al., "Carbonic Anhydrase Inhibitors: Inhibition of the Tumor-Associated Isozyme IX with Aromatic and Heterocyclic Sulfonamides," *Bioorganic Medicinal Chemistry Letters*, 13(6): 1005-1009 (Mar. 24, 2003).

Wingo et al., "The Catalytic Properties of Human Carbonic Anhydrase IX," *Biochemical and Biophysical Research Communications*, 288: 666-669 (2001).

Winum et al., "Carbonic Anhydrase Inhibitors. Inhibition of Cytosolic Isozymes I and II and Transmembrane, Tumor-Associated Isozyme IX with Sulfamates Including EMATE Also Acting as Steroid Sulfatase Inhibitors," *J. Med. Chem.*, 46(11): 2197-2204 (May 22, 2003).

Wistrand and Lindqvist, "Design of Carbonic Anhydrase Inhibitors and the Relationship Between the Pharmacodynamics and Pharmacokinetics of Actazolamide," *In Carbonic Anhydrase—From Biochemistry and Genetics to Physiology and Clinical Medicine*, Botrè et al., Eds., VCH, Weinheim, pp. 352-378 (1991).

Wu et al., "Cytoplasmic pH Responses to Carbonic Anydrase Inhibitors in Cultured Rabbit Nonpigmented Ciliary Epithelium," *J. Membrane Biol.*, 162: 31-38 (1998).

Wykoff et al., "Hypoxia-inducible Expression of Tumor-associated Carbonic Anhydrases," *Cancer Research*, 60: 7075-7083 (Dec. 15, 2000).

Yamagata et al., "The contribution of lactic acid to acidification of tumours: studies of variant cells lacking lactate dehydrogenase," *British Journal of Cancer*, 77(11): 1726-1731 (1998).

Zatovicova et al., "Monoclonal antibodies generated in carbonic anhydrase IX-deficient mice recognize different domains of tumour-associated hypoxia-induced carbonic anhydrase IX," *Journal of Immunological Methods*, 282: 117-134 (2003).

Fischer et al., "Acidic pH Inhibits Non-MHC-Restricted Killer Cell Functions," *Clin. Immunol.*, 93(3): 252-263 (Sep. 2000).

Fukumura et al., "Hypoxia and Acidosis Independently Up-Regulate Vascular Endothelial Growth Factor Transcription in Brain Tumors in Vivo," *Cancer Research*, 61: 6020-6024 (Aug. 15, 2001).

Helmlinger et al., "Acid Production in Glycolysis-impaired Tumors Provides New Insights into Tumor Metabolism," *Clinical Cancer Research*, 8: 1284-1291 (Apr. 2002).

Ivanov et al., "Down-regulation of transmembrane carbonic anhydrases in renal cell carcinoma cell lines by wild-type von Hippel-Lindau transgenes," *PNAS* (USA) 95: 12596-12601 (Oct. 1998).

Kaluz et al., "Lowered Oxygen Tension Induces Expression of the Hypoxia Marker MN/Carbonic Anhydrase IX in the Absence of Hypoxia-inducible Factor 1alpha Stabilization: A Role for Phosphatidylinositol 3'Kinase." *Cancer Research*, 62: 4469-4477 (Aug. 1, 2002).

Karumanchi et al., "VHL tumor supressor regulates CI-/HC03-exchange and Na+/H+ exchange activities in renal carcinoma cells," *Physiol. Genomics*, 5: 119-128 (2001).

Kato et al., "Induction of 103-kDa Gelatinase/Type IV Collagenase by Acidic Culture Conditions in Mouse Metastatic Melanoma Cell Lines," *J. Biol. Chem.*, 267(16): 11424-11430 (Jun. 5, 1992).

Martinez-Zaguilan et al., Acidic pH enhances the invasive behavior of human melanoma cells, *Clin. Exp. Metastasis*, 14: 176-186 (1996).

Mckhail et al., "HIF activation of pH-dependent nucleolar sequestration of VHL," *Nature Cell Biology*, 6(7): 642-647 (Jul. 2004).

Newell et al., "Studies with glycolysis-deficient cells suggest that production of lactic acid is not the only cause of tumor acidity," *PNAS* (USA), 90: 1127-1131 (Feb. 1993).

Pastorekova et al., "Carbonic anhydrase inhibitors: The first selective, membrane-impermeant inhibitors targeting the tumor-associated isozyme IX," *Bioorganic & Medicinal Chemistry Letters*, 14: 869-873 (2004).

Potter and Harris, "Diagnostic, prognostic and therapeutic implications of carbonic anhydrases in cancer," *Br. J. Cancer*, 89(1): 2-7 (Jul. 7, 2003).

Potter and Harris, "Hypoxia Inducible Carbonic Anhydrase IX, Marker of Tumor Hypoxia, Survival Pathway and Therapy Target," *Cell Cycle*, 3(2): 164-167 (Feb. 2004).

Ragbunand and Gillies, "pH and chemotherapy," *Novartis Foundation Symposium*, 240: 199-211 (2001).

Robertson et al., "Role of Carbonic Anhydrase IX in Human Tumor Cell Growth, Survival, and Invasion," *Cancer Research*, 64(17): 6160-6165 (Sep. 1, 2004).

Sterling et al., "A Transport Metabolon," *J. Biol. Chem.*, 276(51): 47886-47894 (Dec. 21, 2001).

Sterling et al., "The Extracellular Component of a Transport Metabolon," *J. Biol. Chem.*, 277(28): 25239-25246 (Jul. 12, 2002).

Stubbs et al., "Causes and consequences of tumour acidity and implications for treatment," *Mol. Med. Today*, 6: 15-19 (Jan. 2000).

Supuran et al., "Carbonic anhydrase inhibitors—Part 49**: Synthesis of substituted ureido and thioureido derivatives of aromatic/heterocyclic sulfonamides with increased affinities for isozyme I," *Eur. J. Med. Chem.*, 33: 83-93 (1998).

Svastova et al., "Hypoxia activates the capacity of tumor-associated carbonic anhydrase IX to acidify extracellular pH," *FEBS Letters*, 577(3): 439-445 (Nov. 19, 2004).

Tanaka et al., "In situ detection of activated caspase-3 in apoptotic granule neurons in the developing cerebellum in slice cultures and in vivo," *Developmental Brain Research*, 121(2): 223-228 (2000).

Workman and Stratford, "The experimental development of bioreductive drugs and their role in cancer therapy," *Cancer and Matastasis Reviews*, 12: 73-82 (1993).

\* cited by examiner

|     |     |     |     |     |     |     |     |     |     |     |     |     |
|---|---|---|---|---|---|---|---|---|---|---|---|---|
| 1   |     |     |     |     | M   | A   | P   | L   | C   | P   | S   | P   | W   | L   | P   | L   | 12  |
| 1   | ACA | GTC | AGC | CGC | ATG | GCT | CCC | CTG | TGC | CCC | AGC | CCC | TGG | CTC | CCT | CTG | 48  |
| 13  | L   | I   | P   | A   | P   | A   | P   | V   | Q   | L   | T   | V   | L   | S   | L   | S   | 28  |
| 49  | TTG | ATC | CCG | GCC | CCT | GCT | CCA | GTC | CAA | CTC | ACT | GTG | CTG | CTG | TCA | TCA | 96  |
| 29  | L   | L   | L   | M   | L   | M   | P   | H   | P   | Q   | R   | L   | P   | R   | M   | Q   | 44  |
| 97  | CTG | CTG | CTT | CTG | ATG | CTG | CCT | CAT | CCC | CAG | AGG | TTG | CCC | CGG | ATG | CAG | 144 |
| 45  | E   | D   | S   | P   | L   | G   | G   | G   | S   | S   | S   | G   | E   | D   | P   | L   | 60  |
| 145 | GAG | GAT | TCC | CCC | TTG | GGA | GGA | GGC | TCT | TCT | TCT | GGG | GAA | GAC | CCA | CTG | 192 |
| 61  | G   | E   | E   | D   | E   | E   | P   | S   | E   | E   | E   | E   | E   | E   | E   | E   | 76  |
| 193 | GGC | GAG | GAG | GAT | GAG | GAG | CCC | TCA | GAG | GAG | GAG | GAG | GAG | GAG | GAG | GAG | 240 |
| 77  | P   | P   | L   | D   | L   | P   | K   | P   | D   | E   | E   | S   | G   | S   | E   | L   | 92  |
| 241 | CCA | CCC | CTA | GAT | CTA | CCT | AAA | CCT | GAT | GAA | GAG | TCA | GGG | TCC | GAG | CTG | 288 |
| 93  | E   | D   | L   | E   | V   | K   | P   | T   | V   | E   | A   | P   | G   | D   | Q   | E   | 108 |
| 289 | GAG | GAT | CTA | GAA | GTT | AAG | CCT | ACT | GTT | GAA | GCT | CCT | GGA | GAT | CAA | GAA | 336 |
| 109 | K   | L   | E   | D   | L   | P   | H   | R   | D   | K   | E   | G   | D   | D   | S   | H   | 124 |
| 337 | AAG | TTA | GAG | GAT | CTA | CCT | CAC | AGG | GAC | AAA | GAA | GGG | GAT | GAC | AGT | CAT | 384 |
| 125 | P   | Q   | N   | N   | A   | G   | K   | E   | A   | P   | G   | D   | D   | V   | A   | C   | 140 |
| 385 | CCC | CAG | AAT | AAT | GCC | GGA | AAA | GAA | GCT | CCT | GGG | GAT | GAC | GTG | GCC | TGC | 432 |
| 141 | W   | R   | Y   | G   | D   | P   | P   | W   | R   | V   | S   | P   | A   | A   | A   | A   | 156 |
| 433 | TGG | CGC | TAT | GGA | GAC | CCG | CCC | TGG | CGG | GTG | TCC | CCA | GCC | AGT | GCC | GCC | 480 |
| 157 | A   | G   | R   | F   | Q   | S   | P   | V   | D   | I   | R   | P   | Q   | L   | A   | A   | 172 |
| 481 | GCG | GGC | CGC | TTC | CAG | TCC | CCG | GTG | GAT | ATC | CGC | CCC | CAG | CTC | GCC | GCC | 528 |

```
173  F   C   P   A   L   R   P   L   E   L   G   F   Q   L   P        188
529  TTC TGC CCG GCC CTG CGC CCC CTG GAA CTC GGC TTC CAG CTC CCG       576

189  P   L   P   E   L   R   L   G   N   A   M   S   V   Q   L        204
577  CCG CTC CCA GAA CTG CGC CTG GGG AAT GCT AGT CAA CTG              624

205  T   L   P   P   G   L   E   M   A   L   W   H   S   G   Y        220
625  ACC CTG CCT CCT GGG CTA GAG ATG GCT CTG TGG CAC AGT TAC          672

221  R   A   Q   L   H   L   H   R   G   F   P   G   R   E   Y        236
673  CGG GCT CTG CAG CTG CAT CTG CAC CGT GGG TTC CCC CGG GAG TAC      720

237  S   E   H   T   V   E   A   R   F   V   D   P   A   E   Y        252
721  TCG GAG CAC ACT GTG GAA GCC CGT TTC GTT GAC CCT GCA GAG TAC      768

253  V   H   L   T   S   A   V   A   A   F   L   S   R   E   I        268
769  GTT CAC CTC ACC AGC GCC GTG GCC GCC TTT CTG TCT CGC GAG ATC      816

269  P   G   G   L   A   V   L   Q   P   G   V   E   E   G   P        284
817  CCG GGA GGC CTG GCC GTG TTG CAG CCA GGA GTC GAG GAG GGC CCG      864

285  E   N   S   A   Y   E   T   R   S   L   E   E   I   S   A        300
865  GAA AAC AGT GCC TAT GAG ACT AGC CTG GAA GAA ATC TCT GCA          912

301  E   G   S   D   F   Q   R   Y   Q   L   G   Y   E   G   L        316
913  GAG GAA GGC TCA GAG ACT CAA CGC TAC TTC CAA CTG TAT GAG GGG CTC  960

317  L   P   S   D   F   S   V   P   Y   I   W   T   V   L   T        332
961  CTG CCC TCT GAC TTC AGC GTG CGC TAC TAC TTC TGG ATC GAG GGG ACT  1008

333  T   P   A   C   Q   G   V   F   N   Q   T                        348
1009 ACA CCG CCC TGT GCC CAG GGT GTC TTT AAC CAG ACA                  1056
```

```
349   V   M   L   S   A   K   Q   L   H   T   L   S   D   T   L   W   364
1057  GTG ATG CTG AGT GCT AAG CAG CTC CAC ACC CTC TCT GAC ACC CTG TGG 1104

365   G   P   G   D   S   R   L   Q   N   F   R   A   T   Q   P   380
1105  GGA CCT GGT GAC TCT CGG CTA CAG AAC TTC CGA GCG ACG CAG CCT 1152

381   L   N   G   R   V   I   E   A   S   F   P   A   G   V   D   S   396
1153  TTG AAT GGG CGA GTG ATT GAG GCC TCC TTC CCT GCT GGA GTG GAC AGC 1200

397   S   P   R   A   A   E   P   V   Q   L   N   S   C   L   A   A   412
1201  AGT CCT CGG GCT GCT GAG CCA GTC CAG CTG AAT TCC TGC CTG GCT GCT 1248

413   G   D   I   L   A   L   V   F   G   L   F   R   V   T   S   428
1249  GGT GAC ATC CTA GCC CTG GTT TTT GGC CTC TTT GCT GTC ACC AGC 1296

429   V   A   F   L   V   Q   M   R   R   H   Q   R   A   E   T   G   K   444
1297  GTC GCG TTC CTT GTG CAG ATG AGA AGA CAC CAG CGA GCA GAG ACT GGA ACC AAA 1344

445   G   G   V   S   Y   R   P   A   E   V   A   E   T   G   A   *   460
1345  GGG GGT GTG AGC TAC CGC CCA GCA GAG GTA GCC GAG ACT GGA GCC TAG 1392

1393  AGG CTG GAT CTT GGA GAA TGT CCT GTC CTC ATT ATG CCA CTT AAC 1440

1441  GGA GCC GGT AAC TGT CTC ATC TGA GGG 1488

1489  TGC CAA GAA ATT TTT TAA AAT AAA TAT TTA TAA T 1522
```

```
   1 ggatcctgtt gactcgtgac cttaccccca accctgtgct ctctgaaaca tgagctgtgt
  61 ccactcaggg ttaaatggat taagggcggt gcaagatgtg ctttgttaaa cagatgcttg
 121 aagcagcat gctcgttaag agtcatcacc aatccctaat ctcaagtaat cagggacaca
 181 aacactgcgg aaggccgcag ggtcctctgc ctaggaaaac cagagacctt tgttcacttg
 241 tttatctgac cttccctcca ctattgtcca tgaccctgcc aaatccccct ctgtgagaaa
 301 cacccaagaa ttatcaataa aaaaataaat ttaaaaaaaa aatacaaaaa aaaaaaaaaa
 361 aaaaaaaaaa gacttacgaa tagttattga taaatgaata gctattggta aagccaagta
 421 aatgatcata ttcaaaaacca gacgccatc atcacagctc aagtctacct gattgatct
 481 ctttatcatt gtcattcttt ggattcacta cctcctcaaa catcctccca atttctccccc
 541 aagttctaat tacgttccaa acattaggg gtacatgaa gcttgaacct actaccttct
 601 ttgcttttga gccatgagtt gtaggaatga tgagtttaca cttacatgc tgggattaa
 661 tttaactttt acctctaagt cagttgggta gcctttggct tatttttgta gctaattttg
 721 tagttaatgg atgcactgtg aatcctgcta tgatagtttt cctccacact ttgccactag
 781 gggtaggtag gtactcagtt ttcagtaatt gcttacctaa gaccctaagc cctattctc
 841 ttgtactggc ctttatctgt aatatgggca tatttaatac aatataattt ttggagtttt
 901 tttgttttgtt tgttttgttg tttttttgag acggagtctt gcatctgtca cctcccagct
 961 ggagtagcag tggtgccatc tcggctcact gcaagctcca cctcccgagt tcacgccatt
1021 ttcctgcctc agcctcccga gtagctggga ctacaggcgc ccgccaccat gcccgctaa
1081 tttttgtat tttggtaga gacggggttt caccgtgtta gccagaatgg tctcgatctc
1141 ctgacttcgt gatccacccg cctcggcctc ccaaagttct gggattacag gtgtgagcca
1201 ccgcaccttgg ccaatttttt gagtcttttta aagtaaaaat atgtctttgta agctggtaac
1261 tatgtacat tccttttat ctgacggtca cattactcct tctctctctc tttgagtttg
1321 gcatgcatat gctactttt gcagtccttt cattacattt cttttccag atttgaagag
1381 catgttatat cttttagctt cacttggctt aaaggttct ctcattagcc taacacagtg
1441 tcattgttgg taccacttgg atcataagtg gaaaaacagt caagaaaattg cacagtaata
1501 cttgttgta agaggatga ttcaggtgaa tctgacacta agaactccc ctacctgagg
1561 tctgagattc ctctgacatt gctgtatata ggcttttcct ttgacagcct gtgactgcgg
1621 actattttc ttaagcaaga tatgctaaag ttttgtgagc cttttccag agagaggtct
1681 catatctgca tcaagtgaga acatataatg tctgcatgtt gaaactttgtt cctcagtgac aggaatgttt
1741 gcttgtgttt tatgctttta tatagacagg gaaactgtt cctcagtgac ccaaagagg
1801 tgggaattgt tattggatat catcattggc ccacgctttc ttgacagcct aacaattaag
1861 ggttcataat ctcaattctg tcagaattgg tacaagaaat agctgctatg tttcttgaca
1921 ttccacttgg taggaaataa gaatgtgaaa ctcttcagtt ggtgtgtc cct?gttttt
```

FIG._2A

```
1981 ttgcaatttc ctccttactg tgttaaaaaa aagtatgatc ttgctctgag aggtgaggca
2041 ttcttaatca tgatctttaa agatcaataa tataatcctt tcaaggatta tgtctttatt
2101 ataataaaga taatttgtct ttaacagaat caataattaa atcccttaaa ggattatatc
2161 tttgctgggc gcagtggctc acacctgtaa tcccagcact ttgggtggcc aagtggaag
2221 gatcaaattt gcctacttct atattatctt ctaaagcaga attcatctct cttccctcaa
2281 tatgatgata ttgacagggt ttgccctcac tcactagatt gtgagctcct gctcagggca
2341 ggtagcgttt tttgttttg tttttgtttt tctttttga gacaggtct tgctctgtca
2401 cccaggccag agtgcaatgg tacagtctca gctcactgca gcctcaaccg cctcggctca
2461 aaccatcatc ccatttcagc ctcctgagta gctgggacta ggctacatg ccattacacc
2521 tggctaattt tttgtatt ctagtagaga caggtttgg ccatgttgcc cgggctggtc
2581 tcgaactcct ggactcaagc aatccaccca cctcagcctc ccaaaatgag ggaccgtgtc
2641 ttattcattt ccatgtccct agtcatagc ccagtgctgg acctatggta gtactaaata
2701 aatatttgtt gaatgcaata gtaaatagca tttcagggag caagaactag attaacaaag
2761 gtggtaaaag gttggagaa aaaaataata gttaattg gctagagtat gagggagagt
2821 agtaggagac aagatggaaa gtctctctgg gcaaggtttt gaaggaagtt ggaagtcaga
2881 agtacacaat gtgcatatcg tgcaggcag tggggagcca atgaaggctt ttgagcagga
2941 gagtaatgtg ttgaaaaata aatataggtt aaacctatca aaaccctct gacacataca
3001 cttgctttc attcaagctc aagtttgtct cccacatacc agccccctcc ctcaccctcg
3061 ggctcccta gcagcctgcc ctacctcttt acctgcttcc cattacttaa agggatgtat
3121 acatgagctg ctttccctct cagccagagg acatggggg tggtggagtc ctgccttc
3181 ccctttctgtg cctgagctg ggaagcaggc caggttagc caggtgggc tgtcaagcag
3241 ctgggtggtg ccagggagag cctgcatagt gccaggtggt gccttgggtt ccaagctagt
3301 ccatgccccc gataaccttc tgcctgtgca cacacctgcc cctcactcca ccccatcct
3361 agctttggta tgggggagag ggcacagggc cagacaaacc tgtgagactt tggctccatc
3421 tctgcaaaag ggcgctctgt gagtcagcct gctccccctcc aggcttgctc ctccccacc
3481 cagctctcgt ttccaatgca cgtacagccc gtacacaccg tgtgctggga cacccACAG
3541 TCAGCCGCAT GGCTCCCCTG TGCCCCAGCC CCTGGCTCCC CCTGGCTGC TCTGTTGATC CCGGCCCCTG
3601 CTCCAGGCCT CACTGTGCAA CTGCTGCTGT CACCTTGGAGG AGGATCCCCC GGGAAGATG
3661 AGAGGTTGCC CCGGATGCAG GAGGATTCCC CCTTGGGAGG AGGCTCTTCT GGGAAGATG
3721 ACCCACTGGG CGAGGAGGAT CTGCCCAGTG AAGAGGATTC ACCCAGAGAG GAGGATCCAC
3781 CCGGAGAGGA GGATCTACCT GGAGAGGAGG ATCTACCTGG AGAGGAGGAT CTACCTGAAG
3841 TTAAGCCTAA ATCAGAAGAA GAGGGCTCCC TGAAGTTAGA TGAACCACT ACTGTTGAGG
3901 CTCCTGGAGA TCCTCAAGAA CCCCAGAATA ATGCCCACAG GGACAAAGAA Ggtaagtggt
```

FIG._2B

```
3961  catcaatctc  caaatccagg  ttccaggagg  ttcatgactc  cctcccata   cccagccta
4021  ggctctgttc  actcaggaa   ggaggggaga  ctgtactccc  cacagaagcc  cttccagagg
4081  tcccatacca  atatcccat   ccccactctc  ggaggtagaa  agggacagat  gtggagagaa
4141  aataaaaagg  gtgcaaaagg  agagaggtga  gctggatgag  atgggagaga  aggggaggc
4201  tggagaagag  aaagggatga  gaactgcaga  tgagagaaaa  aatgtgcaga  cagagaaaa
4261  aaataggtgg  agaaggagag  tcagagagtt  tgaggggaag  agaaaaggaa  agcttgggag
4321  gtgagtggg   taccagagac  aagcaagaag  agctggtaga  agtcatctca  tcttaggcta
4381  caatgaggaa  ttgagaccta  acacagcagg  tagagaaacg  tgcttcttg
4441  actcccaagc  caggaatttg  ggggaaaggg  ttggagacca  tacaaggcag  aggatgagt
4501  ggggagaaga  aagaagggag  aaagaaaga   tggtgtactc  actcatttgg  gactcaggac
4561  tgaagtgccc  actcacttt   tttttttt    tttttgagac  aaactttcac  tttgttgcc
4621  caggctgag   tgcaatgcg   cgatctcggc  tcactgcaac  ctccacctcc  cgggttcaag
4681  tgattctcct  gcctcagcct  ctagccaagt  agctgcgatt  acaggcatgc  gccaccacgc
4741  ccggctaatt  tttgtattt   tagtagagac  gggtttcgc   catgttggtc  agctggtct
4801  cgaactcctg  atctcaggtg  atccaaccac  cctgcctcc   caaagtgctg  ggattatagg
4861  cgtgagccac  agcgcctggc  ctgaagcagc  cactcacttt  tacagaccct  aagacaatga
4921  ttgcaagctg  gtaggattgc  tgtttggccc  acccagctgc  ggtgttgagt  ttgggtgcgg
4981  tctcctgtgc  tttgcacctg  gcccgcttaa  ggcattgtt   acccgtaatg  ctcctgtaag
5041  gcatctgcgt  ttgtgacatc  gttttggtcg  ccaggaaggg  attgggctc   taagcttgag
5101  cggttcatcc  tttcattta   tacagGGGAT  GACCAGAGTC  ATTGGCGCTA  TGGAGgtgag
5161  acacccacc   gctgcacaga  cccaatctgg  gaaccacagct ctgtgatct   ccctacagc
5221  cgtccctgaa  cactggtccc  gggcgtccca  cccgccgcc   accgtcccac  cccctcacct
5281  tttctacccg  ggttccctaa  gttcctgacc  taggcgtcag  acttcctcac  tatactctcc
5341  caccccagGC  GACCCGGCCT  GGCCCCCGGGT GCCCCAGCC   TGCGCGGGCC  GCTTCCAGTC
5401  CCCGGTGGAT  ATCCGCCCCC  AGCTCGCCGC  CTTCTGCCCG  GCCCTGCGCC  CCCTGGAACT
5461  CCTGGGCTTC  CAGCTCCCCG  CGCTCCCAGA  ACTGCGCCTG  CGCAACAATG  GCCACAGTGg
5521  tgaggggtc   tcccccgcga  gactttggga  tgggggga    cgcagggaag  ggaaccgtcg
5581  cgcagtgcct  gccccggggt  tgggctggcc  ctaccgggcg  gggccggctc  acttgcctct
5641  ccctacgcag  TGCAACTGAC  CCTGCCTCCT  GGGCTAGAGA  TGGCTCTGGG  TCCCGGGCGG
5701  GAGTACCGGG  CTCTGCAGCT  GCATCTGCAC  TGGGGGGCTG  CAGGTCGTCC  GGGCTCGGAG
5761  CACACTGTGG  AAGGCCACCG  TTTCCCTGCC  GAGtgagcg   gtgccctct   cctaccctcg  tgtcctttc
5821  aaaggagcgg  ggcggacggg  ggccagagac  TTGCCAGAGT  TGACGAGGCC  TTGGGGCGCC
5881  agATCCACGT  GGTTCACCTC  AGCACCGCCT
```

FIG._2C

```
5941 CGGGAGGCCT GGCCGTGTTG GCCGCCTTTC TGGAGgtacc agatcctgga caccccctac
6001 tcccgcttt cccatcccat gctcctcccg gactctatcg tggagccaga gacccatcc
6061 cagcaagctc actcagccc ctgctgaca aactcattca cgcactgttt gttcatttaa
6121 cacccactgt gaaccaggca ccagccccca acaaggattc tgaagctgta gtccttgcc
6181 tctaaggagc ccacagccag tgggggaggc tgacatgaca gacacatagg aaggacatag
6241 taaagatggt ggtcacagag gaggtgacac ttaaagcctt cactggtaga aagaaaagg
6301 agtgttcat tgcagaggaa acagaatgt caaagactca gaatatgcc tatttaggga
6361 atggctacat acaccatgat tagaggaggc ccagtaaagg gaagggatgg tgagatgcct
6421 gctaggttca ctcactcact tttattatt tatttatttt tttgacagtc tctctgtcgc
6481 ccaggctgga gtgcagtggt gtgatcttgg gtcactgcaa cttccgcctc ccgggttcaa
6541 gggattctcc tgcctcagct tcctgagtag ctggggttac agtgtgtgc caccatgccc
6601 agctaattt tttttgtatt tttagtagac agggtttcac catgttggtc agctggtct
6661 caaactcctg gcctcaagtg atccgcctga ctcagcctac caaagtgctg attacaagtg
6721 tgagccaccg tgcccagcca cactcactga ttctttaatg ccagccacac agcacaaagt
6781 tcagagaaat gcctccatca tagcatgtca atatgttcat actcttaggt tcatgatgtt
6841 cttaacatta ggttcatag caaaataaga ataaaagaata ataaataaaa gaagtgcat
6901 gtcagacct cacctgaaaa gccaaacaca gaatcatgaa gtgaatgca gaggtgacac
6961 caacacaaag gtgtatatat ggtttcctgt gggagtatg tacggaggca gcagtgagtg
7021 agactgcaaa cgtcagaagg gcacgggtca ctgagagcct agtatcctag taaagtgggc
7081 tctctcct tctctccagc ttgtcattga aaaccagtcc accaagcttg ttggttcgca
7141 cagcaagagt acatagagtt tgaaataata catggattt taagaggag acactgtctc
7201 taaaaaaaa aacaacagca acaacaaaca gcaacaacca ttacaatttt atgttcctc
7261 agcattctca gagctgagga atgggagagg actatggaa ccccttcat gttccggcct
7321 tcagccatgg ccctggatac atgcactcat ctgtcttaca atgtcattcc ccagGAGGG
7381 CCCGAAGAA AACACAGTGCCT ATGAGCAGTT GCTGTGTCTCGC TTGGAAGAAA TCGCTGAGGA
7441 AGtcagttt gttggtctgg ccactaatct ctgtggccta gttcataag aatcaccctt
7501 tggagcttca ggtctgaggc tggagatggg ctccctccag tgcaggaggg attgaagcat
7561 gagccagcgc tcatcttgat aataaccatg aagctgacag acacagttac ccgcaaacgg
7621 ctgcctacag attgaaaac agcaaaaac cgccgggcac ggtggctcac gcctgtaatc
7681 ccagcacttt gggaggccaa ggcaggtgga tcacgaggtc aagagatcaa gaccatcctg
7741 gccaacatgg tgaaacccca tctctactaa aaatacgaaa aaatagccag gcgtggtggc
7801 gggtgcctgt aatcccagct actcgggagg ctgaggcagg agaatggcat gaaccggga
7861 ggcagaagtt gcagtgagcc gagatcgtgc cactgcactc cagcctgggc aacagagcga
```

FIG._2D

```
7921  gactcttgtc  tcaaaaaaaa  aaaaaaaaaa  gaaaaccaag  caaaaaccaa  aatgagacaa
7981  aaaaaacaag  accaaaaaat  ggtgtttgga  aattgtcaag  gtcaagtctg  gagagctaaa
8041  cttttctga   gaactgttta  tctttaataa  gcatcaaata  ttttaacttt  gtaaatactt
8101  ttgttggaaa  tcgttctctt  cttagtcact  cttgggtcat  tttaaatctc  acttactcta
8161  ctagacctt   taggtttctg  ctagactagg  tagaactctg  cctttgcatt  tcttgtgtct
8221  gttttgtata  gttatcaata  ttcatattta  tttacaagtt  attcagatca  ttttttcttt
8281  tcttttttt   tttttttttt  tttttttacat cttagtaga  gacaggtttt  caccatattg
8341  gccaggctgc  tctcaaactc  ctgaccttgt  gatccaccag  cctcggcctc  ccaaagtgct
8401  gggattcatt  tttctttt    aatttgctct  gggcttaaac  ttgtgccca   gcactttatg
8461  atgtacaca   gagttaagag  tgtagactca  gacggtcttt  cttcttttcct tctcttcctt
8521  cctccctccc  ctcccacctt  cccttctctc  cttcctttct  ttcttcctct  ctgcttcct
8581  caggcctctt  ccagtgtctc  caaagccctg  tacttttttt  tgagttaacg  tctttatggga
8641  agggcctgca  cttagtgaag  aagtggtctc  agagttgagt  tacccttgct  tctggaggt
8701  gaaactgtat  ccctataccc  tgaagcttta  aggggtgca   atgtagatga  gacccaaca
8761  tagatcctct  tcacagGCTC  AGAGACTCAG  GTCCCAGGAC  TGGACATATC  TGCACTCCTG
8821  CCCTCTGACT  TCAGCCGCTA  CTTCCAATAT  GAGGGGTCTC  TGACTACACC  GCCCTGTGCC
8881  CAGGGTGTCA  TCTGGACTGT  GTTAACCAG   ACAGTGATGC  TGAGTGCTAA  GCAGgtgggc
8941  ctgggtgtg   tgtggacaca  gtgggtgcgg  gggaaagagg  atgtaagatg  agatgagaaa
9001  caggagaaga  aagaaatcaa  ggctgggctc  tgtgcttac   gcctataatc  ccaccacgtt
9061  gggaggctga  ggtgggagaa  tggtttgagc  ccaggagttc  aagacaaggc  gggcaacat
9121  agtgtgaccc  catctctacc  aaaaaaaacc  caacaaaaacc aaaaatagcc  gggcatggtg
9181  gtatgcggcc  tagtcccagc  tactcaagga  ggctgaggtg  ggaagatcgc  ttgattccag
9241  gagtttgaga  ctgcagtgag  ctatgatccc  accactgcct  accatcttta  ggatacattt
9301  atttatttat  aaaagaaatc  aagaggctgg  atgggaata   caggagctgg  agggtggagc
9361  cctgaggtgc  tggttgtgag  ctggcctggg  accctttgttt cctgtcatgc  catgaaccca
9421  cccacactgt  ccactgacct  ccctagCTCC  ACACCCTCTC  TGACACCCTG  TGGGGACCTG
9481  GTGACTCTCG  GCTACACAGTG CCCTGCTGGA  AACTTCCGAG  CGACGCAGCC  CGAGTGATTG
9541  AGGCCTCCTT  CCCTGCTGGA  GTGGACAGCA  GTCCTCGGGC  TGCTGAGCCA  Ggtacagctt
9601  tgtctggttt  cccccagcc   agtagtcct   tatcctccca  tgtgtgtgcc  agtgtctgtc
9661  attggtggtc  acagcccgcc  tctcacatct  ccttttctc   tccagTCCAG  CTGAATTCCT
9721  GCCTGGCTGC  TGgtgagtct  gccccctccc  ttggtcctga  tgccaggaga  ctccctcagca
9781  ccattcagcc  ccagggctgc  tcaggaccgc  ctctgctccc  tctcccttc   tgcagaacag
9841  accccaaccc  caatattaga  gaggcagatc  atggtgggga  ttcccccatt  gtcccccagag
```

FIG. 2E

```
9901  gctaattgat tagaatgaag cttgagaaat ctcccagcat ccctctcgca aaagaatccc
9961  ccccccttt  tttaaagata gggtctcact ctgtttgccc caggctgggg tgttgtggca
10021 cgatcatagc tcactgcagc ctcgaactcc taggctcagg caatccttc  accttagctt
10081 ctcaaagcac tgggactgta ggcatgagcc actgtgcctg gcccaaacg  gccctttac
10141 ttggcttta  ggaagcaaaa acggtgctta tcttacccct tctcgtgtat ccaccctcat
10201 ccctggctg  gcctctcctg gagactgagg cactatgggg ctgcctgaga actcggggca
10261 ggggtggtgg agtgcactga ggcaggtgtt gaggaactct gcagacccct ctccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGATGAGA AGGCAGCACA Ggtattacac
10441 tgacccttc  ttcaggcaca agcttccccc acccttgtgg agtcacttca tgcaaagcgc
10501 atgcaaatga gctgtccctg ggccagtttt ctgattagcc tttcctgttg tgtacacaca
10561 gAAGGGGAAC CAAAGGGGGT GTGAGCTACC GCCCAGCAGA GGTAGCCGAG ACTGGAGCCT
10621 AGAGGCTGGA TCTTGGAGAA TGTGAGAAGC CAGCCAGAGG CATCTGAGGG GGAGCCGTA
10681 ACTGTCCTGT CCTGCTCATT ATGCCACTTC CTTTTAACTG CCAAGAAATT TTTTAAAATA
10741 AATATTTATA ATaaaatatg tgttagtcac ctttgttccc caaatcagaa ggaggtattt
10801 gaattccta  ttactgttat tagcaccaat ttagtggtaa tgcatttatt ctattacagt
10861 tcggcctcct tccacacatc actccaatgt gttgctcc
```

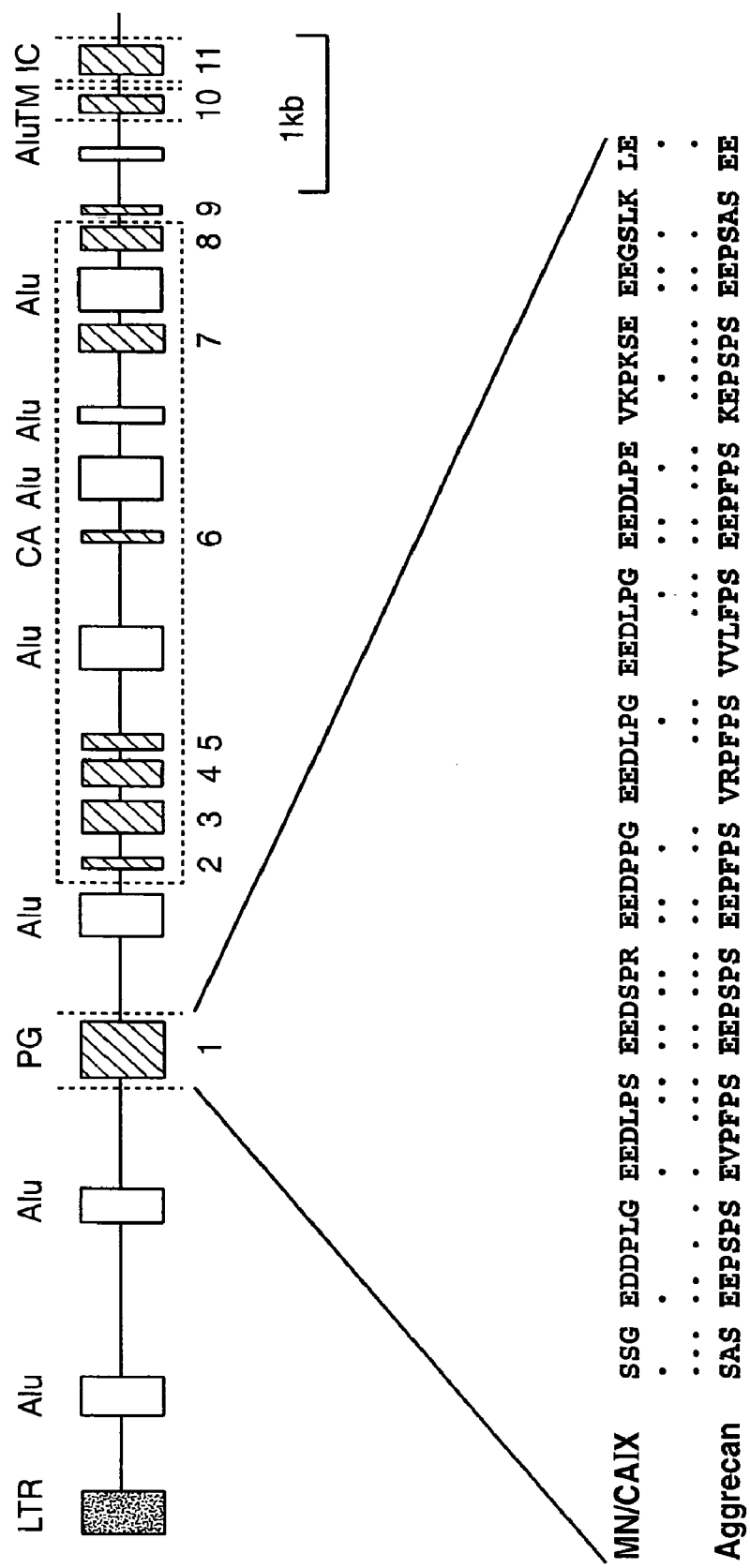
FIG._3

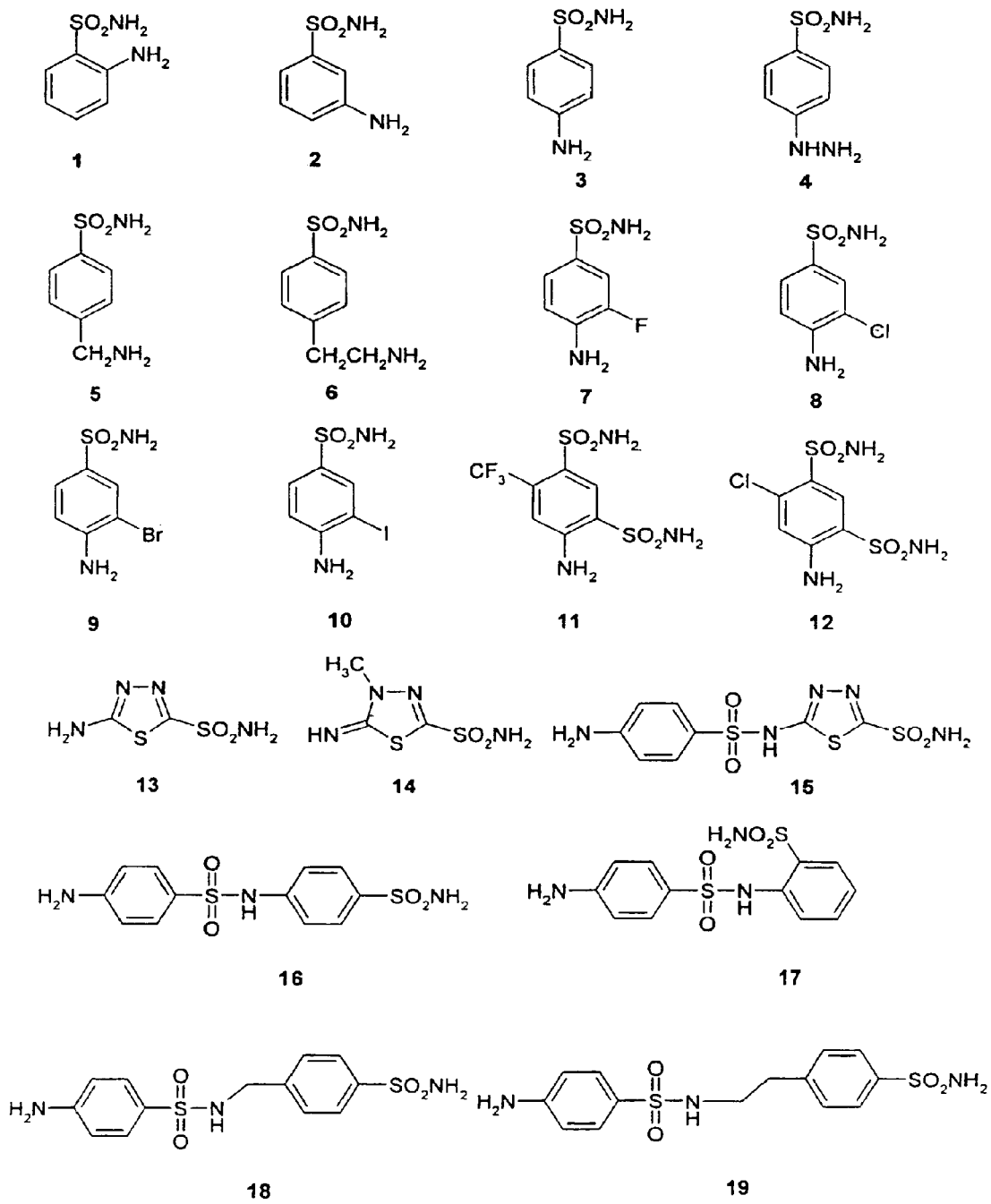
FIG._4A

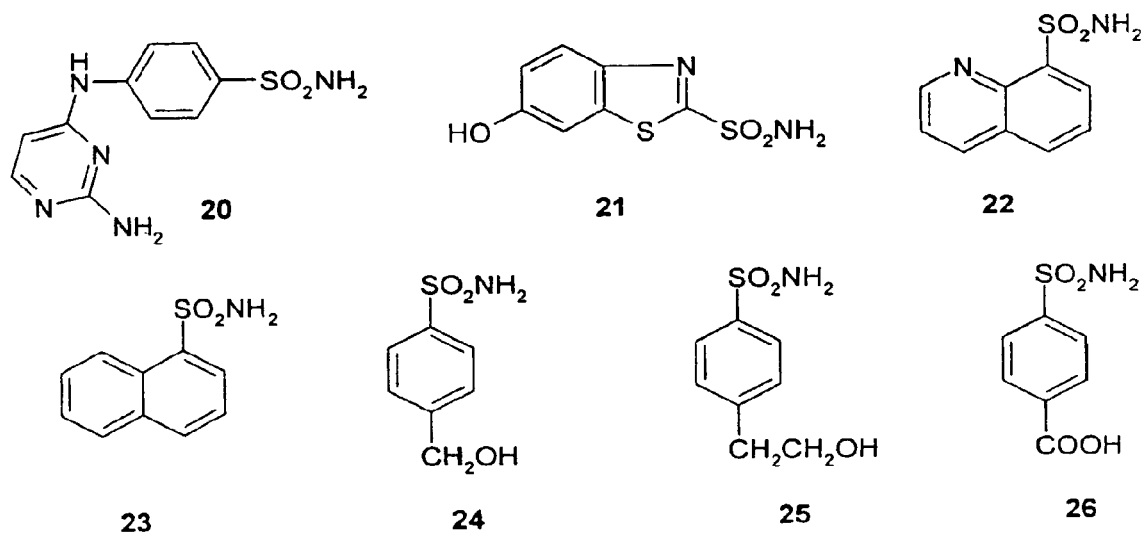
FIG._4B

Scheme 1
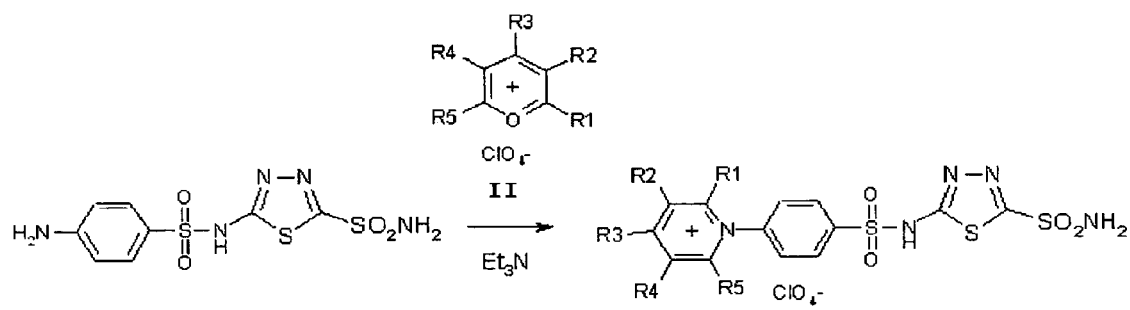
FIG._5
Scheme 2
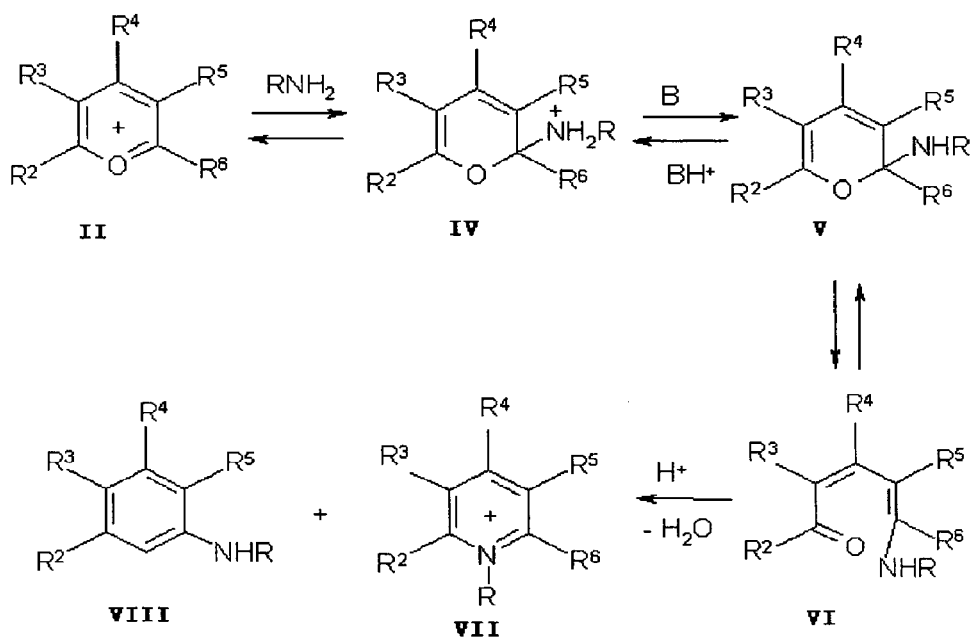
(For R6 or R2 Me)
FIG._6

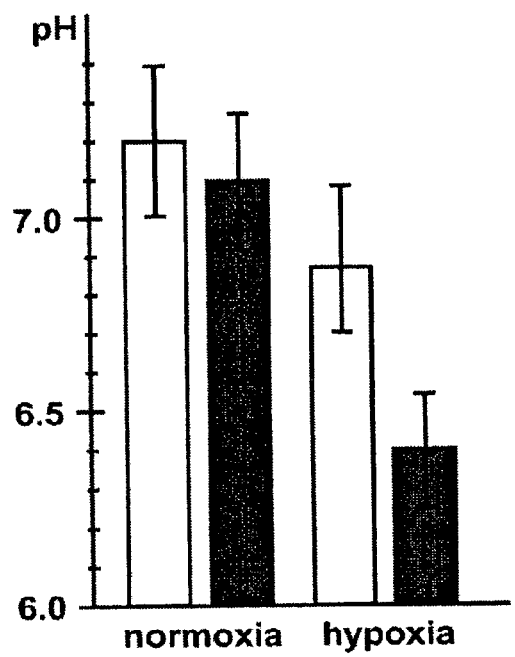
FIG._7A
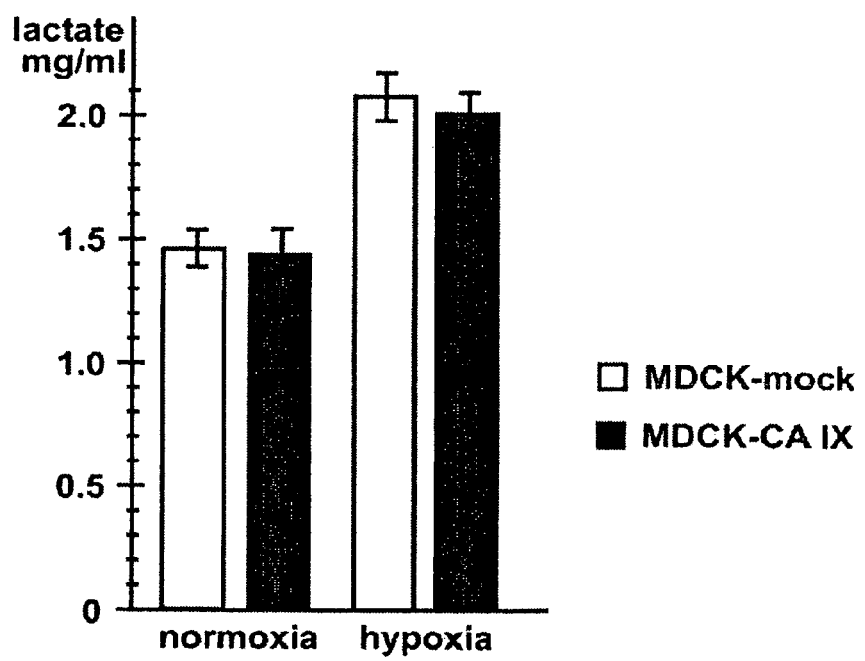
FIG._7B

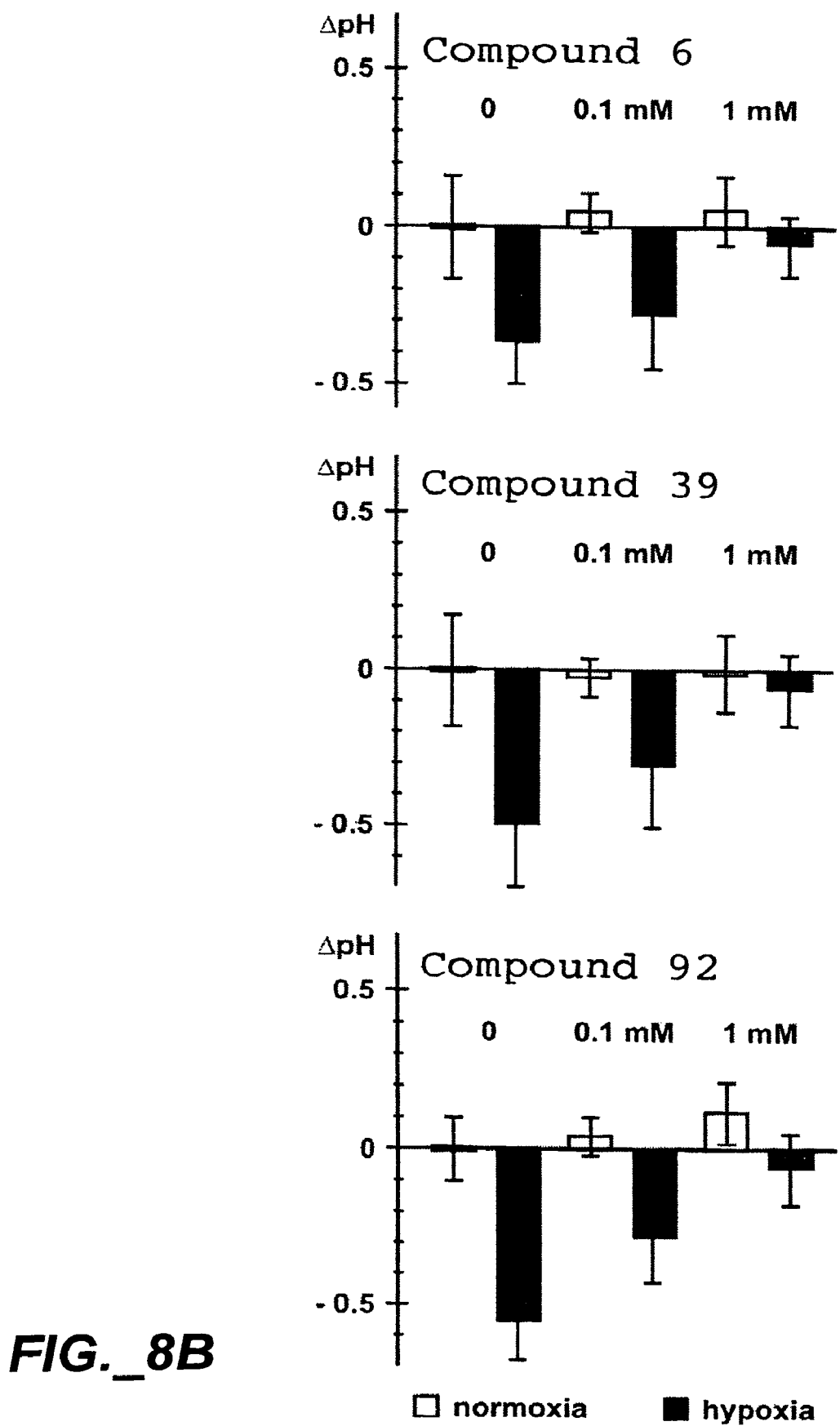
FIG._8B

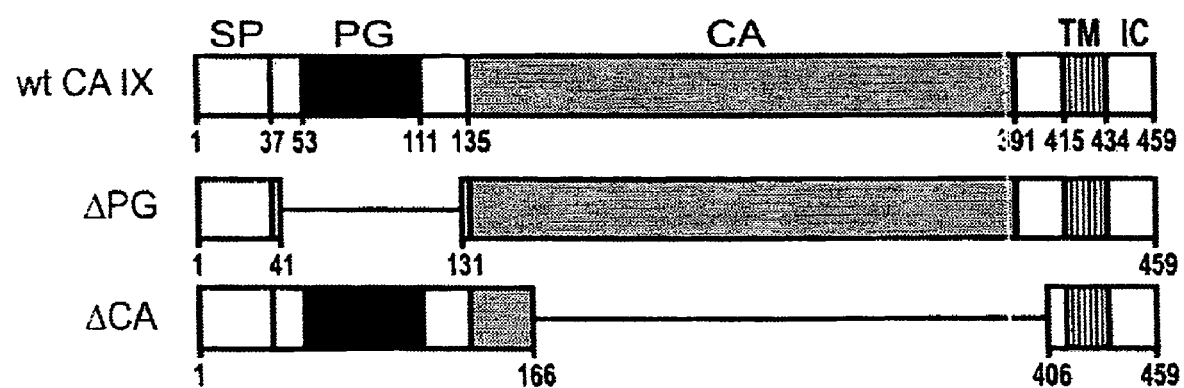
*FIG._9A*

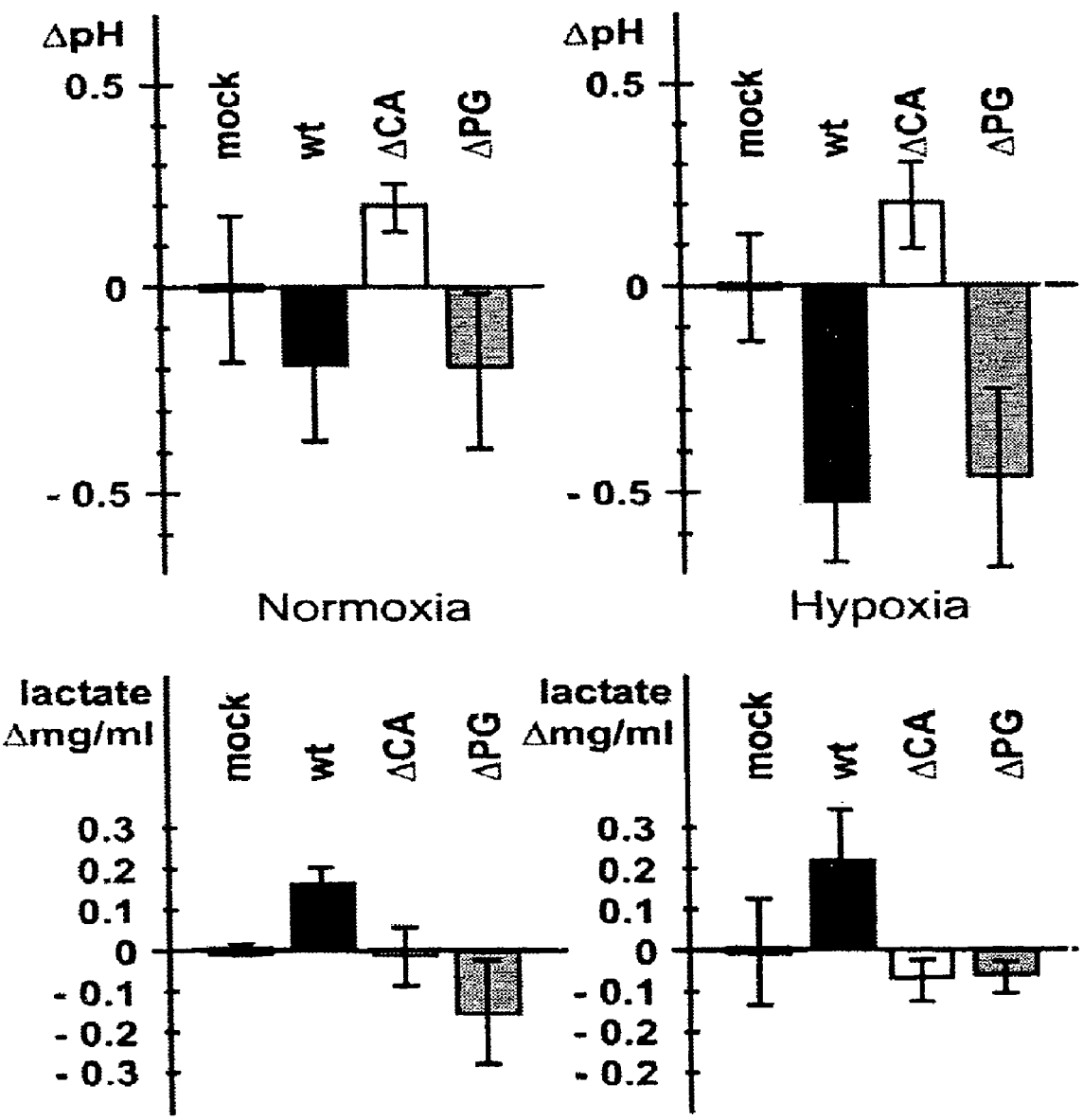
FIG._9B

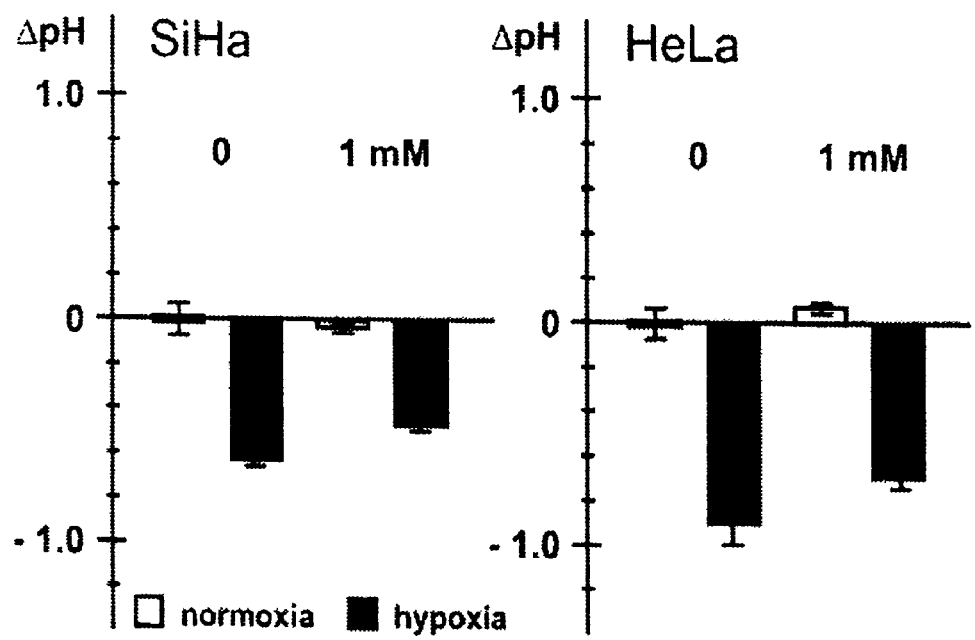
FIG._10
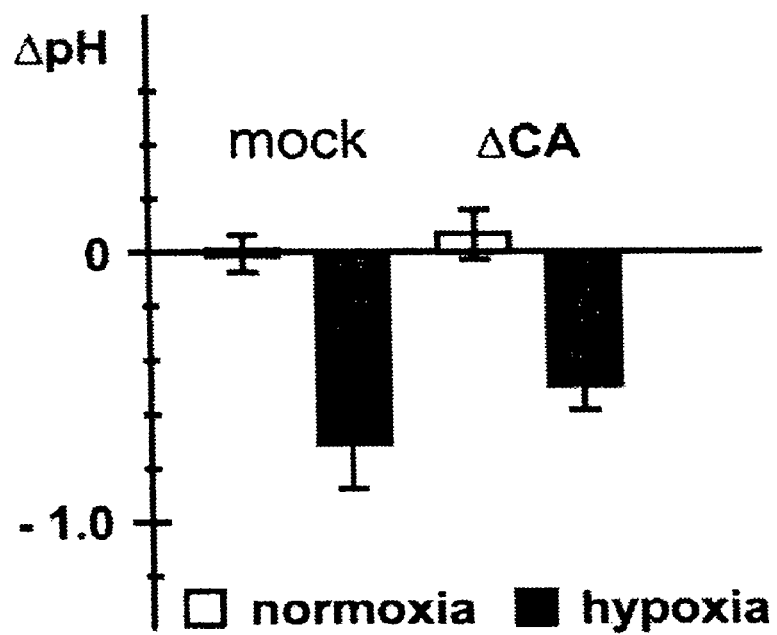
FIG._11

SEQUENCE LISTING

<160> NUMBER OF SEQ ID NOS: 9

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1

```
acagtcagcc gc atg gct ccc ctg tgc ccc agc ccc tgg ctc cct ctg ttg        51
           Met Ala Pro Leu Cys Pro Ser Pro Trp Leu Pro Leu Leu
               -35             -30             -25 atc ccg gcc cct gct cca ggc ctc act gtg caa ctg ctg ctg tca ctg          99
Ile Pro Ala Pro Ala Pro Gly Leu Thr Val Gln Leu Leu Leu Ser Leu
            -20             -15             -10 ctg ctt ctg atg cct gtc cat ccc cag agg ttg ccc cgg atg cag gag         147
Leu Leu Leu Met Pro Val His Pro Gln Arg Leu Pro Arg Met Gln Glu
        -5              -1  1               5 gat tcc ccc ttg gga gga ggc tct tct ggg gaa gat gac cca ctg ggc         195
Asp Ser Pro Leu Gly Gly Gly Ser Ser Gly Glu Asp Asp Pro Leu Gly
    10              15              20 gag gag gat ctg ccc agt gaa gag gat tca ccc aga gag gag gat cca         243
Glu Glu Asp Leu Pro Ser Glu Glu Asp Ser Pro Arg Glu Glu Asp Pro
25              30              35              40 ccc gga gag gag gat cta cct gga gag gag gat cta cct gga gag gag         291
Pro Gly Glu Glu Asp Leu Pro Gly Glu Glu Asp Leu Pro Gly Glu Glu
                45              50              55 gat cta cct gaa gtt aag cct aaa tca gaa gaa gag ggc tcc ctg aag         339
Asp Leu Pro Glu Val Lys Pro Lys Ser Glu Glu Glu Gly Ser Leu Lys
            60              65              70 tta gag gat cta cct act gtt gag gct cct gga gat cct caa gaa ccc         387
Leu Glu Asp Leu Pro Thr Val Glu Ala Pro Gly Asp Pro Gln Glu Pro
        75              80              85 cag aat aat gcc cac agg gac aaa gaa ggg gat gac cag agt cat tgg         435
Gln Asn Asn Ala His Arg Asp Lys Glu Gly Asp Asp Gln Ser His Trp
    90              95              100 cgc tat gga ggc gac ccg ccc tgg ccc cgg gtg tcc cca gcc tgc gcg         483
Arg Tyr Gly Gly Asp Pro Pro Trp Pro Arg Val Ser Pro Ala Cys Ala
105             110             115             120 ggc cgc ttc cag tcc ccg gtg gat atc cgc ccc cag ctc gcc gcc ttc         531
Gly Arg Phe Gln Ser Pro Val Asp Ile Arg Pro Gln Leu Ala Ala Phe
                125             130             135 tgc ccg gcc ctg cgc ccc ctg gaa ctc ctg ggc ttc cag ctc ccg ccg         579
Cys Pro Ala Leu Arg Pro Leu Glu Leu Leu Gly Phe Gln Leu Pro Pro
            140             145             150 ctc cca gaa ctg cgc ctg cgc aac aat ggc cac agt gtg caa ctg acc         627
Leu Pro Glu Leu Arg Leu Arg Asn Asn Gly His Ser Val Gln Leu Thr
        155             160             165 ctg cct cct ggg cta gag atg gct ctg ggt ccc ggg cgg gag tac cgg         675
Leu Pro Pro Gly Leu Glu Met Ala Leu Gly Pro Gly Arg Glu Tyr Arg
    170             175             180 gct ctg cag ctg cat ctg cac tgg ggg gct gca ggt cgt ccg ggc tcg         723
Ala Leu Gln Leu His Leu His Trp Gly Ala Ala Gly Arg Pro Gly Ser
185             190             195             200
```

-continued

| | | | | | | | | | | | | | | | |
|---|---|---|---|---|---|---|---|---|---|---|---|---|---|---|---|
| gag | cac | act | gtg | gaa | ggc | cac | cgt | ttc | cct | gcc | gag | atc | cac | gtg | gtt | 771
| Glu | His | Thr | Val | Glu | Gly | His | Arg | Phe | Pro | Ala | Glu | Ile | His | Val | Val |
| | | | 205 | | | | | 210 | | | | | 215 | | | cac ctc agc acc gcc ttt gcc aga gtt gac gag gcc ttg ggg cgc ccg  819
His Leu Ser Thr Ala Phe Ala Arg Val Asp Glu Ala Leu Gly Arg Pro
            220                 225                 230 gga ggc ctg gcc gtg ttg gcc gcc ttt ctg gag gag ggc ccg gaa gaa  867
Gly Gly Leu Ala Val Leu Ala Ala Phe Leu Glu Glu Gly Pro Glu Glu
            235                 240                 245 aac agt gcc tat gag cag ttg ctg tct cgc ttg gaa gaa atc gct gag  915
Asn Ser Ala Tyr Glu Gln Leu Leu Ser Arg Leu Glu Glu Ile Ala Glu
        250                 255                 260 gaa ggc tca gag act cag gtc cca gga ctg gac ata tct gca ctc ctg  963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca 1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg 1059
Pro Pro Cys Ala Gln Gly Val Ile Trp Thr Val Phe Asn Gln Thr Val
            300                 305                 310 atg ctg agt gct aag cag ctc cac acc ctc tct gac acc ctg tgg gga 1107
Met Leu Ser Ala Lys Gln Leu His Thr Leu Ser Asp Thr Leu Trp Gly
            315                 320                 325 cct ggt gac tct cgg cta cag ctg aac ttc cga gcg acg cag cct ttg 1155
Pro Gly Asp Ser Arg Leu Gln Leu Asn Phe Arg Ala Thr Gln Pro Leu
            330                 335                 340 aat ggg cga gtg att gag gcc tcc ttc cct gct gga gtg gac agc agt 1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt 1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc 1299
Asp Ile Leu Ala Leu Val Phe Gly Leu Leu Phe Ala Val Thr Ser Val
            380                 385                 390 gcg ttc ctt gtg cag atg aga agg cag cac aga agg gga acc aaa ggg 1347
Ala Phe Leu Val Gln Met Arg Arg Gln His Arg Arg Gly Thr Lys Gly
            395                 400                 405 ggt gtg agc tac cgc cca gca gag gta gcc gag act gga gcc           1389
Gly Val Ser Tyr Arg Pro Ala Glu Val Ala Glu Thr Gly Ala
            410                 415                 420 tagaggctgg atcttggaga atgtgagaag ccagccagag gcatctgagg gggagccggt 1449 aactgtcctg tcctgctcat tatgccactt ccttttaact gccaagaaat tttttaaaat 1509 aaatatttat aat                                                    1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
        -35                 -30                 -25

Pro Ala Pro Gly Leu Thr Val Gln Leu Leu Ser Leu Leu Leu Leu
    -20                 -15                 -10

Met Pro Val His Pro Gln Arg Leu Pro Arg Met Gln Glu Asp Ser Pro
-5              -1   1              5                   10

-continued

```
Leu Gly Gly Gly Ser Ser Gly Glu Asp Asp Pro Leu Gly Glu Glu Asp
            15                  20                  25
Leu Pro Ser Glu Glu Asp Ser Pro Arg Glu Glu Asp Pro Gly Glu
        30                  35                  40
Glu Asp Leu Pro Gly Glu Glu Asp Leu Pro Gly Glu Glu Asp Leu Pro
        45                  50                  55
Glu Val Lys Pro Lys Ser Glu Glu Gly Ser Leu Lys Leu Glu Asp
60                  65                  70                  75
Leu Pro Thr Val Glu Ala Pro Gly Asp Pro Gln Glu Pro Gln Asn Asn
                80                  85                  90
Ala His Arg Asp Lys Gly Asp Gln Ser His Trp Arg Tyr Gly
            95                  100                 105
Gly Asp Pro Pro Trp Pro Arg Val Ser Pro Ala Cys Ala Gly Arg Phe
            110                 115                 120
Gln Ser Pro Val Asp Ile Arg Pro Gln Leu Ala Ala Phe Cys Pro Ala
            125                 130                 135
Leu Arg Pro Leu Glu Leu Leu Gly Phe Gln Leu Pro Pro Leu Pro Glu
140                 145                 150                 155
Leu Arg Leu Arg Asn Asn Gly His Ser Val Gln Leu Thr Leu Pro Pro
                160                 165                 170
Gly Leu Glu Met Ala Leu Gly Pro Gly Arg Glu Tyr Arg Ala Leu Gln
            175                 180                 185
Leu His Leu His Trp Gly Ala Ala Gly Arg Pro Gly Ser Glu His Thr
            190                 195                 200
Val Glu Gly His Arg Phe Pro Ala Glu Ile His Val Val His Leu Ser
            205                 210                 215
Thr Ala Phe Ala Arg Val Asp Glu Ala Leu Gly Arg Pro Gly Gly Leu
220                 225                 230                 235
Ala Val Leu Ala Ala Phe Leu Glu Glu Gly Pro Glu Glu Asn Ser Ala
            240                 245                 250
Tyr Glu Gln Leu Leu Ser Arg Leu Glu Glu Ile Ala Glu Glu Gly Ser
            255                 260                 265
Glu Thr Gln Val Pro Gly Leu Asp Ile Ser Ala Leu Leu Pro Ser Asp
            270                 275                 280
Phe Ser Arg Tyr Phe Gln Tyr Glu Gly Ser Leu Thr Thr Pro Pro Cys
            285                 290                 295
Ala Gln Gly Val Ile Trp Thr Val Phe Asn Gln Thr Val Met Leu Ser
300                 305                 310                 315
Ala Lys Gln Leu His Thr Leu Ser Asp Thr Leu Trp Gly Pro Gly Asp
            320                 325                 330
Ser Arg Leu Gln Leu Asn Phe Arg Ala Thr Gln Pro Leu Asn Gly Arg
            335                 340                 345
Val Ile Glu Ala Ser Phe Pro Ala Gly Val Asp Ser Ser Pro Arg Ala
            350                 355                 360
Ala Glu Pro Val Gln Leu Asn Ser Cys Leu Ala Ala Gly Asp Ile Leu
            365                 370                 375
Ala Leu Val Phe Gly Leu Leu Phe Ala Val Thr Ser Val Ala Phe Leu
380                 385                 390                 395
Val Gln Met Arg Arg Gln His Arg Arg Gly Thr Lys Gly Gly Val Ser
            400                 405                 410
Tyr Arg Pro Ala Glu Val Ala Glu Thr Gly Ala
            415                 420
```

```
<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3
```

| | | | | | |
|---|---|---|---|---|---|
| ggatcctgtt | gactcgtgac | cttaccccca | accctgtgct | ctctgaaaca | tgagctgtgt | 60 |
| ccactcaggg | ttaaatggat | taagggcggt | gcaagatgtg | ctttgttaaa | cagatgcttg | 120 |
| aaggcagcat | gctcgttaag | agtcatcacc | aatccctaat | ctcaagtaat | cagggacaca | 180 |
| aacactgcgg | aaggccgcag | ggtcctctgc | ctaggaaaac | cagagacctt | tgttcacttg | 240 |
| tttatctgac | cttccctcca | ctattgtcca | tgaccctgcc | aaatccccct | ctgtgagaaa | 300 |
| cacccaagaa | ttatcaataa | aaaataaat | ttaaaaaaa | aatacaaaaa | aaaaaaaaa | 360 |
| aaaaaaaaa | gacttacgaa | tagttattga | taaatgaata | gctattggta | aagccaagta | 420 |
| aatgatcata | ttcaaaacca | gacggccatc | atcacagctc | aagtctacct | gatttgatct | 480 |
| ctttatcatt | gtcattcttt | ggattcacta | gattagtcat | catcctcaaa | attctccccc | 540 |
| aagttctaat | tacgttccaa | acatttaggg | gttacatgaa | gcttgaacct | actaccttct | 600 |
| ttgcttttga | gccatgagtt | gtaggaatga | tgagtttaca | ccttacatgc | tggggattaa | 660 |
| tttaaacttt | acctctaagt | cagttgggta | gcctttggct | tattttttgta | gctaattttg | 720 |
| tagttaatgg | atgcactgtg | aatcttgcta | tgatagtttt | cctccacact | ttgccactag | 780 |
| gggtaggtag | gtactcagtt | ttcagtaatt | gcttacctaa | gaccctaagc | cctatttctc | 840 |
| ttgtactggc | ctttatctgt | aatatgggca | tatttaatac | aatataattt | ttggagtttt | 900 |
| tttgtttgtt | tgtttgtttg | tttttttgag | acggagtctt | gcatctgtca | tgcccaggct | 960 |
| ggagtagcag | tggtgccatc | tcggctcact | gcaagctcca | cctcccgagt | tcacgccatt | 1020 |
| ttcctgcctc | agcctcccga | gtagctggga | ctacaggcgc | cgccaccat | gcccggctaa | 1080 |
| ttttttgtat | ttttggtaga | gacggggttt | caccgtgtta | gccagaatgg | tctcgatctc | 1140 |
| ctgacttcgt | gatccacccg | cctcggcctc | ccaaagttct | gggattacag | gtgtgagcca | 1200 |
| ccgcacctgg | ccaattttt | gagtctttta | aagtaaaaat | atgtcttgta | agctggtaac | 1260 |
| tatggtacat | ttcctttat | taatgtgtg | ctgacggtca | tataggttct | tttgagtttg | 1320 |
| gcatgcatat | gctactttt | gcagtccttt | cattacattt | ttctctcttc | atttgaagag | 1380 |
| catgttatat | cttttagctt | cacttggctt | aaaaggttct | ctcattagcc | taacacagtg | 1440 |
| tcattgttgg | taccacttgg | atcataagtg | gaaaaacagt | caagaaattg | cacagtaata | 1500 |
| cttgtttgta | agagggatga | ttcaggtgaa | tctgacacta | agaaactccc | ctacctgagg | 1560 |
| tctgagattc | ctctgacatt | gctgtatata | ggcttttcct | ttgacagcct | gtgactgcgg | 1620 |
| actattttc | ttaagcaaga | tatgctaaag | ttttgtgagc | cttttccag | agagaggtct | 1680 |
| catatctgca | tcaagtgaga | acatataatg | tctgcatgtt | tccatatttc | aggaatgttt | 1740 |
| gcttgtgttt | tatgctttta | tatagacagg | gaaacttgtt | cctcagtgac | ccaaaagagg | 1800 |
| tgggaattgt | tattggatat | catcattggc | ccacgctttc | tgaccttgga | aacaattaag | 1860 |
| ggttcataat | ctcaattctg | tcagaattgg | tacaagaaat | agctgctatg | tttcttgaca | 1920 |
| ttccacttgg | taggaaataa | gaatgtgaaa | ctcttcagtt | ggtgtgtgtc | cctngttttt | 1980 |

```
ttgcaatttc cttcttactg tgttaaaaaa aagtatgatc ttgctctgag aggtgaggca    2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact ttgggtggcc aaggtggaag    2220
gatcaaattt gcctacttct atattatctt ctaaagcaga attcatctct cttccctcaa    2280
tatgatgata ttgacagggt ttgccctcac tcactagatt gtgagctcct gctcagggca    2340
ggtagcgttt tttgtttttg ttttttgtttt tcttttttga cagggtct tgctctgtca     2400 cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc ccaaaatgag ggaccgtgtc    2640
ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg ctagagtat gagggagagt     2820 agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga    2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctccccta gcagcctgcc ctacctcttt acctgcttcc tggtggagtc agggatgtat    3120
acatgagctg cttccctct cagccagagg acatggggggg ccccagctcc cctgcctttc    3180
cccttctgtg cctggagctg ggaagcaggc cagggttagc tgaggctggc tggcaagcag    3240
ctgggtggtg ccagggagag cctgcatagt gccaggtggt gccttgggtt ccaagctagt    3300
ccatggcccc gataaccttc tgcctgtgca cacacctgcc cctcactcca cccccatcct    3360
agctttggta tgggggagag ggcacagggc cagacaaacc tgtgagactt tggctccatc    3420
tctgcaaaag ggcgctctgt gagtcagcct gctcccctcc aggcttgctc ctcccccacc    3480
cagctctcgt ttccaatgca cgtacagccc gtacacaccg tgtgctggga caccccacag    3540
tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccgatgcag gaggattccc ccttgggagg aggctcttct ggggaagatg     3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
```

```
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt ttttgagac aaactttcac ttttgttgcc     4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagacaatga    4920
ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacaggggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca cccgccgccc accgtcccac cccctcacct    5280
tttctacccg ggttccctaa gttcctgacc taggcgtcag acttcctcac tatactctcc    5340
caccccaggc gacccgccct ggcccgggt gtcccagcc tgcgcgggcc gcttccagtc     5400
cccggtggat atccgccccc agctcgccgc cttctgcccg gccctgcgcc cctggaact     5460 cctgggcttc cagctcccgc cgctcccaga actgcgcctg cgcaacaatg ccacagtgg    5520 tgaggggtc tccccgccga gacttgggga tggggcgggg cgcagggaag ggaaccgtcg    5580
cgcagtgcct gcccggggt tgggctggcc ctaccgggcg gggccggctc acttgcctct    5640
ccctacgcag tgcaactgac cctgcctcct gggctagaga tggctctggg tcccgggcgg    5700
gagtaccggg ctctgcagct gcatctgcac tgggggctg caggtcgtcc gggctcggag    5760
cacactgtgg aaggccaccg tttccctgcc gaggtgagcg cggactggcc gagaaggggc    5820
aaaggagcgg ggcggacggg ggccagagac gtggccctct cctaccctcg tgtccttttc    5880
agatccacgt ggttcacctc agcaccgcct ttgccagagt tgacgaggcc ttggggcgcc    5940
cgggaggcct ggccgtgttg gccgcctttc tggaggtacc agatcctgga cacccctac    6000 tccccgcttt cccatcccat gctcctcccg gactctatcg tggagccaga gaccccatcc    6060
cagcaagctc actcaggccc ctggctgaca aactcattca cgcactgttt gttcatttaa    6120
cacccactgt gaaccaggca ccagcccca acaaggattc tgaagctgta ggtccttgcc     6180
tctaaggagc ccacagccag tggggaggc tgacatgaca gacacatagg aaggacatag    6240
taaagatggt ggtcacagag gaggtgacac ttaaagcctt cactggtaga aaagaaaagg    6300
aggtgttcat tgcagaggaa acagaatgtg caaagactca gaatatggcc tatttaggga    6360
atggctacat acaccatgat tagaggaggc ccagtaaagg gaagggatgg tgagatgcct    6420
gctaggttca ctcactcact tttatttatt tatttatttt tttgacagtc tctctgtcgc    6480
ccaggctgga gtgcagtggt gtgatcttgg gtcactgcaa cttccgcctc ccgggttcaa    6540
gggattctcc tgcctcagct tcctgagtag ctggggttac aggtgtgtgc caccatgccc    6600
agctaatttt tttttgtatt tttagtagac agggtttcac catgttggtc aggctggtct    6660
caaactcctg gcctcaagtg atccgcctga ctcagcctac caaagtgctg attacaagtg    6720
tgagccaccg tgcccagcca cactcactga ttctttaatg ccagccacac agcacaaagt    6780
```

```
tcagagaaat gcctccatca tagcatgtca atatgttcat actcttaggt tcatgatgtt    6840
cttaacatta ggttcataag caaaataaga aaaagaata ataaataaaa gaagtggcat      6900
gtcaggacct cacctgaaaa gccaaacaca gaatcatgaa ggtgaatgca gaggtgacac    6960
caacacaaag gtgtatatat ggtttcctgt ggggagtatg tacggaggca gcagtgagtg    7020
agactgcaaa cgtcagaagg gcacgggtca ctgagagcct agtatcctag taaagtgggc    7080
tctctccctc tctctccagc ttgtcattga aaccagtcc accaagcttg ttggttcgca     7140
cagcaagagt acatagagtt tgaaataata cataggattt taagagggag acactgtctc    7200
taaaaaaaaa aacaacagca acaacaaaaa gcaacaacca ttacaatttt atgttccctc    7260
agcattctca gagctgagga atgggagagg actatgggaa ccccttcat gttccggcct     7320 tcagccatgg ccctggatac atgcactcat ctgtcttaca atgtcattcc cccaggaggg    7380
cccggaagaa aacagtgcct atgagcagtt gctgtctcgc ttggaagaaa tcgctgagga    7440
aggtcagttt gttggtctgg ccactaatct ctgtggccta gttcataaag aatcacccctt   7500 tggagcttca ggtctgaggc tggagatggg ctccctccag tgcaggaggg attgaagcat    7560
gagccagcgc tcatcttgat aataaccatg aagctgacag acacagttac ccgcaaacgg    7620
ctgcctacag attgaaaacc aagcaaaaac cgccgggcac ggtggctcac gcctgtaatc    7680
ccagcacttt ggggaggccaa ggcaggtgga tcacgaggtc aagagatcaa gaccatcctg    7740
gccaacatgg tgaaacccca tctctactaa aaatacgaaa aaatagccag gcgtggtggc    7800
gggtgcctgt aatcccagct actcggggag ctgaggcagg agaatggcat gaacccggga    7860
ggcagaagtt gcagtgagcc gagatcgtgc cactgcactc cagcctgggc aacagagcga    7920
gactcttgtc tcaaaaaaaa aaaaaaaaaa gaaaaccaag caaaaccaa aatgagacaa      7980 aaaaaacaag accaaaaaat ggtgtttgga aattgtcaag gtcaagtctg gagagctaaa    8040 cttttctga gaactgttta tctttaataa gcatcaaata ttttaacttt gtaaatactt       8100
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca ttttttcttt    8280
tctttttttt tttttttttt tttttacat ctttagtaga gacagggttt caccatattg      8340
gccaggctgc tctcaaactc ctgaccttgt gatccaccag cctcggcctc ccaaagtgct    8400
gggattcatt ttttctttt aatttgctct gggcttaaac ttgtggccca gcactttatg      8460
atggtacaca gagttaagag tgtagactca gacggtcttt cttctttcct tctcttcctt    8520
cctcccttcc ctcccacctt cccttctctc cttcctttct ttcttcctct cttgcttcct    8580 cagggcctctt ccagttgctc caaagccctg tactttttt tgagttaacg tcttatggga     8640
agggcctgca cttagtgaag aagtggtctc agagttgagt taccttggct tctgggaggt    8700
gaaactgtat ccctataccc tgaagcttta aggggggtgca atgtagatga acccccaaca    8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaaagagg atgtaagatg agatgagaaa    9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc caacaaaacc aaaatagcc gggcatggtg      9180
```

```
gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acaccctctc tgacaccctg tggggacctg    9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt cccccagcc agtagtccct tatcctccca tgtgtgtgcc agtgtctgtc    9660
attggtggtc acagcccgcc tctcacatct ccttttctc tccagtccag ctgaattcct    9720
gcctggctgc tggtgagtct gcccctcctc ttggtcctga tgccaggaga ctcctcagca    9780
ccattcagcc ccagggctgc tcaggaccgc ctctgctccc tctccttttc tgcagaacag    9840
accccaaccc caatattaga gaggcagatc atggtgggga ttcccccatt gtccccagag    9900
gctaattgat tagaatgaag cttgagaaat ctcccagcat ccctctcgca aaagaatccc    9960 ccccctttt tttaaagata gggtctcact ctgtttgccc caggctgggg tgttgtggca    10020
cgatcatagc tcactgcagc ctcgaactcc taggctcagg caatccttc accttagctt    10080 ctcaaagcac tgggactgta ggcatgagcc actgtgcctg ccccaaacg gccttttac    10140 ttggctttta ggaagcaaaa acggtgctta tcttacccct tctcgtgtat ccaccctcat    10200
cccttggctg gcctcttctg gagactgagg cactatgggg ctgcctgaga actcggggca    10260 gggtggtgg agtgcactga ggcaggtgtt gaggaactct gcagacccct cttccttccc    10320
aaagcagccc tctctgctct ccatcgcagg tgacatccta gccctggttt ttggcctcct    10380
ttttgctgtc accagcgtcg cgttccttgt gcagatgaga aggcagcaca ggtattacac    10440 tgacccttc ttcaggcaca agcttcccc acccttgtgg agtcacttca tgcaaagcgc    10500
atgcaaatga gctgctcctg gccagttttt ctgattagcc tttcctgttg tgtacacaca    10560 gaagggaac caaagggggt gtgagctacc gcccagcaga ggtagccgag actggagcct    10620
agaggctgga tcttggagaa tgtgagaagc cagccagagg catctgaggg ggagccggta    10680
actgtcctgt cctgctcatt atgccacttc cttttaactg ccaagaaatt ttttaaaata    10740
aatatttata ataaaatatg tgttagtcac cttttgttccc caaatcagaa ggaggtattt    10800
gaatttccta ttactgttat tagcaccaat ttagtggtaa tgcatttatt ctattacagt    10860
tcggcctcct tccacacatc actccaatgt gttgctcc                            10898
```

<210> SEQ ID NO 4
<211> LENGTH: 59
<212> TYPE: PRT
<213> ORGANISM: Homo sapiens

<400> SEQUENCE: 4

Ser Ser Gly Glu Asp Asp Pro Leu Gly Glu Glu Asp Leu Pro Ser Glu
1               5                   10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
    50                  55

```
<210> SEQ ID NO 5
<211> LENGTH: 257
<212> TYPE: PRT
<213> ORGANISM: Homo sapiens

<400> SEQUENCE: 5
```

Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
        35                  40                  45

Leu Gly Phe Gln Leu Pro Pro Leu Pro Glu Leu Arg Leu Arg Asn Asn
50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

Tyr Glu Gly Ser Leu Thr Thr Pro Pro Cys Ala Gln Gly Val Ile Trp
        195                 200                 205

Thr Val Phe Asn Gln Thr Val Met Leu Ser Ala Lys Gln Leu His Thr
210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

```
<210> SEQ ID NO 6
<211> LENGTH: 37
<212> TYPE: PRT
<213> ORGANISM: Homo sapiens

<400> SEQUENCE: 6
```

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro
        35

```
<210> SEQ ID NO 7
<211> LENGTH: 377
<212> TYPE: PRT
<213> ORGANISM: Homo sapiens
```

<400> SEQUENCE: 7

```
Gln Arg Leu Pro Arg Met Gln Glu Asp Ser Pro Leu Gly Gly Ser
  1               5                  10                  15
Ser Gly Glu Asp Asp Pro Leu Gly Glu Glu Asp Leu Pro Ser Glu
                 20                  25                  30
Glu Asp Ser Pro Arg Glu Glu Asp Pro Gly Glu Glu Asp Leu Pro Gly
                 35                  40                  45
Glu Glu Asp Leu Pro Gly Glu Glu Asp Leu Pro Glu Val Lys Pro Lys
             50                  55                  60
Ser Glu Glu Glu Gly Ser Leu Lys Leu Glu Asp Leu Pro Thr Val Glu
 65                  70                  75                  80
Ala Pro Gly Asp Pro Gln Glu Pro Gln Asn Asn Ala His Arg Asp Lys
                 85                  90                  95
Glu Gly Asp Asp Gln Ser His Trp Arg Tyr Gly Asp Pro Pro Trp
                100                 105                 110
Pro Arg Val Ser Pro Ala Cys Ala Gly Arg Phe Gln Ser Pro Val Asp
            115                 120                 125
Ile Arg Pro Gln Leu Ala Ala Phe Cys Pro Ala Leu Arg Pro Leu Glu
            130                 135                 140
Leu Leu Gly Phe Gln Leu Pro Pro Leu Pro Glu Leu Arg Leu Arg Asn
145                 150                 155                 160
Asn Gly His Ser Val Gln Leu Thr Leu Pro Gly Leu Glu Met Ala
                165                 170                 175
Leu Gly Pro Gly Arg Glu Tyr Arg Ala Leu Gln Leu His Leu His Trp
            180                 185                 190
Gly Ala Ala Gly Arg Pro Gly Ser Glu His Thr Val Glu Gly His Arg
            195                 200                 205
Phe Pro Ala Glu Ile His Val Val His Leu Ser Thr Ala Phe Ala Arg
            210                 215                 220
Val Asp Glu Ala Leu Gly Arg Pro Gly Gly Leu Ala Val Leu Ala Ala
225                 230                 235                 240
Phe Leu Glu Glu Gly Pro Glu Glu Asn Ser Ala Tyr Glu Gln Leu Leu
                245                 250                 255
Ser Arg Leu Glu Glu Ile Ala Glu Glu Gly Ser Glu Thr Gln Val Pro
            260                 265                 270
Gly Leu Asp Ile Ser Ala Leu Leu Pro Ser Asp Phe Ser Arg Tyr Phe
            275                 280                 285
Gln Tyr Glu Gly Ser Leu Thr Thr Pro Cys Ala Gln Gly Val Ile
            290                 295                 300
Trp Thr Val Phe Asn Gln Thr Val Met Leu Ser Ala Lys Gln Leu His
305                 310                 315                 320
Thr Leu Ser Asp Thr Leu Trp Gly Pro Gly Asp Ser Arg Leu Gln Leu
                325                 330                 335
Asn Phe Arg Ala Thr Gln Pro Leu Asn Gly Arg Val Ile Glu Ala Ser
            340                 345                 350
Phe Pro Ala Gly Val Asp Ser Ser Pro Arg Ala Ala Glu Pro Val Gln
            355                 360                 365
Leu Asn Ser Cys Leu Ala Ala Gly Asp
            370                 375
```

<210> SEQ ID NO 8
<211> LENGTH: 20
<212> TYPE: PRT
<213> ORGANISM: Homo sapiens

```
<400> SEQUENCE: 8

Ile Leu Ala Leu Val Phe Gly Leu Leu Phe Ala Val Thr Ser Val Ala
1               5                   10                  15

Phe Leu Val Gln
            20

<210> SEQ ID NO 9
<211> LENGTH: 25
<212> TYPE: PRT
<213> ORGANISM: Homo sapiens

<400> SEQUENCE: 9

Met Arg Arg Gln His Arg Arg Gly Thr Lys Gly Gly Val Ser Tyr Arg
1               5                   10                  15

Pro Ala Glu Val Ala Glu Thr Gly Ala
            20                  25
```

CA IX-SPECIFIC INHIBITORS

This application is a continuation of U.S. application Ser. No. 11/222,986 (filed Sep. 8, 2005), now U.S. Pat. No. 7,833,734, which is a continuation-in-part of U.S. Ser. No. 10/723,795 (filed on Nov. 26, 2003), now U.S. Pat. No. 7,550,424, and this application claims priority from now abandoned U.S. Provisional Application No. 60/609,103 (filed on Sep. 9, 2004). Said U.S. Ser. No. 10/723,795 claims priority from U.S. Provisional Application Nos. 60/429,089 (filed on Nov. 26, 2002), 60/489,473 (filed on Jul. 22, 2003), and 60/515,104 (filed on Oct. 28, 2003). This application hereby declares priority under 35 USC §120 from the above-identified applications. The above priority applications and parent U.S. application Ser. No. 11/222,986 are hereby incorporated by reference.

REFERENCE TO SEQUENCE LISTING

The Sequence Listing, filed electronically and identified as USSN-11-929652-SEQ-LISTING, was created on Feb. 26, 2008, is 31.6 kb in size and is hereby incorporated by reference.

FIELD OF THE INVENTION

The present invention is in the general area of medical genetics and in the fields of chemistry, biochemical engineering, and oncology. More specifically, it relates to the use of organic and inorganic compounds, preferably aromatic and heterocyclic sulfonamides, to treat preneoplastic and/or neoplastic diseases by specifically inhibiting the carbonic anhydrase activity of the oncoprotein now known alternatively as the MN protein, the MN/CA IX isoenzyme, the MN/G250 protein or simply MN/CA IX or CA IX or MN. The present invention also relates to methods of treating preneoplastic and/or neoplastic diseases characterized by MN/CA IX overexpression by administering cell membrane-impermeant, inhibitors of MN/CA IX, preferably pyridinium derivatives of aromatic and heterocyclic sulfonamides. The invention further concerns diagnostic/prognostic methods including imaging methods, for preneoplastic/neoplastic diseases, using the disclosed potent CA IX-specific inhibitors, and gene therapy with vectors conjugated to said inhibitors.

BACKGROUND OF THE INVENTION

The instant inventors, Dr. Silvia Pastorekova and Dr. Jaromir Pastorek, with Dr. Jan Zavada ["Zavada et al."], discovered MN/CA IX, a cancer related cell surface protein originally named MN. [73, 123; Zavada et al., U.S. Pat. No. 5,387,676 (Feb. 7, 1995).] Zavada et al., WO 93/18152 (published 16 Sep. 1993) and Zavada et al., WO 95/34650 (published 21 Dec. 1995) disclosed the discovery of the MN gene and protein and the strong association of MN gene expression and tumorigenicity led to the creation of methods that are both diagnostic/prognostic and therapeutic for cancer and precancerous conditions. Zavada et al. disclosed further aspects of the MN/CA IX protein and the MN/CA9 gene in Zavada et al., WO 00/24913 (published 4 May 2000).

Zavada et al. cloned and sequenced the MN cDNA and gene, and revealed that MN belongs to a carbonic anhydrase family of enzymes that catalyze the reversible hydration of carbon dioxide to bicarbonate and proton [66, 72]. MN protein (renamed to carbonic anhydrase IX, CA IX) is composed of an extracellular part containing a N-terminal proteoglycan-like region and a catalytically active carbonic anhydrase domain. It is anchored in the plasma membrane by a single transmembrane region and a short intracytoplasmic tail.

Expression of CA IX is restricted to only few normal tissues [74], but is tightly associated with tumors [123]. It is also regulated by cell density in vitro [52] and is strongly induced by tumor hypoxia both in vitro and in vivo [121]. Numerous clinical papers describe the value of CA IX as an indicator of poor prognosis. All CA IX-related studies performed so far support the assumption made in the original Zavada et al., U.S. Pat. No. 5,387,676 that CA IX is useful as a diagnostic and/or prognostic tumor marker and as a therapeutic target.

MN/CA IX consists of an N-terminal proteoglycan-like domain that is unique among the CAs, a highly active CA catalytic domain, a single transmembrane region and a short intracytoplasmic tail [66, 72, 74, 116]. CA IX is particularly interesting for its ectopic expression in a multitude of carcinomas derived from cervix uteri, ovarian, kidney, lung, esophagus, breast, colon, endometrial, bladder, colorectal, prostate, among many other human carcinomas, contrasting with its restricted expression in normal tissues, namely in the epithelia of the gastrointestinal tract [8, 11, 21, 35, 41, 48, 50, 51, 56, 66, 72, 74, 86, 110, 111, 113, 116, 121, 122].

Uemura et al. [112] reported in 1997 that the G250 antigen was identical to MN/CA IX, years after MN/CA IX had been discovered and sequenced by Zavada et al. {[73, 123]; see also Pastorek et al. [72] and Opavsky et al. [66]}. Uemura et al. [112] stated: "Sequence analysis and database searching revealed that G250 antigen is identical to MN a human tumor-associated antigen identified in cervical carcinoma (Pastorek et al., 1994)."

MN/CA 9 and MN/CA IX—Sequence Similarities

FIG. 1A-C shows the full-length MN/CA9 cDNA sequence of 1522 base pairs (bps) [SEQ ID NO: 1], and the full-length MN/CA IX amino acid (aa) sequence of 459 aa [SEQ ID NO: 2]. FIG. 2A-F provides the 10,898 bp genomic sequence of MN/CA9 [SEQ ID NO: 3].

Computer analysis of the MN cDNA sequence was carried out using DNASIS and PROSIS (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [75].

The proteoglycan-like domain [aa 53-111; SEQ ID NO: 4] which is between the signal peptide and the CA domain, shows significant homology (38% identity and 44% positively) with a keratan sulphate attachment domain of a human large aggregating proteoglycan aggrecan [28].

The CA domain [aa 135-391; SEQ ID NO: 5] is spread over 265 aa and shows 38.9% amino acid identity with the human CA VI isoenzyme [5]. The homology between MN/CA IX and other isoenzymes is as follows: 35.2% with CA II in a 261 aa overlap [63], 31.8% with CA I in a 261 aa overlap [7], 31.6% with CA IV in a 266 aa overlap [65], and 30.5% with CA III in a 259 aa overlap [55].

In addition to the CA domain, MN/CA IX has acquired both N-terminal and C-terminal extensions that are unrelated to the other CA isoenzymes. The amino acid sequence of the C-terminal part, consisting of the transmembrane anchor and the intracytoplasmic tail, shows no significant homology to any known protein sequence.

The MN gene (MN/CA9 or CA9) was clearly found to be a novel sequence derived from the human genome. The overall sequence homology between the cDNA MN/CA9 sequence and cDNA sequences encoding different CA isoenzymes is in a homology range of 48-50% which is considered by ones in the art to be low. Therefore, the MN/CA9 cDNA sequence is not closely related to any CA cDNA sequences.

Very few normal tissues have been found to express MN protein to any significant degree. Those MN-expressing normal tissues include the human gastric mucosa and gallbladder epithelium, and some other normal tissues of the alimentary tract. Paradoxically, MN gene expression has been found to be lost or reduced in carcinomas and other preneoplastic/neoplastic diseases in some tissues that normally express MN, e.g., gastric mucosa.

CA IX, Hypoxia and Acidification of Extracellular Environment

Strong association between CA IX expression and intratumoral hypoxia (either measured by microelectrodes, or detected by incorporation of a hypoxic marker pimonidazole, or by evaluation of extent of necrosis) has been demonstrated in the cervical, breast, head and neck, bladder and non-small cell lung carcinomas (NSCLC) [8, 11, 21, 35, 48, 56, 111, 122]. Moreover, in NSCLC and breast carcinomas, correlation between CA IX and a constellation of proteins involved in angiogenesis, apoptosis inhibition and cell-cell adhesion disruption has been observed, possibly contributing to strong relationship of this enzyme to a poor clinical outcome [8]. Hypoxia is linked with acidification of extracellular milieu that facilitates tumor invasion and CA IX is believed to play a role in this process via its catalytic activity [86]. Thus, inhibition of MN/CA IX by specific inhibitors is considered to constitute a novel approach to the treatment of cancers in which CA IX is expressed.

Acidic extracellular pH (pHe) has been associated with tumor progression via multiple effects including up-regulation of angiogenic factors and proteases, increased invasion, and impaired immune functions [86, 124, 125, 130, 132]. In addition, it can influence the uptake of anticancer drugs and modulate the response of tumor cells to conventional therapy [86, 126]. Acidification of the tumor microenvironment was generally assigned to accumulation of lactic acid excessively produced by glycolysis and poorly removed by inadequate tumor vasculature. A high rate of glycolysis is especially important for hypoxic cells that largely depend on anaerobic metabolism for energy generation. However, experiments with glycolysis-deficient cells indicate that production of lactic acid is not the only mechanism leading to tumor acidity. The deficient cells produce only diminished amounts of lactic acid, but form acidic tumors in vivo [134, 144]. A comparison of the metabolic profiles of the glycolysis-impaired and parental cells revealed that $CO_2$, in addition to lactic acid, is a significant source of acidity in tumors [127]. That data indicates that carbonic anhydrases could contribute to the acidification of the tumor microenvironment.

The CA IX isoform is identified herein as the best candidate for the role in acidifying the tumor microenvironment. First, CA IX is an integral plasma membrane protein with an extracellularly exposed enzyme active site [66, 72]. Second, CA IX has a very high catalytic activity with the highest proton transfer rate among the known CAs [116]. Third, CA IX is present in few normal tissues, but its ectopic expression is strongly associated with many frequently occurring tumors. Finally, CA IX level dramatically increases in response to hypoxia via a direct transcriptional activation of CA9 gene by HIF-1 [121], and its expression in tumors is a sign of poor prognosis [136]. Taken together, CA IX is herein considered to have all the qualities necessary to control tumor pH. That concept is supported by the proof provided herein that CA IX has the capacity to acidify extracellular pH.

CAIs

Teicher et al. [106] reported that acetazolamide—the prototypical CA inhibitor (CAI)— functions as a modulator in anticancer therapies, in combination with different cytotoxic agents, such as alkylating agents; nucleoside analogs; platinum derivatives, among other such agents, to suppress tumor metastasis and to reduce the invasive capacity of several renal carcinoma cell lines (Caki-1, Caki-2, ACHN, and A-498). Such studies demonstrate that CAIs may be used in the management of tumors that overexpress one or more CA isozymes. It was hypothesized that the anticancer effects of acetazolamide (alone or in combination with such drugs) might be due to the acidification of the intratumoral environment ensuing after CA inhibition, although other mechanisms of action of this drug were not excluded [20]. Chegwidden et al. 2001 hypothesized that the in vitro inhibition of growth in cell cultures, of human lymphoma cells with two other potent, clinically used sulfonamide CAIs, methazolamide and ethoxzolamide, is probably due to a reduced provision of bicarbonate for nucleotide synthesis ($HCO_3^-$ is the substrate of carbamoyl phosphate synthetase II) as a consequence of CA inhibition [20].

All the six classical CAIs (acetazolamide, methazolamide, ethoxzolamide, dichlorophenamide, dorzolamide, and dichlorophenamide) used in clinical medicine or as diagnostic tools, show some tumor growth inhibitory properties [18, 78, 101, 102].

The inventors, Dr. Claudia Supuran and Dr. Andrea Scozzafava, reported the design and in vitro antitumor activity of several classes of sulfonamide CAIs, shown to act as nanomolar inhibitors against the classical isozymes known to possess critical physiological roles, such as CA I, CA II and CA IV. Those compounds were also shown to exert potent inhibition of cell growth in several leukemia, non-small cell lung, ovarian, melanoma, colon, CNS, renal, prostate and breast cancer cell lines, with $GI_{50}$ values of 10-75 nM in some cases [77, 91, 92, 100].

Wingo et al. reported that three classic sulfonamide drugs (acetozolamide, ethoxzolamide and methoxzolamide) inhibited CA IX carbonic anhydrase activity with values of $K_I$ in the nanomolar range [116]. However, until the present invention, no systematic structure-activity relationship study of sulfonamide inhibition of CA IX, alone or in comparison to other CA isozymes had been performed.

Certain pyridinium derivatives of aromatic/heterocyclic sulfonamides have shown nanomolar affinities both for CA II, as well as CA IV, and more importantly, they were unable to cross the plasma membranes in vivo [17].

Sterling et al. [85] investigated the functional and physical relationship between the downregulated in adenoma bicarbonate transporter and CA II, by using membrane-impermeant sulfonamide inhibitors (in addition to the classical inhibitors such as acetazolamide), which could clearly discriminate between the contribution of the cytosolic and membrane-associated isozymes in these physiological processes.

CAS

Carbonic anhydrases (CAs) form a large family of genes encoding zinc metalloenzymes of great physiological importance. As catalysts of reversible hydration of carbon dioxide, these enzymes participate in a variety of biological processes, including respiration, calcification, acid-base balance, bone resorption, formation of aqueous humor, cerebrospinal fluid, saliva and gastric acid [reviewed in Dodgson et al. (27)]. CAs are widely distributed in different living organisms. In higher vertebrates, including humans, 14 different CA isozymes or CA-related proteins (CARP) have been described, with very different subcellular localization and tissue distribution [40, 93, 95, 94, 102]. Basically, there are several cytosolic forms (CA I-III, CA VII), four membrane-bound isozymes (CA IV, CA IX, CA XII and CA XIV), one mitochondrial form (CA V) as well as a secreted CA isozyme, CA VI [40, 93, 94, 95, 102].

It has been shown that some tumor cells predominantly express only some membrane-associated CA isozymes, such as CA IX and CA XII [2, 67, 68, 78, 87, 93, 95]. Occasionally, nuclear localization of some isoenzymes has been noted [64, 69, 70]. Not much is presently known about the cellular localization of the other isozymes.

CAs and CA-related proteins show extensive diversity in their tissue distribution, levels, and putative or established biological functions [105]. Some of the CAs are expressed in almost all tissues (CA II), while the expression of others appears to be more restricted (e.g., CA VI and CA VII in salivary glands [32, 69, 71]. The CAs and CA-related proteins also differ in kinetic properties and susceptibility to inhibitors [82].

Most of the clinically used sulfonamides mentioned above are systemically acting inhibitors showing several undesired side effects due to inhibition of many of the different CA isozymes present in the target tissue/organ (14 isoforms are presently known in humans) [93, 94, 95, 102]. Therefore, many attempts to design and synthesize new sulfonamides were recently reported, in order to avoid such side effects [13, 17, 42, 62, 80, 99, 100]. At least four CA isozymes (CA IV, CA IX, CA XII and CA XIV) are associated to cell membranes, with the enzyme active site generally oriented extracellularly [93, 94, 95, 102]. Some of these isozymes were shown to play pivotal physiological roles (such as for example CA IV and XII in the eye, lungs and kidneys, CA IX in the gastric mucosa and many tumor cells) [3, 18, 22, 29, 49, 67, 68, 83, 93, 94, 95, 102], whereas the function of other such isozymes (CA XIV) is for the moment less well understood [93, 95]. Due to the extracellular location of these isozymes, if membrane-impermeant CA inhibitors (CAIs) could be designed, only membrane-associated CAs would be affected.

The first approach towards introducing the membrane-impermeability to CAIs from the historical point of view was that of attaching aromatic/heterocyclic sulfonamides to polymers, such as polyethyleneglycol, aminoethyldextran, or dextran [39, 60, 107]. Such compounds, possessing molecular weights in the range of 3.5-99 kDa, prepared in that way, showed indeed membrane-impermeability due to their high molecular weights, and selectively inhibited in vivo only CA IV and not the cytosolic isozymes (primarily CA II), being used in several renal and pulmonary physiological studies [39, 60, 107]. Due to their macromolecular nature, such inhibitors could not be developed as drugs/diagnostic tools, since in vivo they induced potent allergic reactions [39, 60, 93, 95, 107]. A second approach for achieving membrane-impermeability is that of using highly polar, salt-like compounds. Only one such sulfonamide has until recently been used in physiological studies, QAS (quaternary ammonium sulphanilamide), which has been reported to inhibit only extracellular CAs in a variety of arthropods (such as the crab *Callinectes sapidus*) and fish [57]. The main draw-back of QAS is its high toxicity in higher vertebrates [57].

Enzyme activity of carbonic anhydrases (including that of CA IX) can be efficiently blocked by sulfonamide inhibitors. That fact has been therapeutically exploited in diseases caused by excessive activities of certain CA isoforms (e.g. CA II in glaucoma). There is also an experimental evidence that sulfonamides may block tumor cell proliferation and invasion in vitro and tumor growth in vivo, but the targets of those sulfonamides have not been identified yet. However, the sulfonamides available so far indiscriminately inhibit various CA isoenzymes (14 are presently known in humans) that are localized in different subcellular compartments and play diverse biological roles. This lack of selectivity compromises the clinical utilization of these compounds (due to undesired side effects caused by concurrent inhibition of many CA isoforms) and represents a main drawback also for the sulfonamide application against CA IX in anticancer therapy.

Thus, there is a need in the art for membrane-impermeant, potent CA IX inhibitors, which would become doubly selective inhibitors for CA IX. The inventors have previously made and described some of the membrane-impermeant molecules described here; however, they were characterized only for their ability to inhibit CA I, CA II and CA IV. While others have studied effects of selective inhibition of extracellular CA by membrane impermeant agents in retinal pigmented epithelia or muscle [34, 120], these agents have not been characterized for their ability to inhibit CA IX. Since CA IX is one of the few extracellular carbonic anhydrases, a membrane-impermeant selective inhibitor of CA IX would be doubly selective for this enzyme and thereby avoid side effects associated with nonspecific CA inhibition.

SUMMARY OF THE INVENTION

The inventors have shown that MN/CA IX contributes to acidification of extracellular pH in hypoxia but not in normoxia. MN/CA IX-selective sulfonamides are shown to reduce the medium acidification and to bind only to hypoxic cells containing the wild type MN/CA IX. MN/CA IX's contributing to the acidification of the hypoxic extracellular milieu is considered to have important implications for the development of cancer. The disclosed experimental results indicate that hypoxia up-regulates both the expression level and enzyme activity of MN/CA IX, that is, hypoxia activates the CA catalytic activity of MN/CA IX. That is a very important finding because intratumoral hypoxia is a clinically relevant factor increasing aggressiveness of tumor cells and reducing success of therapy.

The invention concerns in one aspect diagnostic/prognostic and therapeutic methods for preneoplastic/neoplastic disease associated with abnormal MN/CA IX expression, comprising the use of MN/CA IX-specific inhibitors which bind preferentially to the activated form of the CA domain of MN/CA IX, and not to the inactive form of the CA domain of MN/CA IX. Preferred inhibitors according to the methods of the invention are activated MN/CA IX-specific inhibitors which are labeled, and which can be used to identify regions of hypoxic MN/CA IX expression, and not non-hypoxic MN/CA IX expression. Exemplary activated MN/CA IX-specific inhibitors include the sulfonamide Compounds 5, 6, 39 and 92, whose structures are shown in FIGS. 4A and 8A.

Further, MN/CA IX-specific inhibitors which are useful according to the methods of the invention may comprise any molecules that preferentially bind only the activated form of the CA domain of MN/CA IX, and not the inactive form of the CA domain of MN/CA IX. Such molecules may be organic or inorganic, preferably organic molecules. Such organic molecules may be sulfonamides or antibodies which selectively bind the activated form of the CA domain of MN/CA IX. Preferred organic molecules include monoclonal antibodies which specifically bind the activated form of the CA domain of MN/CA IX.

In one aspect, the invention concerns a diagnostic/prognostic method for a preneoplastic/neoplastic disease associated with abnormal MN/CA IX expression, comprising determining whether MN/CA IX is activated in a vertebrate sample, comprising a) contacting said sample with a specific inhibitor of activated MN/CA IX, and b) detecting or detecting and quantifying binding of said specific inhibitor of activated MN/CA IX in said sample; wherein binding of said inhibitor to said MN/CA IX indicates that said MN/CA IX is activated, preferably wherein said activated MN/CA IX is hypoxia-activated.

Preferably, said specific inhibitor of activated MN/CA IX is an MN/CA IX-specific sulfonamide or an MN/CA IX-specific antibody. Preferably said specific sulfonamide inhibitor of activated MN/CA IX is an aromatic sulfonamide or a heterocyclic sulfonamide. Alternatively, said sulfonamide specific inhibitor of activated MN/CA IX is a membrane-impermeant pyridinium derivative of an aromatic sulfonamide or a membrane-impermeant pyridinium derivative of a heterocyclic sulfonamide. Also preferably, said MN/CA IX-specific sulfonamide is selected from the group consisting of Compounds 1-92, whose structures are shown in Tables 2 and 3, and/or FIGS. 4 and 8A. Further preferably, said MN/CA IX-specific sulfonamide is selected from the group consisting of Compounds 5, 6, 39, or 92.

Said specific inhibitor of activated MN/CA IX can be conjugated to a label or a visualizing means, preferably fluorescein isothiocyanate, wherein said detecting or detecting and quantifying binding comprises detecting or detecting and quantifying said label or said visualizing means on cells in said sample, and wherein said detecting or said detecting and quantifying at a level above that for a control sample is indicative of hypoxic precancerous or cancerous cells that abnormally express activated MN/CA IX in said sample. Said method may further comprise detecting the binding of an antibody that specifically binds to a domain of the MN/CA IX protein other than the carbonic anhydrase domain.

Another exemplary method that is diagnostic or diagnostic and prognostic for precancer and/or cancer comprises contacting a mammalian sample with a MN/CA IX-specific inhibitor conjugated to a label or a visualizing means, and detecting or detecting and quantifying binding of said MN/CA IX-specific inhibitor to cells in said sample by detecting or detecting and quantifying said label or said visualizing means on cells in said sample, wherein said detection or said detection and quantitation at a level above that for a control sample is indicative of precancerous or cancerous cells that overexpress MN/CA IX in said sample. Such a method can be of particular diagnostic and prognostic importance by detecting or detecting and quantitating MN/CA IX activated by hypoxic conditions. Hypoxia combined with MN/CA IX overepression indicates that the mammal from whom the sample was taken is considered to have a poorer prognosis, and decisions on treatment for said mammal are made in view of the presence of said hypoxic conditions.

MN/CA IX as a hypoxia marker is useful in general in making therapeutic decisions. For example, a cancer patient whose tumor is known to express MN/CA IX at an abnormally high level would not be a candidate for certain kinds of chemotherapy and radiotherapy, but would be a candidate for hypoxia-selective chemotherapy.

In one embodiment of the invention, MN/CA IX-specific inhibitors are used in methods that aid in selecting patient therapy, for example, in a method wherein the inhibitor's binding to activated MN/CA IX is detectable at a level above that for a control sample, and hypoxia-selective therapy is selected. Preferably such hypoxia-selective therapy comprises the use of drugs that are toxic only under hypoxic conditions, for example, wherein the therapy comprises the use of tirapazamine or AQ4N. In another embodiment of the invention, the inhibitor's binding to activated MN/CA IX is not detectable at a level above that for a control sample, and the therapy consequently selected is radiotherapy and/or non-hypoxia-selective chemotherapy.

In another aspect, the invention concerns a method of imaging hypoxic tissues in a patient, comprising a) administering to said patient a specific inhibitor of activated MN/CA IX, said inhibitor linked to an imaging agent; and b) detecting the binding of said inhibitor. Said specific inhibitor of activated MN/CA IX is preferably an MN/CA IX-specific sulfonamide or an MN/CA IX-specific antibody. More preferably, said MN/CA IX-specific sulfonamide is an aromatic or a heterocyclic sulfonamide, and said MN/CA IX-specific antibody is a monoclonal antibody.

Still another aspect of the invention concerns a method of therapy for a preneoplastic/neoplastic disease associated with hypoxic tissues, comprising administering a specific inhibitor of activated MN/CA IX, preferably an MN/CA IX-specific sulfonamide. Preferably, said specific inhibitor of activated MN/CA IX is an aromatic sulfonamide or a heterocyclic sulfonamide. Alternatively, said specific inhibitor of activated MN/CA IX is preferably a membrane-impermeant pyridinium derivative of an aromatic sulfonamide or a membrane-impermeant pyridinium derivative of a heterocyclic sulfonamide. More preferably, said MN/CA IX-specific sulfonamide is selected from the group consisting of Compounds 1-92. Most preferably, said MN/CA IX-specific sulfonamide is selected from the group consisting of Compounds 5, 6, 39, or 92.

Said specific inhibitor of activated MN/CA IX can also be an MN/CA IX-specific antibody, alone or conjugated to a toxic and/or cytostatic agent; preferably said MN/CA IX-specific antibody is a monoclonal antibody.

In another embodiment of the invention, the method of therapy comprises the use of a specific inhibitor of activated MN/CA IX conjugated to a vector comprising a gene that expresses a cytotoxic protein. Said vector may further comprise a MN/CA9 promoter or MN/CA9 promoter fragment, and/or one or more hypoxia response elements.

In still another embodiment of the invention, the method of therapy comprises the use of a specific inhibitor of activated MN/CA IX to modulate the efficiency of chemotherapeutic drugs whose uptake or activity is pH-dependent.

The instant invention is related to (1) the recognition that certain carbonic anhydrase inhibitors (CAIs), preferably sulfonamides, selectively target the cancer-related, hypoxia-induced MN/CA IX; (2) the use of such CAIs, preferably sulfonamides, as lead compounds for the design and synthesis of MN/CA IX-specific inhibitors; (3) the employment of said MN/CA IX-specific inhibitors for anticancer therapy based upon the inhibition of MN/CA IX-mediated acidification of tumor microenvironments; and (4) the use of the specificity of potent MN/CA IX-specific inhibitors for diagnostic/prognostic methods including imaging methods, such as scintigraphy, and for gene therapy. The invention is particularly directed to the use of MN/CA IX-specific inhibitors for the development of drugs possessing anticancer properties and to modulate conventional chemotherapy for preneoplastic and neoplastic disease characterized by MN/CA IX expression, particularly MN/CA IX overexpression.

In one aspect, the invention concerns methods of treating a mammal for a pre-cancerous or cancerous disease, wherein said disease is characterized by overexpression of MN/CA IX protein, comprising administering to said mammal a therapeutically effective amount of a composition comprising a compound, wherein said compound is selected from the group consisting of organic and inorganic molecules, and wherein said compound is determined to be a potent inhibitor of MN/CA IX enzymatic activity in a screening assay to determine the $K_I$ of a compound inhibiting the enzymatic activity of MN/CA IX, wherein if said inhibition constant $K_I$ is determined to be less than about 50 nanomolar, said compound is determined be a potent inhibitor of MN/CA IX enzymatic activity; and wherein said compound is not selected from the group consisting of acetazolamide, ethoxzolamide, methazolamide and cyanate. Said mammal is preferably human, and said $K_I$ is preferably less than about 35 nanomolar, more preferably less than about 25 nanomolar, and still more preferably less than about 10 nanomolar. Exemplary enzymatic screening assays that can be used to determine the K, of a compound inhibiting the enzymatic activity of MN/CA IX are described below under "Enzyme Assays" in the *Materials and Methods* section, and also described in references cited in Table 1, which are hereby incorporated by reference.

Such methods can also be framed as methods of treating precancer and/or cancer, or inhibiting the growth of precancerous and/or cancerous cells in a mammalian subject, wherein said precancer and cancer are characterized by the overexpression of MN/CA IX. Said methods can also be framed as inhibiting the growth of such precancerous or cancerous mammalian cells overexpressing MN/CA IX comprising contacting said cells with a MN/CA IX-specific inhibitor of this invention.

The MN/CA IX-specific inhibitors of this invention can be administered in a therapeutically effective amount, preferably dispersed in a physiologically acceptable nontoxic liquid vehicle. Different routes of administration may be preferred depending on the site or type of preneoplastic/neoplastic disease, for example, solid or non-solid tumor or metastasis. In general, parenteral administration would be preferred to avoid undesired effects of systemic treatment, for example, those that could be occasioned by binding of the inhibitors to the gastrointestinal mucosa. Injection into or into the vicinity of the preneoplastic/neoplastic disease would be generally preferred. For example, such injections could be intravenous, intraperitoneal, rectal, subcutaneous, intramuscular, intraorbital, intracapsular, intraspinal, intrasternal, intramedullary, intralesional, intradermal, among other routes of injection. Also, other modes of administration, for example, by suppository or topically, can be used as would be appropriate to the target disease. The pharmaceutical formulation would be designed in accordance with known standards as suitable for the route of administration.

Said MN/CA IX-specific inhibitors are preferably organic, more preferably aromatic or heterocyclic, and still more preferably an aromatic sulfonamide or a heterocyclic sulfonamide. Said aromatic sulfonamide may be a substituted aromatic sulfonamide, wherein said aromatic sulfonamide comprises an aromatic ring structure bearing a sulfonamide moiety bonded to said ring structure and optionally bearing one or more substituents independently selected from the group consisting of halogeno, nitro, and an alkylamino group, wherein the alkyl radical of said alkylamino group comprises 1 to 4 carbon atoms.

Preferably the MN/CA IX-specific inhibitors of this invention are more potent inhibitors of MN/CA IX enzymatic activity than of the enzymatic activity of a carbonic anhydrase selected from the group consisting of CA I, CA II and CA IV. More preferably, the MN/CA IX-specific inhibitors are more potent inhibitors of MN/CA IX enzymatic activity than of the enzymatic activity of at least two carbonic anhydrases selected from the group consisting of CA I, CA II and CA IV. Still more preferably, the MN/CA IX-specific inhibitors are more potent inhibitor of MN/CA IX enzymatic activity than of the enzymatic activity of each of the carbonic anhydrases in the group consisting of CA I, CA II and CA IV.

However, since CA II is a particularly abundant and significant CA, that is cytosolic, it is important when the MN/CA IX-specific inhibitors of this invention are not membrane-impermeant, that they may be more potent inhibitors of MN/CA IX enzymatic activity than of the enzymatic activity of CA II. Exemplary enzymatic screening assays to determine the $K_I$ of CA II inhibitors are described below under "Enzyme Assays" in the *Materials and Methods* section, and also described in references cited in Table 1, which are hereby incorporated by reference.

Exemplary and preferred aromatic sulfonamide or heterocyclic sulfonamide MN/CA IX-specific inhibitors of this invention are selected from the group consisting of Compounds 1-26 shown in FIG. 4, and their FITC-derivatives. Exemplary preferred aromatic sulfonamide MN/CA IX-specific aromatic sulfonamides are Compounds 1, 6, and 23-26. A preferred aromatic sulfonamide MN/CA IX-specific inhibitor can be that wherein a halogen atom is bonded to at least one carbon atom in the aromatic ring of said aromatic sulfonamide. Particularly preferred aromatic sulfonamide MN/CA IX-specific inhibitors are selected from the group consisting of Compounds 5 and 6, and the FITC-derivative of Compound 5, Compound 92 (whose structure is shown in FIG. 8A). Particularly preferred heterocyclic sulfonamide MN/CA IX-specific inhibitors are Compounds 14, 15, 21 and 22.

Preferred heterocyclic sulfonamide MN/CA IX-specific inhibitors can be substituted heterocyclic sulfonamides, wherein said substituted heterocyclic sulfonamide comprises a heterocyclic ring structure bearing a sulfonamide moiety bonded to said ring structure and optionally bearing one or more substituents independently selected from a group consisting of halogeno, nitro, and an alkylamino group, wherein the alkyl radical of said alkylamino group comprises 1 to 4 carbon atoms. Preferred heterocyclic sulfonamide MN/CA IX-specific inhibitors may be halogenated.

Further preferred methods of treating mammals for precancerous or cancerous disease, wherein said disease is characterized by overexpression of MN/CA IX protein, comprise administering to said mammal membrane-impermeant MN/CA IX-specific inhibitors. A therapeutically effective amount of such a membrane-impermeant MN/CA IX-specific inhibitor can be administered in a composition comprising the membrane-impermeant compound, wherein said membrane-impermeant inhibitor compound is selected from the group consisting of organic and inorganic molecules, and wherein said membrane-impermeant compound is determined to be a potent inhibitor of MN/CA IX enzymatic activity in a screening assay.

Such a membrane-impermeant MN/CA IX specific inhibitor compound is preferably organic, and more preferably a pyridinium derivative of an aromatic sulfonamide or a pyridinium derivative of a heterocyclic sulfonamide. Such membrane-impermeant MN/CA IX-specific inhibitor compounds are preferably more potent inhibitors of MN/CA IX enzymatic activity than of the enzymatic activity of a carbonic anhydrase selected from the group consisting of CA I, CA II and CA IV, and still more preferably more potent inhibitors of MN/CA IX enzymatic activity than of the enzymatic activity of at least two carbonic anhydrases selected from the group consisting of CA I, CA II and CA IV. Further more preferably, said membrane-impermeant MN/CA IX-specific inhibitor compounds are more potent inhibitors of MN/CA IX enzymatic activity than of the enzymatic activity of each of the carbonic anhydrases in the group consisting of CA I, CA II and CA IV. Since both MN/CA IX and CA IV are membrane bound CAs, it is particularly important that the membrane-impermeant MN/CA IX-specific inhibitor compounds are more potent inhibitors of MN/CA IX enzymatic activity than of the enzymatic activity of CA IV.

Exemplary enzymatic screening assays that can be used to determine the $K_I$ of a compound inhibiting the enzymatic activity of CA IV are described below under "Enzyme Assays" in the *Materials and Methods* section, and also in references cited in Table 1, which are hereby incorporated by reference.

Preferred membrane-impermeant MN/CA IX-specific inhibitor compounds that are pyridinium derivatives of aromatic sulfonamides are selected from the group consisting of sulfanilamide, homosulfanilamide and 4-aminoethyl-benzenesulfonamide. Preferred pyridinium derivatives of aromatic sulfonamides can have the general formula of:

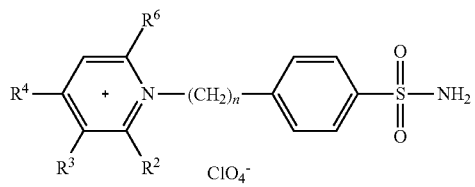

wherein
n is 0, 1, or 2;
R2, R3, R4 and R6 are each independently selected from the group consisting of hydrogen, alkyl moieties comprising from 1 to 12 carbon atoms, and aryl moieties. Further preferred pyridinium derivatives of aromatic sulfonamides are Compounds 27-70 shown in Table 2. Exemplary preferred pyridinium derivatives of aromatic sulfonamides are Compounds 39, 55, 58, 59 and 70. Particularly preferred is Compound 39 shown in Table 2 and FIG. 8A.

When said MN/CA IX-specific inhibitors are membrane-impermeant pyridinium derivatives of a heterocyclic sulfonamides, a preferred compound is a pyridinium derivative of aminobenzolamide.

Preferred MN/CA IX-specific inhibitor compounds that are pyridinium derivatives of heterocyclic sulfonamides may have the general formula of:

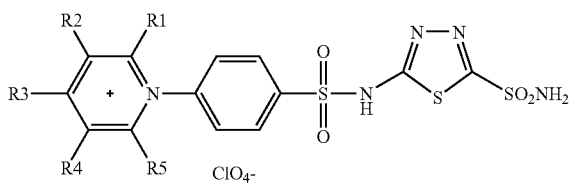

wherein R1, R2, R3, R4 and R5 are each independently selected from the group consisting of hydrogen, alkyl moieties comprising from 1 to 12 carbon atoms, and aryl moieties. Further preferred pyridinium derivatives of heterocyclic sulfonamides are Compounds 71-91 shown in Table 3.

In another aspect, this invention concerns methods of inhibiting tumor growth in a patient having a tumor, the cells of which tumor are characterized by overexpression of MN/CA IX protein, comprising administering to said patient a therapeutically effective amount of a composition comprising a compound, wherein said compound is selected from the group consisting of organic and inorganic molecules, and wherein said compound is determined to be a potent inhibitor of MN/CA IX enzymatic activity in a screening assay as outlined above.

In another therapeutic aspect of the invention, the MN/CA IX-specific inhibitors can be conjugated to radioisotopes for administration. Also, the MN/CA IX-specific inhibitors can be administered concurrently and/or sequentially with radiation and/or with a therapeutically effective amount in a physiologically acceptable formulation of one or more of the following compounds selected from the group consisting of: conventional anticancer drugs, chemotherapeutic agents, different inhibitors of cancer-related pathways, bioreductive drugs, MN/CA IX-specific antibodies and MN/CA IX-specific antibody fragments that are biologically active. Preferably said MN/CA IX-specific antibodies and/or MN/CA IX-specific antibody fragments are humanized or fully human, and may be attached to a cytotoxic entity.

In another therapeutic aspect, this invention concerns methods of treating a mammal for a precancerous or cancerous disease, wherein said disease is characterized by overexpression of MN/CA IX protein, comprising administering to said mammal a therapeutically effective amount in a physiologically acceptable formulation of a vector conjugated to a potent MN/CA IX-specific inhibitor, wherein said vector expresses a wild-type gene that is absent from or mutated in a MN/CA IX expressing cell, that is precancerous or cancerous, and wherein the wild type gene product has an anticancer effect in said cell; or wherein said vector comprises a gene that expresses a cytotoxic protein. An exemplary wild-type gene would be the von Hippel-Lindau gene known to be directly involved in the constitutive expression of MN/CA IX in renal cell carcinoma.

Preferably said vector comprises a MN/CA IX promoter or a MN/CA IX promoter fragment, wherein said promoter or promoter fragment comprises one or more hypoxia response elements (HREs), and wherein said promoter or promoter fragment is operably linked to said wild-type gene or to said gene that expresses a cytotoxic protein. Preferably the MN/CA IX-specific inhibitor conjugated to the vector has a $K_I$ as determined in a $CO_2$ saturation assay to be less than about 50 nM, more preferably less than about 35 nM, still more preferably less than about 25 nM and still further more preferably less than about 10 nM. Preferably, said potent MN/CA IX inhibitor is not selected from the group consisting of acetazolamide, ethoxzolamide, methazolamide and cyanate.

Brown, J. M. [16] points out at page 157 that "solid tumours are considerably less well oxygenated than normal tissues. This leads to resistance to radiotherapy and anticancer chemotherapy, as well as predisposing to increased tumour metastases." Brown explains how tumor hypoxia can be exploited in cancer treatment. One strategy to exploit tumor hypoxia for cancer treatment proposed by Brown [16] is to use drugs that are toxic only under hypoxic conditions. Exemplary and preferred drugs that could be used under that strategy include tirapazamine and AQ4N, a di-N-oxide analogue of mitozantrome.

A second mode of exploiting hypoxia proposed by Brown [16] is by gene therapy strategies developed to take advantage of the selective induction of is HIF-1. Brown notes that a tumor-specific delivery system can be developed wherein a promoter that is highly responsive to HIF-1 would drive the expression of a conditionally lethal gene under hypoxic but not normoxic conditions. The MN/CA IX promoter is just such a promoter highly responsive to hypoxia, as well as MN/CA IX promoter fragments comprising one or more HREs. "Expression of an enzyme not normally found in the human body could, under the control of a hypoxia-responsive promoter [the MN/CA IX promoter], convert a nontoxic prodrug into a toxic drug in the tumour." [Brown [16], page 160.] Exemplary is the use of the bacterial cytosine deaminase, which converts the nontoxic 5-fluorocytosine to the anticancer drug 5-fluorouracil (5FU) cited by Brown to Trinh et al. [109].

Ratcliffe et al., U.S. Pat. Nos. 5,942,434 and 6,265,390 explain how anti-cancer drugs become activated under hypoxia [119], but that the use of a drug activation system, wherein the enzyme that activates the drug is significantly increased under hypoxia, results in much enhanced therapeutic effect.

This invention further concerns methods for imaging tumors and/or metastases that express MN/CA IX in a patient comprising the administration of a MN/CA IX-specific inhibitor linked to an imaging agent to said patient. A preferred imaging method would encompass scintigraphy.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

The present invention is useful for treating and for screening the presence of a wide variety of preneoplastic/neoplastic diseases including carcinomas, such as, mammary, colorectal, urinary tract, ovarian, uterine, cervical, endometrial, squamous cell and adenosquamous carcinomas; head and neck cancers; mesodermal tumors, such as, neuroblastomas and retinoblastomas; sarcomas, such as osteosarcomas and Ewing's sarcoma; and melanomas. Of particular interest are gynecological cancers including ovarian, uterine, cervical, vaginal, vulval and endometrial cancers, particularly ovarian, uterine cervical and endometrial cancers. Also of particular interest are cancers of the breast, of gastrointestinal tract, of the stomach including esophagus, of the colon, of the kidney, of the prostate, of the liver, of the urinary tract including bladder, of the lung, and of the head and neck. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen can be detected and/or quantitated using a number of well-defined diagnostic assays. Those in the art can adapt any of the conventional immunoassay formats to detect and/or quantitate MN antigen as herein disclosed. The immunoassays of this invention can be embodied in test kits which comprise the potent MN/CA IX-specific inhibitors of this invention, appropriately labeled and/or linked to a visualizing means, as known in the art. Such test kits can be in solid phase formats, but are not limited thereto, and can also be in liquid phase format, and can be based on immunohistochemical assays, ELISAS, particle assays, radiometric or fluorometric assays either unamplified or amplified, using, for example, avidin/biotin technology, among other assay formats.

Exemplary MN/CA IX-specific inhibitors of the invention are shown herein to treat transfected cells that constitutively express MN/CA IX compared to non-transfected cells with no MN/CA IX expression. The exemplary MN/CA IX-specific inhibitors are shown to inhibit acidification of extracellular pH induced by MN/CA IX in cell cultures exposed to hypoxia.

Further, labeled exemplary MN/CA IX-specific inhibitors, such as labeled sulfonamides, for example, conjugated to fluorescein isothiocyanate (FITC), are shown to bind to the surface of MN/CA IX transfected cells, and not to control cells, only in hypoxia but not in normoxia. Those experiments confirm that MN/CA IX-specific inhibitors, such as the sulfonamide compounds described herein, can specifically target MN/CA IX under conditions characteristic of intratumoral microenvironments.

The MN/CA IX-specific inhibitors of this invention can be used diagnostically and prognostically for precancer and cancer, and to determine the status of a patient, and therapeutically, individually or in different combinations with conventional therapeutic regimens to treat precancers and/or cancer. The MN/CA IX-specific inhibitors may also be used in cancer research.

More particularly for treating precancer and/or cancer, the MN/CA IX-specific inhibitors of this invention can be used to hinder cancer expansion and/or progression by blocking MN/CA IX activity. The MN/CA IX-specific inhibitors can be conjugated to radioisotopes for radiotherapy. The MN/CA IX-specific inhibitors can be combined with MN/CA IX-specific antibodies and a variety of conventional therapeutic drugs, different inhibitors of cancer-related pathways, bioreductive drugs, and/or radiotherapy, wherein different combinations of treatment regimens with the MN/CA IX-specific inhibitors of this invention may increase overall treatment efficacy. Particularly, the MN/CA IX-specific inhibitors of this invention may be combined with therapy using MN/CA IX-specific antibodies and/or MN/CA IX-specific antibody fragments, preferably humanized MN/CA IX-specific antibodies and/or biologically active fragments thereof, and more preferably fully human MN/CA IX-specific antibodies and/or fully human MN/CA IX-specific biologically active antibody fragments. Said MN/CA IX-specific antibodies and biologically active MN/CA IX-specific antibody fragments, preferably humanized and more preferably fully human, may be conjugated to a cytotoxic entity, for example, a cytotoxic protein, such as ricin A, among many other cytotoxic entities.

Still further, a MN/CA IX-specific inhibitor of this invention could be coupled to a vector for targeted delivery to MN/CA IX-specific expressing cells for gene therapy (for example, with the wild-type von Hippel-Lindau gene), or for effecting the expression of cytotoxic proteins, preferably wherein said vector comprises a MN/CA IX promoter or MN/CA IX promoter fragment comprising the MN/CA IX hypoxia response element (HRE) or a HRE of another gene, and more preferably wherein the MN/CA IX promoter or MN/CA IX promotor fragment comprises more than one HRE, wherein said HRE or HREs is or are either of MN/CA IX, and/or of other genes and/or of genetically engineered HRE consensus sequences in a preferred context.

Particularly, the MN/CA IX-specific inhibitors of this invention can be used diagnostically/prognostically to detect precancerous and/or cancerous cells by binding to MN/CA IX, preferably to MN/CA IX activated by hypoxic conditions, wherein said MN/CA IX specific inhibitors are coupled to a label or to some visualizing means. Such detection, particularly of hypoxic conditions, and MN/CA IX overexpression, can be helpful in determining effective treatment options, and in predicting treatment outcome and the prognosis of disease development. Further the MN/CA IX-specific inhibitors when labeled or linked to an appropriate visualizing means can be used for imaging tumors and/or metastases that express MN/CA IX.

The MN/CA IX-specific inhibitors of this invention can also be used in basic and pre-clinical research. For example, the MN/CA IX-specific inhibitors can be used to study the regulation of MN/CA IX enzyme activity, to study the role of MN/CA IX in tumor growth and metabolism, and to study the role of MN/CA IX in response to treatment by drugs, radiation, inhibitors and other therapeutic regimens.

Further provided are screening assays for compounds that are useful for inhibiting the growth of a vertebrate, preferably mammalian, more preferably human, preneoplastic or neoplastic cell that abnormally expresses MN protein. Said screening assays comprise tests for the inhibition of the enzymatic activity of MN by said compounds. Additional assays provided herein test said compounds for their cell membrane impermeance.

Aspects of the instant invention disclosed herein are described in more detail below.

REFERENCES

The following references are cited throughout the application by numbers in italics keyed to the list below:
1. Abbate et al., *J. Med. Chem.*, 45: 3583-3587 (2002).
2. Abbate et al., *J. Enz. Inhib. Med. Chem.*, 18: 303-308 (2003a).
3. Abbate et al., *Bioorg. Med. Chem. Lett.*, 13: In Press (2003b).
4. Abdine et al., *J. Assoc. Off. Anal. Chem.*, 61: 695-701 (1978).
5. Aldred et al., *Biochemistry*, 30: 569-575 (1991).
6. Balaban et al., "Pyrylium Salts: Syntheses, Reactions and Physical Properties," In *Advances in Heterocyclic Chemistry*, Katritzky, A. R., Ed., Academic Press, New York, pp. 8-360 (1982).
7. Barlow et al., *Nucl. Acids Res.*, 15: 2386 (1987).
8. Bartosova et al., *J. Pathol.*, 197: 314-321 (2002).
9. Bayer, A., *Ber. Dtsch. Chem. Ges.*, 43: 2337-2349 (1910).
10. Bayer and Piccard, Liebigs *Ann. Chem.*, 384: 208-223 (1911).
11. Beasley et al., *Cancer Res.*, 61: 5262-5267 (2001).
12. Behravan et al., *Eur. J. Biochem*, 190: 351-357 (1990).
13. Borras et al., *Bioorg. Med. Chem.*, 7: 2397-2406 (1999).
14. Briganti et al., *Biochemistry*, 36: 10384-10392 (1997).
15. Briganti et al., *Inorg. Chim. Acta.*: 275-276, 295-300 (1998).
16. Brown, J. M., "Exploiting the hypoxic cancer cell: mechanisms and therapeutic strategies," *Molecular Medicine Today*, 6: 157-162 (April 2000).
17. Casini et al., *J. Med. Chem.*, 43: 488-44892 (2000).
18. Casini et al., *Curr. Cancer Drug Targets*, 2: 55-75 (2002).
19. a) Casini et al., *Bioorg. Med. Chem. Lett*, 13: 841-845 (2003).
    b) Casini et al., *Biorg. Med. Chem. Lett.*, 13: 2763-2769 (2003).
20. Chegwidden et al., "The Roles of carbonic anhydrase isozymes in cancer," *Gene Families Studies of DNA, RNA, Enzymes and Proteins*, Xue et al., Eds., World Scientific, Singapore, pp. 157-169 (2001).
21. Chia et al., *J. Clin. Oncol.*, 19: 3660-3668 (2001).
22. Chirica et al., *Biochim. Biophys. Acta.*, 1544: 55-63 (2001).
23. Clare and Supuran, *Eur. J. Med., Chem.*: 32: 311-319 (1997).
24. Clare and Supuran, *Eur. J. Med. Chem.*, 34: 463-474 (1999).
25. Cuthbert et al., *J. Physiol.*, 551 (Pt. 1) 79-92, (2003).
26. Dinculescu and Balaban, *Rev. Roum. Chem.*, 25: 1505-1528 (1980).
27. Dodgson et al., *The Carbonic Anhydrases*, Plenum Press, New York-London, pp. 398 (1991).
28. Doege et al., *J. Biol. Chem.*, 266: 894-902 (1991).
29. Elleby et al., *Eur. J. Biochem.*, 268: 1613-1619 (2001).
30. Ferraroni et al., Biochemistry, 41: 6237-6244 (2002a).
31. Ferraroni et al., Inorg. Chim. Acta, 339: 135-144 (2002b).
32. Fleming et al., *J. Clin. Invest.*, 96: 2907-2913 (1995).
33. Franchi et al., *J. Enz. Inhib. Med. Chem.*, 18: 333-338 (2003).
34. Geers and Gros, *Physiol. Rev.* 80:681-715 (2000).
35. Giatromanolaki et al., *Cancer Res.*, 61: 7992-7998 (2001).
36. Gomaa, Z. S., *Biomed. Chromatogr.*, 7: 134-135 (1993).
37. Gruneberg et al., *Angew. Chem. Int. Ed.*, 40: 389-393 (2001).
38. Hakansson et al., *J. Mol. Biol.*, 227: 1192-1204 (1992).
39. Heming et al., *J. Appl. Physiol.*, 61: 1849-1856 (1986).
40. Hewett-Emmett, D., "Evolution and distribution of the carbonic anhydrase gene families," In *The Carbonic Anhydrases—New Horizons*, Chegwidden et al., Eds., Birkhauser Verlag: Basel, Switzerland, pp. 29-78 (2000).
41. Höckel and Vaupel, *J. Natl. Cancer Inst.*, 93: 266-276 (2001).
42. Ilies et al., *Bioorg. Med. Chem.*, 8: 2145-2155 (2000).
43. Ilies et al., *J. Med. Chem.*, 46: 2187-2196 (2003).
44. Khalifah, R. G., *J. Biol. Chem.*, 246: 2561-2573 (1971).
45. Khalifah et al., *Biochemistry*, 16: 2241-2247 (1977).
46. Kim et al., *J. Am. Chem. Soc.*, 122: 12125-12134 (2000).
47. Kim et al., *J. Am. Chem. Soc.*, 123: 9620-9627 (2001).
48. Koukourakis et al., *Clin. Cancer Res.*, 7: 3399-3403 (2001).
49. Krungkrai et al., *Int. J. Parasitol.*, 31: 661-668 (2001).
50. Liao et al., *Am. J. Pathol.*, 145: 598-609 (1994).
51. Liao et al., *Cancer Res.*, 57: 2827-2831 (1997).
52. Lieskovska et al., *Neoplasma*, 46: 17-24 (1999).
53. Lindskog and Coleman, *Proc. Natl. Acad. Sci.* (USA) 70: 2505-2508 (1964).
54. Lindskog et al., "Structure-function relations in human carbonic anhydrase II as studied by site-directed mutagenesis," in *Carbonic anhydrase—From biochemistry and genetics to Physiology and clinical medicine*, Botre et al., Eds., VCH, Weinheim, pp. 1-13 (1991)].
55. Lloyd et al., *Genes. Dev.*, 1: 594-602 (1987).
56. Loncaster et al., *Cancer Res.*, 61: 6394-6399 (2001).

57. Maren, T. H., *Physiol. Rev.*, 47: 595-781 (1967).
58. Maren, T. H., "Benzolamide—a renal carbonic anhydrase inhibitor," In *Orphan Drugs*, Karch, T. E., Ed., M. Dekker, New York, pp. 89-115 (1982).
59. Maren et al., *Mol. Pharmacol.*, 44: 901-906 (1993).
60. Maren et al., *J. Pharmacol. Exp. Ther.*, 280: 98-104 (1997).
61. Mendelsohn and Lippman, "Growth Factors," pp. 114-133, IN: DeVita et al. (eds.), *Cancer: Principles and Practice of Oncology* (4$^{th}$ Ed.; Lippincott; Philadelphia, 1993).
62. Mincione et al., *Eur. J. Pharm. Sci.*, 9: 185-199 (1999).
63. Montgomery et al., *Nucl. Acids. Res.*, 15: 4687 (1987).
64. Mori et al., *Gastroenterol.*, 105: 820-826 (1993).
65. Okuyama et al., *PNAS* (USA) 89: 1315-1319 (1992).
66. Opavsky et al., *Genomics*, 33: 480-487 (1996).
67. Owa and Nagasu, *Exp. Opin. Ther. Patents*, 10: 1725-1740 (2000).
68. Owa et al., *J. Med. Chem.*, 42: 3789-3799 (1999).
69. Parkkila et al., *Gut*, 35: 646-650 (1994).
70. Parkkilla et al., *Histochem. J.*, 27: 133-138 (1995).
71. Parkkila et al., *Hepatology*, 24: 104 (1996).
72. Pastorek et al., *Oncogene*, 9: 2788-2888 (1994).
73. Pastorekova et al., *Virology*, 187: 620-626 (1992).
74. Pastorekova et al., *Gastroenterology*, 112: 398-408 (1997).
75. Pearson and Lipman, *PNAS* (USA), 85: 2444 (1988).
76. Pocker and Stone, *Biochemistry*, 6: 668-678 (1967).
77. Scozzafava and Supuran, *Bioorg. Med. Chem. Lett.*, 10: 1117-1120 (2000).
78. Scozzafava et al., *Curr. Med. Chem.*, 10: 925-953 (2003).
79. Scozzafava et al., *J. Med. Chem.*, 42: 2641-2650 (1999).
80. Scozzafava et al., *J. Med. Chem.*, 42: 3690-3700 1999)
81. Scozzafava et al., *J. Med. Chem.*, 43: 292-300 (2000).
82. Sly and Hu, *Annu. Rev. Biochem.*, 64: 375-401 (1995).
83. Smith and Ferry, *FEMS Microbiol. Rev.*, 24: 335-366 (2000).
84. Steiner et al., *Eur. J. Biochem.*, 59: 253-259 (1975).
85. Sterling et al., *Am. J. Physiol.—Cell Physiol.*, 283: C1522-C1529 (2002).
86. Stubbs et al., *Mol. Med. Today*, 6: 15-19 (2000).
87. Supuran, C. T., *Opin. Investig. Drugs*, 12: 283-287 (2003).
88. Supuran and Clare, *Eur. J. Med. Chem.*, 30: 687-696 (1995).
89. Supuran and Clare, *Eur. J. Med. Chem.*, 33: 489-500 (1998).
90. Supuran and Clare, *Eur. J. Med. Chem.*, 34: 41-50 (1999).
91. Supuran and Scozzafava, *J. Enzyme Inhib.*, 15: 597-610 (2000a).
92. Supuran and Scozzafava, *Eur. J. Med. Chem.*, 35: 867-874 (2000b).
93. Supuran and Scozzafava, *Exp. Opin. Ther. Patents*, 10: 575-600 (2000c).
94. Supuran and Scozzafava, *Curr. Med. Chem.—Imm., Endoc. Metab. Agents*, 1: 61-97 (2001).
95. Supuran and Scozzafava, *Exp. Opin. Ther. Patents*, 12: 217-242 (2002).
96. Supuran et al., *Eur. J. Med. Chem.*, 33: 577-594 (1998a).
97. Supuran et al., *Eur. J. Med. Chem.*, 33: 739-752 (1998b).
98. Supuran et al., *J. Enz. Inhib.*, 15: 381-401 (2000a).
99. Supuran et al., *J. Med. Chem.*, 35: 309-321 (2000b).
100. Supuran et al., *Bioorg. Med. Chem.*, 9: 703-714 (2001a).
101. Supuran et al., *Curr. Med. Chem.—Imm. Endoc. Metab. Agents*, 1: 61-97 (2001b)
102. Supuran et al., *Med. Res. Rev.*, 23: 146-189 (2003).
103. Svastova et al., *Experimental Cell Research*, 290: 332-345, (2003).
104. Symington, *J. Biol. Chem.*, 267: 25744 (1992).
105. Tashian, R. E., *Adv. in Genetics*, 30: 321-356 (1992).
106. Teicher et al., *Anticancer Research*, 13: 1549-1556 (1993).
107. Tinker et al., *J. Pharmacol. Exp. Ther.*, 218: 600-607 (1981).
108. Toma and Balaban, *Tetrahedron, Suppl.* 7: 27-34 (1966).
109. Trinh et al., *Cancer Res.*, 55: 4808-4812 (1995).
110. Turner, et al., *Hum. Pathol.*, 28: 740-744 (1997).
111. Turner et al., *Br. J. Cancer*, 86: 1276-1282 (2002).
112. Uemura et al. [*J. Urology*, 1571 (4 Supp.): 377 (Abstract 1475) (Apr. 16, 1997)]
113. Vermylen et al., *Eur. Respir. J.*, 14: 806-811 (1999);
114. Vullo et al., *Bioorg. Med. Chem. Lett.*, 13: 1005-1009 (2003a).
115. Vullo et al. *J. Enz. Inhib. Med. Chem.*, 18: 403-406 (2003b).
116. Wingo et al., *Biochem. Biophys. Res. Comm.*, 288: 666-669 (2001).
117. Winum et al. *J. Med. Chem.*, 46: 2197-2204 (2003).
118. Wistrand and Lindqvist, "Design of carbonic anhydrase inhibitors and the relationship between the pharmacodymanics and pharmacokinetics of acetazolamide," In *Carbonic Anhydrase—From Biochemistry and Genetics to Physiology and Clinical Medicine*, Botrè et al., Eds., VCH, Weinheim, pp. 352-378 (1991).
119. Workman and Stratford, *Cancer and Metastasis Reviews*, 12: 73-82 (1993)
120. Wu et al., *J. Membr. Biol.* 162: 31-38 (1998).
121. Wykoff et al., *Cancer Research*, 60: 7075-7083 (2000).
122. Wykoff et al., *Am. J. Pathol.*, 158: 1011-1019 (2001).
123. Zavada et al., *Int. J. Cancer*, 54: 268-274 (1993).
124. Fischer et al., *Clin. Immunol.*, 96: 252-263 (2000).
125. Fukumura et al., *Cancer Res.*, 61: 6020-6024 (2001).
126. Gerweck et al., *Semin. Radiat. Oncol.*, 8: 176-182 (1998).
127. Helmlinger et al., *Clin. Cancer Res.*, 8: 1284-1291 (2002).
128. Ivanov et al., *Proc. Natl. Acad. Sci.* (USA), 95: 12596-12601 (1998).
129. Kaluz et al., *Cancer Res.*, 62: 4469-4477 (2002).
130. Kato et al., *J. Biol. Chem.*, 267: 11424-11430 (1992).
131. Karumanchi et al., *Physiol. Genomics*, 5: 119-128 (2001).
132. Martinez-Zaguilan et al., *Clin. Exp. Metastasis*, 14: 176-186 (1996).
133. Mekhail et al., *Nature Cell Biol.*, 6: 642-647 (2004).
134. Newell et al., *Proc. Natl. Acad. Sci.* (USA), 90: 1127-1131 (1993).
135. Pastorekova et al., *Bioorg. Med. Chem. Lett.*, 14: 869-873 (2004).
136. Potter and Harris, *Br. J. Cancer*, 89: 2-7 (2003).
137. Raghunand and Gillies, *Novartis Found Symp.*, 240: 199-211 (2001).
138. Robertson et al., *Cancer Research*, 64: 6160-6165 (2004).
139. Semenza et al., *Nat. Rev. Cancer*, 3: 721-732 (2003).
140. Sterling et al., *J. Biol. Chem.*, 276: 47886-47894 (2001).
141. Sterling et al., *J. Biol. Chem.*, 277: 25239-46 (2002).
142. Supuran et al., *Eur. J. Med. Chem.*, 33: 83-93 (1998).
143. Tanaka et al., *Brain Res Dev Brain Res*, 121(2): 223-228 (2000).
144. Yamagata et al., *Br. J. Cancer*, 77: 1726-1731 (1998).
145. Zatovicova et al., *J. Immunol. Methods*, 282: 117-134 (2003).
146. Zavada et al., *Br. J. Cancer*, 82: 1808-1813 (2000).

ABBREVIATIONS

The following abbreviations are used herein:
aa—amino acid
AAZ—acetazolamide
AE—anion exchanger
ATCC—American Type Culture Collection
ΔCA—deletion mutant of CA IX lacking the catalytic domain
ΔPG—deletion mutant of CA IX lacking the proteoglycan-like domain
bp—base pairs
BRL—Bethesda Research Laboratories
BRZ—brinzolamide
BSA—bovine serum albumin
CA—carbonic anhydrase
CAI—carbonic anhydrase inhibitor
CAM—cell adhesion molecule
CARP—carbonic anhydrase related protein
Ci—curie
cm—centimeter
CNS—central nervous system
cpm—counts per minute
C-terminus—carboxyl-terminus
° C.—degrees centigrade
DCP—dichlorophenamide
DEAE—diethylaminoethyl
DMEM—Dulbecco modified Eagle medium
ds—double-stranded
DZA—dorzolamide
EDTA—ethylenediaminetetraacetate
EZA—ethoxzolamide
F—fibroblasts
FCS—fetal calf serum
FITC—fluorescein isothiocyanate
H—HeLa cells; hypoxia
HIF—hypoxia inducible factor
IC—intracellular
kb—kilobase
kbp—kilobase pairs
kd or kDa—kilodaltons
$K_I$—inhibition constant
KS—keratan sulphate
LTR—long terminal repeat
M—molar
mA—milliampere
MAb—monoclonal antibody
ME—mercaptoethanol
MEM—minimal essential medium
min.—minute(s)
mg—milligram
ml—milliliter
mM—millimolar
MMC—mitomycin C
mmol—millimole
MZA—methazolamide
N—normal concentration; normoxia
NEG—negative
ng—nanogram
nm—nanometer
nM—nanomolar
nt—nucleotide
N-terminus—amino-terminus
ODN—oligodeoxynucleotide
ORF—open reading frame
PA—Protein A
PBS—phosphate buffered saline
PCR—polymerase chain reaction
PG—proteoglycan
pHe—extracellular pH
pI—isoelectric point
PMA—phorbol 12-myristate 13-acetate
POS—positive
PVDF—polyvinylidene difluoride
pVHL—von Hippel-Lindau tumor suppressor protein
Py—pyrimidine
QAS—quaternary ammonian sulfonilamide
QSAR—quantitative structure-activity relationship(s)
RACE—rapid amplification of cDNA ends
RCC—renal cell carcinoma
RIA—radioimmunoassay
RIP—radioimmunoprecipitation
RIPA—radioimmunoprecipitation assay
RNP—RNase protection assay
RT-PCT—reverse transcription polymerase chain reaction
SAC—*Staphylococcus aureus* cells
SAR—structure-activity relationship
sc—subcutaneous
SDS—sodium dodecyl sulfate
SDS-PAGE—sodium dodecyl sulfate-polyacrylamide gel electrophoresis
SINE—short interspersed repeated sequence
SP—signal peptide
SP-RIA—solid-phase radioimmunoassay
TBE—Tris-borate/EDTA electrophoresis buffer
TC—tissue culture
TCA—trichloroacetic acid
TC media—tissue culture media
tk—thymidine kinase
TM—transmembrane
Tris—tris (hydroxymethyl) aminomethane
μCi—microcurie
μg—microgram
μl—microliter
μM—micromolar

Cell Lines

BL21 (DE3)—*Escherichia coli* strain described by Lindskog's group (for CA I, II expression) [Lindskog et al., "Structure-function relations in human carbonic anhydrase II as studied by site-directed mutagenesis," in *Carbonic anhydrase—From biochemistry and genetics to Physiology and clinical medicine*, Botre et al., Eds., VCH, Weinheim, pp. 1-13 (1991)]
BL21-GOLD—*Escherichia coli* strain (from Stratagene) used for CA IX (DE3) expression)
HeLa—cell line derived from human cervical adenocarcinoma; cells normally express endogenous CA IX
HeLa—ΔCA—HeLa cells stably transfected with recombinant plasmids to contain ΔCA but not CA IX under normoxia, and express both proteins under hypoxia, which apparently form mixed oligomers (composed of both CA IX and ΔCA)
HeLa-mock—HeLa cells cotransfected with empty pSG5C and pSV2 neo plasmids as negative controls
MDCK—cell line derived from normal canine tubular kidney epithelium; cells do not express endogenous CA IX
MDCK-CA IX—MDCK cells stably transfected with recombinant plasmids to express CA IX constitutively
MDCK-mock—MDCK cells cotransfected with empty pSG5C and pSV2 neo plasmids as negative controls SiHa—cell line derived from human cervical squamous cell carcinoma; cells normally express endogenous CA IX Nucleotide and Amino Acid Sequence Symbols The following symbols are used to represent nucleotides herein:

| Base Symbol | Meaning |
| --- | --- |
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
| --- | --- | --- |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIG. 1A-C provides the nucleotide sequence for MN/CA IX full-length cDNA [SEQ ID NO: 1]. FIG. 1 A-C also sets forth the predicted amino acid sequence [SEQ ID NO: 2] encoded by the cDNA.

FIG. 2A-F provides a 10,898 bp complete genomic sequence of MN/CA9 [SEQ ID NO: 3]. The base count is as follows: 2654 A; 2739 C; 2645 G; and 2859 T. The II exons are in general shown in capital letters, but exon 1 is considered to begin at position 3507 as determined by RNase protection assay.

FIG. 3 provides an exon-intron map of the human MN/CA9 gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53-111) [SEQ ID NO: 4] and the human aggrecan (aa 781-839) [SEQ ID NO: 5].

FIG. 4 A-B shows the chemical structures of the 26 different sulfonamide compounds tested in Example 1.

FIG. 5 shows the scheme for the general synthesis of compounds 71-91 of Example 3 (Scheme 1).

FIG. 6 shows the scheme for the reaction between a pyrylium salt and an amine (Scheme 2), as described in Example 3.

FIG. 7 (discussed in Example 4) illustrates the CA IX-mediated acidification of the extracellular pH in hypoxia. Values of pHe [FIG. 7A] and lactate [FIG. 7B] concentrations are shown in histograms (mean values and standard deviations) for cells grown in the constant medium volumes, maintained in normoxia (N, 21% $O_2$) or exposed to hypoxia (H, 2% $O_2$) for 48 hours. The cells tested were CA IX-transfected MDCK cells and mock-transfected controls for comparison. Five independent experiments with three different clones of the transfectants and three parallel dishes for each clone were performed.

FIG. 8 (discussed in Example 5) shows sulfonamide inhibition and binding to hypoxic MDCK-CA IX cells. [FIG. 8B] The sulfonamides were added to MDCK-CA IX cells just before the cells were transferred to hypoxia, and pHe was measured 48 hours later. At least three independent experiments with three parallel dishes per sample were performed for each inhibitor. Data are expressed as differences between the pH values ($\Delta$pH) measured in the untreated versus treated cells and include the standard deviations.

FIG. 9 (discussed in Example 6) shows the expression and acidification capability of the CA IX deletion mutants. FIG. 9A is a schematic drawing of the domain composition of the wild-type (wt) CA IX with the amino acid positions indicating an extent of deletions in the N-terminal PG domain ($\Delta$PG) and the central CA domain ($\Delta$CA): SP, signal peptide; PG, proteoglycan-like region; CA, carbonic anhydrase domain; TM, transmembrane anchor; IC, intracytoplasmic tail. [FIG. 9B] Extracellular pH and production of lactate in the transfected MDCK cells. At least three independent experiments were performed using three clonal cell lines for each transfected variant with at least three parallel dishes. Data are expressed as mean differences in the pH values ($\Delta$pH) and in the lactate concentrations ($\Delta$mg/ml), respectively.

FIG. 10 (discussed in Example 7) shows treatment of the tumor cells by Compound 92 sulfonamide [FITC derivative of homosulfanilamide (Compound 5)]. HeLa and SiHa cervical carcinoma cells were incubated for 48 hours in normoxia and hypoxia, respectively, either in the absence or in the presence of 1 mM of the Compound 92 sulfonamide. Mean differences in the pH values determined in the treated versus control dishes are shown on the histogram with indicated standard deviations. The experiment was repeated three times using at least three parallel dishes for each sample.

FIG. 11 (discussed in Example 8) illustrates ectopic expression of ΔCA mutant in HeLa cells. Values of pHe in the culture media of HeLa cells transfected with ΔCA in comparison to the mock-transfected controls. Data represent mean differences in the pH values and corresponding standard deviations. The experiment was repeated three times with three different clones of the transfected HeLa, each having at least three parallel dishes.

DETAILED DESCRIPTION

Figure 8A:
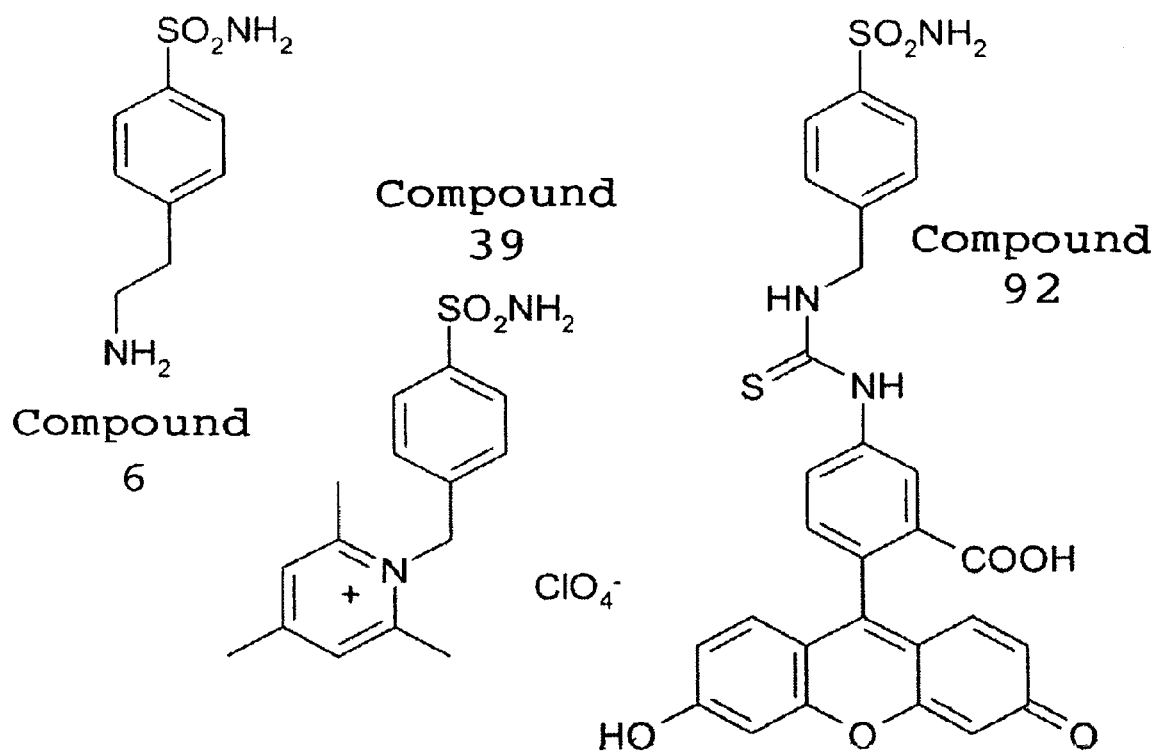
FIG. 8A shows the chemical structures of the CA IX-selective inhibitors used in Examples 5-8: Compound 6 [4-(2-aminoethyl)-benzenesulfonamide], Compound 39 [4-(2,4,6-trimethylpyridinium-N-methylcarboxamido)-benzensulfonamide perchlorate], and Compound 92 [FITC derivative of homosulfanilamide (Compound 5)].

The novel methods of the present invention comprise inhibiting the growth of tumor cells which overexpress MN protein with compounds that inhibit the enzymatic activity of MN protein. Said compounds are organic or inorganic, preferably organic, more preferably sulfonamides. Still more preferably, said compounds are pyridinium derivatives of aromatic or heterocyclic sulfonamides. These preferred pyridinium derivatives of sulfonamides are likely to have fewer side effects than other compounds in three respects: they are small molecules, they are membrane-impermeant, and they are specific potent inhibitors of the enzymatic activity of the tumor-associated MN/CA IX protein.

The use of oncoproteins as targets for developing new cancer therapeutics is considered conventional by those of skill in the art. [See, e.g., Mendelsohn and Lippman [61]. However, the application of such approaches to MN is new. In comparison to other tumor-related molecules (e.g. growth factors and their receptors), MN has the unique property of being differentially expressed in preneoplastic/neoplastic and normal tissues, which are separated by an anatomic barrier.

The pyridinium derivatives of sulfonamides of the present invention can be formed, for example, by creating bonds between pyrylium salts and aromatic or heterocyclic sulfonamide reagents, as described below. The aromatic or heterocyclic sulfonamide portion of a pyridinium salt of a sulfonamide compound can be called the "head," and the pyridinium portion can be called the "tail."

It can be appreciated by those of skill in the art that various other types of linkages can couple the pyridinium portion with the sulfonamide portion. It can further be appreciated that alternate methods, in addition to those disclosed herein, can be used to make the pyridinium derivatives of the present invention.

As used herein, "cancerous" and "neoplastic" have equivalent meanings, and "precancerous" and "preneoplastic" have equivalent meanings.

As used herein, the term "aromatic" when applied to sulphonamide structures means "comprising an aromatic ring, without an additional heterocyclic ring." The term "heterocyclic" when applied to sulphonamide structures means "comprising a heterocyclic ring, with or without an additional aromatic ring."

As used herein, the term "alkyl", alone or in combination, refers to a straight-chain or branched-chain alkyl radical containing from 1 to 12, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, isoamyl, hexyl, decyl and the like.

The term "aryl", alone or in combination, means a phenyl or naphthyl radical which optionally carries one or more substituents selected from alkyl, alkoxy, halogen, hydroxy, amino, nitro, cyano, haloalkyl, carboxy, alkoxycarbonyl, cycloalkyl, heterocycloalkyl, amido, mono and dialkyl substituted amino, mono and dialkyl substituted amido and the like, such as phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl and the like.

Preferred sulfonamides of the present invention are aromatic and heterocyclic sulfonamides. The structures of representative sulfonamides of this group, designated 1-26, are shown in FIG. 4.

More preferred sulfonamides of the present invention are pyridinium derivatives of aromatic sulfonamides and have the general formula (A) below,

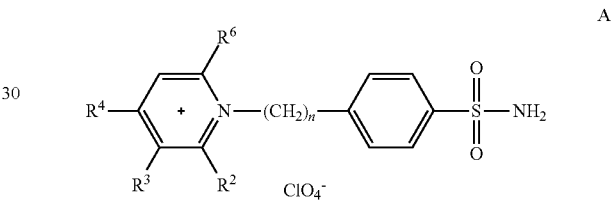

wherein n is 0, 1, or 2; and R2, R3, R4 and R6 are each independently selected from the group consisting of hydrogen, alkyls and aryls. The structures of representative sulfonamides of this group, designated 27 through 70, are shown as derivatives of the general structure (A), in Table 2.

Alternatively, more preferred sulfonamides of the present invention are pyridinium derivatives of heterocyclic sulfonamides and have the general formula (B) below, wherein said pyridinium derivative of a heterocyclic sulfonamide has the general formula of:

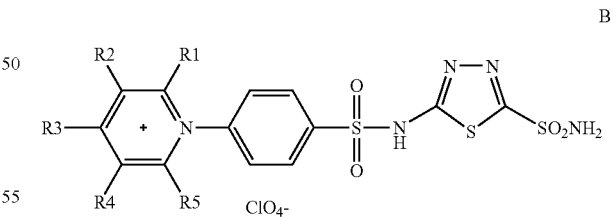

wherein R1, R2, R3, R4 and R5 are each independently selected from the group consisting of hydrogen, alkyls and aryls. The structures of representative sulfonamides of this group, designated 71 through 91, are shown as derivatives of the general structure (B), in Table 3.

Representative sulfonamide derivatives of the group of compounds represented by the general formulas (A) and (B) have CA IX inhibitory activity, and are potentially useful therapeutically as anticancer agents in treating MN-associated tumors.

Further, biologic activity of the identified sulfonamides will be tested in vitro by inhibition of the carbonic anhydrase enzymatic activity of the MN protein, by effects on cell morphology and growth characteristics of MN-related tumor cells (HeLa) and of control cells [104]. In vivo screening will be carried out in nude mice that have been injected with HeLa cells.

It can be appreciated by those of skill in the art that various other CA IX-specific inhibitors can be useful according to the methods of the invention, and may comprise any molecules that preferentially bind only the activated form of the CA domain of CA IX, and not the inactive form of the CA domain of CA IX. Such molecules may be organic or inorganic, preferably organic molecules. Such organic molecules may be antibodies, preferably monoclonal antibodies, which selectively bind the activated form of the CA domain of CA IX. For example, monoclonal antibodies have been described which specifically recognize the epitope of caspases that is characteristic of the activated form of those proteases [143]. Therefore, activation of the CA domain of CA IX could theoretically be detected both indirectly from tumor cell samples and directly in situ, immunocytochemically.

Representative Sulfonamide Inhibitors of CA IX

The sulfonamides investigated in Example 1 for the inhibition of the tumor-associated isozyme CA IX, of types 1-26 are shown in FIG. 4A-B. Compounds 1-6, 11-12, 20 and 26 are commercially available, whereas 7-10 [43], 13-19 [24, 90, 97] and 21-25 [79] were prepared as reported earlier. The six clinically used compounds were also assayed. For Example 2 compounds (pyridinium derivatives of aromatic sulfonamides), reaction of sulfanilamide, homosulfanilamide or 4-(2-aminoethyl)-benzenesulfonamide with 2,6-di-, 2,4,6-tri- or 2,3,4,6-tetrasubstituted pyrylium salts afforded the pyridinium salts 27-70 investigated here, by the general Bayer—Piccard synthesis [9, 10, 97].

As described in Example 3, a series of positively-charged sulfonamides, designated here as compounds 71-91, were obtained by reaction of aminobenzolamide (5-(4-aminobenzenesulfonylamino)-1,3,4-thiadiazole-2-sulfonamide) with tri-/tetra-substituted pyrilium salts possessing alkyl-, aryl- or combinations of alkyl and aryl groups at the pyridinium ring (described below). Three of these compounds (71, 75, and 87) have been described elsewhere [25, 85]; all other compounds of this series are new.

Heterocyclic Sulfonamide Inhibitors of CA IX: Synthesis of Pyridinium Derivatives of Aminobenzolamide Chemistry: Reaction of aminobenzolamide (5-(4-aminobenzenesulfonylamino)-1,3,4-thiadiazole-2-sulfonamide) [97] with 2,6-di-, 2,4,6-tri- or 2,3,4,6-tetrasubstituted pyrylium salts afforded the pyridinium salts 71-91 investigated here, by the general synthesis of such derivatives with nucleophiles (Scheme 1 as shown in FIG. 5) [6, 26, 108].

Preparation of Compounds: a Large Number of Positively-Charged sulfonamides, prepared by reaction of amino-sulfonamides with pyrylium salts [23, 88, 89] were recently reported by this group, and generally tested as inhibitors of the "classical" isozymes CA I, II and IV [81, 96, 97, 98]. Based on QSAR studies on several series of CA inhibitors, including some positively-charged derivatives [23, 88, 89], it emerged that the enhancement of CA inhibitory activity is correlated with increased positive charges on the heterocyclic/aromatic ring incorporated in such molecules, as well as with "long" inhibitor molecules per se (i.e., molecules extending on the direction passing through the Zn(II) ion of the enzyme, the sulfonamide nitrogen atom and the long axis of the inhibitor) [23, 88, 89]. It appeared thus of interest to try to explore this result, designing positively-charged, long sulfonamide CAIs. Thus, we thought of attaching substituted-pyridinium moieties to an already potent and long-molecule CAI suitable for reaction with pyrylium salts, i.e., aminobenzolamide [97]. Indeed, this compound acts as a very potent CAI against isozymes I, II and IV (with inhibition constants in the low nanomolar range—see later in the text). The substitution pattern of the pyridinium ring was previously shown [81, 96, 97, 98] to be critical for the biological activity of this type of sulfonamide CAIs. Thus, a large series of 2,4,6-trialkylpyridinium-; 2,6-dialkyl-4-phenylpyridinium-; 2-alkyl-4,6-diphenylpyridinium-; 2,4,6-triphenylpyridinium-, together with various 2,6-disubstituted-pyridinium and 2,3,5,6-tetrasubstituted-pyridinium aminobenzolamide derivatives have been prepared by the reaction described in Scheme 1 (Shown in FIG. 5).

Although apparently simple, the reaction between a pyrylium salt and an amine, leading to pyridinium salts, is in reality a complicated process (Scheme 2, shown in FIG. 6), as established by detailed spectroscopic and kinetic data from Balaban's and Katritzky's groups [6, 26, 108]. Thus, the nucleophilic attack of a primary amine $RNH_2$ on pyrylium cations generally occurs in the α position, with the formation of intermediates of type IV (depicted in FIG. 6), which by deprotonation in the presence of bases lead to the 2-amino-tetradehydropyran derivatives V. In many cases the deprotonation reaction is promoted by the amine itself, when this is basic enough (this being the reason why in many cases one works at molar ratios pyrylium:amine of 1:2 when pyridinium salts are prepared by this method), or by external catalysts added to the reaction mixture, such as triethylamine [6, 26, 108]. The derivatives V are generally unstable, being tautomers with the ketodieneamines VI which are the key intermediates for the conversion of pyryliums into pyridiniums [6, 26, 108]. In acidic media, in the rate-determining step of the whole process, ketodieneamines VI may be converted to the corresponding pyridinium salts VII, although other products, such as vinylogous amides with diverse structures have also been isolated in such reactions [6, 26, 108]. A supplementary complication appears when the moiety substituting the 2- and/or 6-position(s) of the pyrylium ring is methyl, cases in which a concurrent cyclisation with formation of the anilines VII in addition to the pyridinium salts VII, may take place too [6, 26, 108]. These concurrent reactions mentioned above are generally important when the amine to be converted into the pyridinium salt possesses weak nucleophilicity or basicity. This happens to be the case of aminobenzolamide. In fact, reaction of aminobenzolamide with several pyrylium salts, performed in a variety of conditions (different solvents, such as low molecular weight alcohols (MeOH, EtOH, i-PrOH); DMF; methylene chloride; acetonitrile; diverse molar ratios of the reagents; temperatures from 25 to 150° C.; reaction times between 15 min and 48 hours, etc) led only to the isolation of the unreacted raw materials. The only conditions which led to the formation of the pyridinium salts III (depicted in FIG. 5) were the following: anhydrous methanol in the presence of acetic anhydride as solvent and triethylamine as catalysts for the deprotonation of the intermediates IV. Acetic anhydride had the role of reacting with the water formed in the condensation reaction. This water may in fact act as a competitive nucleophile with aminobenzolamide when reacting with the pyrylium cation, and as a consequence the yields in pyridinium salts would dramatically be decreased. After the rapid formation of the ketodieneamine, catalyzed by triethylamine (and in the presence of the acetic anhydride as water scavenging agent), the cyclisation to the pyridinium ring (the rate-determining step) has been achieved by refluxation in the presence of acetic acid (2-5 hours). Still the yields were not always good, especially for the 2-methyl-containing derivatives.

Representative Sulfonamide Inhibitors of Activated CA IX

In Examples 5 and 7 below, three exemplary CA IX-selective inhibitors tested for extracellular pH effects [Compounds 6, 39 and 92 (the FITC-derivative of Compound 5) as shown in FIG. 8A] bind to CA IX preferentially under conditions of hypoxia. As indicated in Example 5, all three sulfonamides were able to reduce the extracellular acidification of MDCK-CA IX cells in hypoxia, and their effect on the normoxic pHe was negligible [FIG. 8]. The FITC-labeled Compound 92 was detected only in hypoxic MDCK-CA IX cells, but was absent from their normoxic counterparts and from the mock-transfected controls.

Exclusive binding of the FITC-conjugated Compound 92 sulfonamide to the hypoxic cells that express activated CA IX (described in Example 7) offers an attractive possibility for the use of similar sulfonamide-based compounds for imaging purposes in vivo. Moreover, CA IX-selective sulfonamide derivatives may potentially serve as components of the therapeutic strategies designed to increase pHe in the tumor microenvironment and thereby reduce the tumor aggressiveness and the drug uptake [18, 86, 106, 126].

It is generally accepted that the reaction between CA and inhibitor occurs principally via a coordination of the ionized inhibitor to the zinc ion through the network of hydrogen bonds with amino acid residues of the active site, which effectively means that the inhibitor can efficiently bind only to active CA isoforms [102]. It cannot be excluded that hypoxia influences the conformation and hence the accessibility of the active site of CA IX, but this assumption warrants further studies.

Preparation of MN Proteins and/or Polypeptides

The terms "MN/CA IX" and "MN/CA9" are herein considered to be synonyms for MN. Also, the G250 antigen is considered to refer to MN protein/polypeptide [112].

Zavada et al., WO 93/18152 and/or WO 95/34650 disclose the MN cDNA sequence shown herein in FIG. 1A-1C [SEQ ID NO: 1], the MN amino acid sequence [SEQ ID NO: 2] also shown in FIG. 1A-1C, and the MN genomic sequence [SEQ ID NO: 3] shown herein in FIG. 2A-2F. The MN gene is organized into 11 exons and 10 introns.

The first thirty seven amino acids of the MN protein shown in FIG. 1A-1C is the putative MN signal peptide [SEQ ID NO: 6]. The MN protein has an extracellular domain [amino acids (aa) 38-414 of FIG. 1A-1C [SEQ ID NO: 7], a transmembrane domain [aa 415-434; SEQ ID NO: 8] and an intracellular domain [aa 435-459; SEQ ID NO: 9]. The extracellular domain contains the proteoglycan-like domain [aa 53-111: SEQ ID NO: 4] and the carbonic anhydrase (CA) domain [aa 135-391; SEQ ID NO: 5].

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below. A representative method to prepare the MN proteins shown in FIG. 1 or fragments thereof would be to insert the full-length or an appropriate fragment of MN cDNA into an appropriate expression vector as exemplified in the Materials and Methods section.

MN Gene

FIG. 1A-C provides the nucleotide sequence for a full-length MN cDNA clone [SEQ ID NO: 1] isolated as described in Zavada et al., WO 95/34650. FIG. 2A-F provides a complete MN genomic sequence [SEQ ID NO: 3].

The ORF of the MN cDNA shown in FIG. 1 has the coding capacity for a 459 amino acid protein with a calculated molecular weight of 49.7 kd. The overall amino acid composition of the MN/CA IX protein is rather acidic, and predicted to have a pI of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pIs ranging from 4.7 to 6.3.

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

Enzymatic Screening Assays

Assays are provided herein for the screening of compounds for inhibition of the enzymatic activity of the MN protein. Such assays comprise the incubation of said compound with said MN protein and with a substrate selected from the group consisting of saturated $CO_2$ and 4-nitrophenylacetate, preferably saturated $CO_2$, and determination of the inhibition constant $K_I$ of said compound, wherein said enzymatic activity of the MN protein is measured by the pH change of an indicator by stopped flow spectrophotometer.

Screening of representative heterocyclic and aromatic sulfonamides for inhibition of MN protein: From Example 1, it was found that the inhibition profile of isozyme CA IX is very different from that of the classical isozymes CA I and II (cytosolic) as well as CA IV (membrane-bound). The following particular features may be noted: (i) all the 32 sulfonamides investigated in Example 1 act as CA IX inhibitors, with inhibition constants in the range of 14-285 nM (the corresponding affinities for the other three isozymes vary in a much wider range, as seen from data of Table 1). Based on these data, it can be noted that CA IX is a sulfonamide avid CA, similarly to CA II, the isozyme considered up to now to be responsible for the majority of pharmacological effect of sulfonamides [22, 29, 83, 93, 94, 95, 102]. Still, many other differences are observed between CA IX and other isozymes for which inhibitors were developed for clinical use; (ii) for CA I, II and IV, generally, aromatic sulfonamides behave as weaker inhibitors as compared to heterocyclic derivatives (compare 1-6, or DCP), as aromatic compounds, with 15, 21, AAZ, MZA, EZA, DZA or BRZ among others (as heterocyclic sulfonamides). In the case of CA IX, such a fine distinction is rather difficult to be made, since both aromatic (such as 1, 6, 11, 12, 17, 18, 22-26) derivatives, as well as heterocyclic compounds (such as 14, 15, 21, and the clinically used sulfonamides—except dichlorophenamide) possess rather similar inhibition constants, in the range of 14-50 nM; (iii) orthanilamide derivatives (such as 1, 17 and 22) behave as very potent CA IX inhibitors ($K_I$-s in the range of 20-33 nM), although they are weak or medium-weak inhibitors of CA I, II and IV; (iv) 1,3-benzene-disulfonamide derivatives (such as 11, 12 and DCP) are again strong CA IX inhibitors, with $K_I$-s in the range of 24-50 nM, although their CA II, I and IV inhibition profile is not particularly strong; (v) metanilamide 2, sulfanilamide 3, and 4-hydrazino-benzenesulfonamide 4 show CA IX inhibition data quite similar with those against CA II, whereas homosulfanilamide 5 and 4-aminoethyl-benzensulfonamide 6 act as better CA IX inhibitors as compared to CA II inhibition; (vi) the halogenosulfanilamides 7-10 are much weaker inhibitors of CA IX than of CA II, a finding difficult to interpret at this moment; (vii) the strongest CA II inhibitor among the investigated compounds, 4-aminobenzolamide 15 ($K_I$ of 2 nM) is not the strongest CA IX inhibitor ($K_I$ of 38 nM). Instead, the best CA IX inhibitor detected so far is the ethoxzolamide phenol 21 ($K_I$ of 14 nM). It is interesting to note that 21 and EZA have the same affinity for CA II, whereas their affinity for CA IX is rather different, with the phenol more active than the ethoxy-derivative; (viii) among the clinically used compounds, the best inhibitor is acetazolamide, followed by methazolamide, ethoxzolamide and brinzolamide. The most ineffective (but appreciably inhibiting the isozyme IX) are dichlorophenamide and dorzolamide; (ix) sulfonamides 20 and 22-26 behave as very good CA IX inhibitors, with $K_I$-s in the range of 16-32 nM, being slightly more effective than the clinically used CAIs mentioned above, and among the best CA IX inhibitors detected so far. It is thus envisageable that such compounds may be used as lead molecules for obtaining more potent and eventually specific CA IX inhibitors, with applications as antitumor agents.

Screening of representative pyridinium derivatives of aromatic sulfonamides for inhibition of MN protein: From Example 2, wherein membrane-impermeant pyridinium derivatives of sulfonamides were tested for their ability to inhibit the enzymatic activity of CA IX, the following conclusions were drawn from data of Table 2: (i) for a given substitution pattern of the pyridinium ring, the 4-aminoethyl-benzenesulfonamide derivatives 55-70 were more active than the corresponding homosulfanilamide derivatives 39-54, which in turn were more active than the corresponding sulfanilamides 27-38. This behavior has also been observed for the other three investigated isozymes [96]; (ii) some of the derivatives possessing bulky substitutents at the pyridinium ring (mainly phenyls, tert-butyls; n-butyl, n-propyl or isopropyl), such as 34-37, 51 and 67, were very ineffective CA IX inhibitors, showing inhibition constants >500 nM; (iii) another group of compounds, including 27, 30-33, 44, and 60 showed a moderate inhibitory power towards the tumor-associated isozyme IX, showing $K_I$ values in the range of 160-450 nM. Most of these compounds are sulfanilamide derivatives (except 44 and 60), and the substitution pattern at the pyridinium ring includes (with one exception, 27) at least one phenyl group in 4, or two phenyls in the 2 and 4 positions. It should be noted that the corresponding homosulfanilamides and 4-aminoethylbenzene-sulfonamides incorporating the same substitution pattern as the compounds mentioned above (sulfanilamides), lead to much better CA IX inhibitors (see later in the text); (iv) a third group of derivatives, including 38, 45-50, 52, 53, 61, 63-66, 68 and 69, showed good CA IX inhibitory properties, with $K_I$ values in the range of 64-135 nM. As mentioned above, except for the tetramethyl-pyridinium-substituted derivative 38, most of these compounds incorporate 4-phenyl-pyridinium or 2,4-diphenylpyridinium moieties, whereas the group in position 6 is generally quite variable (alkyls or phenyl are tolerated). The most interesting observation regarding this subtype of CA IX inhibitors is constituted by the fact that the 2,4,6-triphenyl-pyridinium- and 2,6-diphenyl-pyridinium derivatives of homosulfanilamide and 4-aminoethylbenzenesulfonamide (52-53 and 68-69) efficiently inhibit isozyme IX, although they act as very weak inhibitors for isozymes I, II and IV (Table 2). As it will be discussed shortly, this may be due to the fact that the hCA IX active site is larger than that of the other investigated isozymes, notably CA II, I and IV; (v) a last group of derivatives (28-29; 39-43; 54; 55-59; 62 and 70) showed very good CA IX inhibitory properties, these compounds possessing $K_I$ values in the range of 6-54 nM, similarly to the clinically used inhibitors acetazolamide, methazolamide, dichlorophenamide and indisulam, for which the inhibition data are provided for comparison. It should be noted that three derivatives 58, 59 and 70 showed inhibition constants <10 nM, these being the most potent CA IX inhibitors ever reported up to now. Correlated with their membrane-impermeability [96, 85], it may be assumed that in vivo such compounds may lead for the first time to a selective CA IX inhibition. Thus, the best substitution pattern at the pyridinium ring includes either only compact alkyls (39-41, 54, 55 and 70), or 2,6-dialkyl-4-phenyl-pyridinium moieties (all compounds mentioned above except 62, which incorporates a 2-methyl-4,6-diphenylpyridinium ring); (vi) the number of the substitutents at the pyridinium ring seems to be less important for the activity of this series of CAIs, since both di-, tri- or tetrasubstituted derivatives showed good inhibitory potency. The nature of these groups on the other hand—as discussed in detail above—is the most important parameter influencing CA inhibitory properties (together with the linker between the benzenesulfonamide moiety and the substituted pyridinium ring); (vii) the isozyme most similar to hCA IX regarding the affinity for these inhibitors was hCA II (which has 33% homology with hCA IX) [Pastorek et al. (1994), supra] whereas the affinities of isozymes I and IV were rather different.

Screening of representative pyridinium derivatives of heterocyclic sulfonamides for inhibition of MN protein, and comparison with inhibition of other CA isozymes: Isozyme I. As seen from data of Table 3, all derivatives 71-91 reported here act as very efficient CAIs against this isozyme which is generally the most "resistant" to inhibitors of this type [30, 31, 100, 102]. Indeed, aminobenzolamide is already a highly potent CA I inhibitor ($K_I$ of 6 nM), whereas inhibitors 71-91 show inhibition constants in the range of 3-12 nM, in contrast to the clinically used sulfonamide CAIs which are much less effective inhibitors, with $K_I$ values in the range of 30-1200 nM (Table 3). Thus, derivatives possessing several bulky groups (i-Pr; t-Bu; n-Pr; n-Bu; Ph, etc) substituting the pyridinium moiety, such as 73, 74, 77, 78, 82, 84, 85 showed a decreased inhibitory activity as compared to aminobenzolamide, with $K_I$ values in the range of 7-12 nM (aminobenzolamide has a $K_I$ of 6 nM against hCA I). The rest of the compounds were more efficient as compared to aminobenzolamide in inhibiting this isozyme, with $K_I$ values in the range of 3-5 nM. Best CA I inhibitors were 75, and 89-91 ($K_I$ of 3 nM), all of which containing either only alkyl moieties or 4-Ph and other alkyl moieties substituting the pyridinium ring. These are probably the best CA I inhibitors ever reported up to now, since the clinically used CAIs show much higher inhibition constants against isozyme I (Table 3).

Isozyme II. Aminobenzolamide is already a very potent CA II inhibitor, with an inhibition constant around 2 nM. Several of the new inhibitors, such as 74, 77, 78, 82-88 act as weaker CA II inhibitors as compared to aminobenzolamide, with $K_I$ values in the range of 3.13-5.96 nM (but all these compounds act as potent inhibitors, being much more effective than the clinically used CAIs acetazolamide, methazolamide, dichlorophenamide or indisulam—see Table 3). Again the substitution pattern at the pyridinium ring is the main discriminator of activity for these compounds: all the less active derivatives mentioned above incorporate at least two bulky/long aliphatic groups, mainly in positions 2- and 6- of the pyridinium ring (n-Pr; t-Bu; n-Bu; and Ph). The best CA II inhibitors among derivatives 71-91 were those incorporating more compact 2,6-substituents at the pyridinium ring (such as Me, Et) together with a 4-Me or 4-Phe moiety, or those incorporating only aliphatic such groups, such as 71-73, 75, 76, 79-81, 89-91, which showed $K_I$ values in the range of 0.20-1.61 nM (thus, for the best inhibitors a factor of 10 increase in inhibitory power as compared to aminobenzolamide). It should be mentioned that iso-propyl-substituted compounds (73, 79) are active as CA II inhibitors, although their activity against CA I was not so good.

Isozyme IV. Most sulfonamides show inhibitory activity against CA IV intermediate between those towards CA I (less susceptible) and CA II (very high affinity for sulfonamides). This is also the trend observed with the sulfonamides investigated here, derivatives of aminobenzolamide. Thus, the parent sulfonamide (shown in FIG. 5) is a potent CA IV inhibitor, with a $K_I$ value around 5 nM. The new derivatives of general formula (B) incorporating bulky pyridinium-ring substituents (such as 74, 77, 78, 82, 84-88, 90) were less effective than aminobenzolamide, showing $K_I$ values in the range of 5.2-10.3 nM, whereas the compounds showing the other substitution pattern mentioned above were better CA IV inhibitors, showing $K_I$ values in the range of 2.0-4.7 nM.

Isozyme IX. Aminobenzolamide is less inhibitory against this isozyme ($K_I$ of 38 nM) as compared to other isozymes discussed above. This behavior is difficult to explain at this point, since no X-ray crystal structure of this isozyme has been reported. A very encouraging result obtained with the new derivatives of general formula (B) reported here, was the observation that several of them show very high affinity for CA IX, with $K_I$ values in the range of 3-9 nM (derivatives 71, 72, 75, 76, and 89). It may be seen that all of them incorporate aliphatic moieties (Me, Et and i-Pr) in positions 2- and 6- of the pyridinium ring, and either 4-Me or 4-Ph moieties. Only one compound is tetrasubstituted (89), again possessing only methyl moieties. The best CA IX inhibitor (and the best ever reported up to now) was 71, which is almost 13 times more effective than benzolamide in inhibiting this isozyme. Another group of new derivatives, such as 73, 74, 77, 79, 80, 81, 83, 86-88, 90, 91, showed effective CA IX inhibition, with $K_I$ values in the range of 12-35 nM, being thus more effective than aminobenzolamide. They incorporate slightly bulkier groups as compared to the previously discussed ones. Again the less effective inhibitors ($K_I$ values in the range of 40-43 nM) were those incorporating several bulky pyridinium substituents, such as 78, 84, 85 which contained either two n-Bu or one Ph and n-Bu/t-Bu in positions 2- and 6- of the pyridinium ring. Thus, SAR is now rather clear for this type of CAIs: best CA IX inhibitors should contain either only small, compact aliphatic moieties substituting the pyridinium ring, or they tolerate a 4-Ph moiety, but the 2,6-substituents should again be small, compact aliphatic moieties. In this particular case, 2,4,6-trisubstituted-pyridinium derivatives were more effective CA IX inhibitors as compared to the tetrasubstituted derivatives.

Membrane impermeability of Heterocyclic Sulfonamide Inhibitors of CA IX. As seen from data of Table 4 of Example 3, incubation of human red cells (which contain high concentrations of isozymes I and II, i.e., 150 µM hCA I and 20 µM hCA II, but not the membrane-bound CA IV or CA IX) [118] with millimolar concentrations of different sulfonamide inhibitors, such as acetazolamide, or methazolamide, led to saturation of the two isozymes present in erythrocytes with inhibitor, already after short periods of incubation (30 min), whereas for benzolamide or aminobenzolamide, a similar effect is achieved after somehow longer periods (60 min) (Table 4). This is obviously due to the high diffusibility through membranes of the first three inhibitors, whereas benzolamide/aminobenzolamide with a $pK_a$ of 3.2 for the second sulfonamido group [58] being present mainly as an (di)anion at the pH at which the experiment has been done (7.4), is already less diffusible and penetrates membranes in a longer time. Different cationic sulfonamides synthesized by us here, such as 71, 76, 89, 91, in the same conditions, were detected only in very small amounts within the blood red cells, proving that they were unable to penetrate through the membranes, obviously due to their cationic nature. Even after incubation times as long as one hour (and longer, data not shown), only traces of such cationic sulfonamides were present inside the blood red cells, as proved by the three assay methods used for their identification in the cell lysate, which were in good agreement with each other (Table 4). This demonstrates that the proposed approach for achieving membrane impermeability works well for the designed positively-charged sulfonamide CAIs of the general formula (B) (shown above), since the very small amount of sulfonamide detected may be due to contamination of the lysates with very small amount of membranes.

Design of Membrane-Impermeant Sulfonamide Inhibitors of CA IX

No X-ray crystal structure of isozyme IX is available up to now, in strong contrast with hCA II, for which many X-ray crystal structures are available (alone or in complexes with inhibitors and activators) [1, 2, 14, 15, 19a, 19b, 37, 38]. Examining the active site residues of these two isozymes and the architecture of hCA II, may help explain the above inhibition data and their relevance for CA IX specific inhibitors.

First of all, the zinc ligands and the proton shuttle residue of these two isozymes are identical [33, 43, 72, 100, 101, 102, 114, 115, 117]. An important difference is constituted by the amino acid in position 131, which is Phe for hCA II and Val for hCA IX. Phe 131 is known to be very important for the binding of sulfonamide inhibitors to hCA II [2, 46, 47]: in many cases this bulky side chain limits the space available for the inhibitor aromatic moieties, or it may participate in stacking interactions with groups present in it (for recent examples see refs. [2, 46, 47]. Thus, the presence of a less bulky such residue in hCA IX (i.e., a valine) which is also unavailable for participation to stacking interactions has as a consequence the fact that the hCA IX active site is larger than that of hCA II. A second potentially important residue is 132, which is Gly in hCA II and Asp in hCA IX. This residue is situated on the rim of the hydrophilic half of the entrance to the active site of hCA II (and presumably also of hCA IX) and it is critical for the interaction with inhibitors possessing elongated molecules, as recently shown by us [19b]. Strong hydrogen bonds involving the CONH moiety of Gly 132 were shown to stabilize the complex of this isozyme with a p-aminoethylbenzene-sulfonamide derived inhibitor [19b]. In the case of hCA IX, the presence of aspartic acid in this position at the entrance of the active site may signify that: (i) stronger interactions with polar moieties of the inhibitor bound within the active site should be possible, since the COOH moiety possesses more donor atoms; (ii) this residue may have flexible conformations, fine-tuning in this way the interaction with inhibitors. Thus, the stronger hCA IX inhibition with some of these inhibitors (as compared to their affinity for isozyme II), such as for example 46-50, 52, 53, 55, 58, 62 and 68-70, might be explained just by the different interactions with the two active site residues mentioned above.

Therapeutic Use of MN-Specific Inhibitors

The MN-specific inhibitors of this invention, organic and/or inorganic, preferably organic, and as outlined above, may be used therapeutically in the treatment of neoplastic and/or pre-neoplastic disease, either alone or in combination with other chemotherapeutic drugs.

The MN-specific inhibitors can be administered in a therapeutically effective amount, preferably dispersed in a physiologically acceptable, non-toxic liquid vehicle.

The MN-specific inhibitors used according to the methods of the invention may exploit activation of CA IX under hypoxia, to specifically target hypoxic conditions, acidic conditions or both conditions.

In addition to targeting hypoxia, CA IX selective inhibitors may be used therapeutically to increase pHe in order to reduce tumor aggressiveness and drug uptake. It is known that the atypical pH gradient of tumor cells (acidic extracellular pH, neutral-to-basic intracellular pH) acts to exclude weak base drugs such as the anthracyclines and vinca alkaloids. In two different mouse tumor models, alkalinization of tumor extracellular pH (using bicarbonate pretreatment) enhanced the anti-tumor activity of the weak base chemotherapeutic agents doxorubicin and mitoxantrone [126, 137]. Most combination chemotherapy regimens include at least one weak base drug, and it may be possible to enhance the efficacy of such drugs with the co-administration of CA IX-specific inhibitors.

Diagnostic/Prognostic and Therapeutic Use of MN-Specific Inhibitors Which Selectively Bind Activated CA Domain of CA IX As used herein, "normoxia" is defined as oxygen tension levels in a specific vertebrate tissue that are within the normal ranges of physiological oxygen tension levels for that tissue. As used herein, "hypoxia" is defined as an oxygen tension level necessary to stabilize HIF-1α in a specific tissue or cell. Experimentally-induced hypoxia is generally in the range of 2% $pO_2$ or below, but above anoxia (0% $pO_2$, as anoxia would be lethal). The examples described herein that concern hypoxia were performed at 2% $pO_2$ which is an exemplary hypoxic condition. However, ones of skill in the art would expect other oxygen tension levels to be understood as "hypoxic" and to produce similar experimental results. For example, Wykoff et al. [121] used a condition of 0.1% $pO_2$ as representative of hypoxia to induce HIF-1α-dependent expression of CA9. Tomes et al. has demonstrated varying degrees of HIF-1α stabilization and CA9 expression in HeLa cells or primary human breast fibroblasts under exemplary in vitro hypoxic conditions of 0.3%, 0.5% and 2.5% $pO_2$ [Tomes et al., *Br. Cancer Res. Treat.*, 81(1): 61-69 (2003)]. Alternatively, Kaluz et al. has used the exemplary hypoxic condition of 0.5% $pO_2$ for experimental induction of CA9 [Kaluz et al., *Cancer Res.*, 63: 917-922 (2003)] and referred to "experimentally-induced ranges" of hypoxia as 0.1-1% $pO_2$ [129].

Oxygen tension levels above 2% $pO_2$ may also be hypoxic, as shown by Tomes et al., supra. One of skill in the art would be able to determine whether a condition is hypoxic as defined herein, based on a determination of HIF-1α stabilization. Exemplary ranges of hypoxia in a specific tissue or cell may be, for example, between about 3% to about 0.05% $pO_2$, between about 2% to about 0.1% $pO_2$, between about 1% to about 0.1% $pO_2$, and between about 0.5% to about 0.1% $pO_2$.

"Mild hypoxia" is defined herein as an oxygen tension level in a specific vertebrate tissue that does not stabilize HIF-1α and is below normoxia. Mild hypoxia would be understood by those of skill in the art to be below normoxia but still above hypoxia.

As has been previously reported by the inventors and others, CA IX can be expressed by alternative mechanisms, at least in vitro: a hypoxia-regulated pathway which requires HIF-1α stabilization, and a phosphatidylinositol 3' kinase (PI3K) pathway occurring at high cell density, which requires a minimal level of HIF-1α and a lowered oxygen concentration that is, however, above that necessary for HIF-1α stabilization [129]. Cell crowding may lead to pericellular mild hypoxia; for example, in dense LNCaP human prostate carcinoma cells 48 hours after plating, oxygen tension was 9% $pO_2$ above the cell surface, compared with 13% $pO_2$ above sparse cells, and compared with 0.1-1% $pO_2$ frequently used in experimentally induced hypoxic responses [Sheta et al., *Oncogene*, 20: 7624-7634 (2001)]. The cell density-dependent induction of CA IX may explain CA IX expression in areas adjacent to hypoxic regions in solid tumors, and the selectivity of the CA IX-specific inhibitors for hypoxicallyinduced CA IX may be exploited to differentiate between the two mechanisms diagnostically, prognostically and therapeutically.

The CA IX-specific inhibitors which selectively bind the activated form of CA IX can be used, for example, in laboratory diagnostics, using fluorescence microscopy or histochemical staining; as a component in assays for detecting and/or quantitating MN antigen in, for example, clinical samples; in electron microscopy with colloid gold beads for localization of MN proteins and/or polypeptides in cells; and in genetic engineering for cloning the MN gene or fragments thereof, or related cDNA. Such activated CA IX-specific inhibitors can be used as components of diagnostic/prognostic kits, for example, for in vitro use on histological sections; such inhibitors can be labeled appropriately, as with a suitable radioactive isotope, and used in vivo to locate metastases by scintigraphy. Further such inhibitors may be used in vivo therapeutically to treat cancer patients with or without toxic and/or cytostatic agents attached thereto. Further, such inhibitors can be used in vivo to detect the presence of neoplastic and/or pre-neoplastic disease. Still further, such inhibitors can be used to affinity purify MN proteins and polypeptides.

Such CA IX-specific inhibitors which selectively bind activated CA IX could be used in combination with other compounds which bind to any forms of CA IX, in order to differentiate between hypoxic and nonhypoxic expression of CA IX. For example, such methods could comprise the immunohistochemical use of a CA IX-specific sulfonamide, such as compound 92, and an antibody which binds to the PG domain of CA IX, such as the M75 Mab. If a tissue overexpresses CA IX, as indicated by M75 Mab binding, but such CA IX is not activated, as indicated by lack of CAI sulfonamide binding, it would indicate that the CA IX expression is induced by a nonhypoxic condition which elevates CA IX levels, such as by cell density-dependent induction of CA IX mediated by phosphatidylinositol 3'-kinase (PI3K). Alternatively, the methods of the invention could comprise the use of an antibody which specifically binds the activated form of the CA domain of CA IX, in combination with an antibody which binds to another domain of CA IX, such as the Mab M75 which binds to the PG domain, in order to differentiate between hypoxic and nonhypoxic expression of CA IX.

Such information may be useful as a method of indicating degrees of lowered oxygen tension; for example, at intermediate oxygen tension levels (for example, such as between 9% and 5% $pO_2$), CA IX may be induced, but not activated, and may be detected only by the MAb M75; whereas at hypoxic $pO_2$ levels (such as 2% or less), CA IX protein/polypeptide may be both expressed and activated, and detectable by both the Mab M75 and by a CAI sulfonamide which specifically binds the activated CA domain of CA IX. Thus, detection of both the presence of CA IX and its specific binding by CA IX-specific CAIs can be used in combination as a noninvasive method to determine $pO_2$ levels of a tissue. Such information may be useful diagnostically/prognostically or in patient therapy selection, depending upon which CA IX functions are targeted. For example, in in vitro RNA interference studies, expression of CA IX under both normoxia and hypoxia promoted tumor growth, in additive effects [138]. Those data along with the present invention implicate more than one CA IX function as promoting tumor growth. Radiobiologically relevant tumor hypoxia appears to occur at lower oxygen tension levels, such as at 2% $pO_2$ or lower, which oxygen tension levels may induce activated CA IX expression that is detectable by CA IX-specific inhibitors. It is possible that tumors that express CA IX constitutively because of deregulation [such as deregulated PI3K activity; 129] may be distinguished by the CA IX being detectable by the Mab M75 but not by CA IX-specific inhibitors (because the CA domain is overexpressed but not activated).

Materials and Methods

General. Melting points: heating plate microscope (not corrected); IR spectra: KBr pellets, 400-4000 $cm^{-1}$ Perkin-Elmer 16PC FTIR spectrometer; $^1$H-NMR spectra: Varian 300CXP apparatus (chemical shifts are expressed as δ values relative to $Me_4Si$ as standard); Elemental analysis: Carlo Erba Instrument CHNS Elemental Analyzer, Model 1106. All reactions were monitored by thin-layer chromatography (TLC) using 0.25-mm precoated silica gel plates (E. Merck). Pyrylium salts were prepared by literature procedures, generally by olefin (or their precursors) bisacylation, as described in the literature [6, 26, 108], whereas aminobenzolamide as described earlier [97]. Other sulfonamides used as standards were commercially available.

General Procedure for the Preparation of Compounds 71-91 (Pyridinium Derivatives of Aminobenzolamide)

An amount of 2.9 mM of aminobenzolamide [97] and 2.9 mM of pyrylium salt II (depicted in FIG. 5) were suspended in 5 mL of anhydrous methanol and poured into a stirred mixture of 14.5 mM of triethylamine and 5.8 mM of acetic anhydride. After five minutes of stirring, another 10 mL of methanol were added to the reaction mixture, which was heated to reflux for 15 min. Then 14.5 mM of acetic acid was added and heating was continued for 2-5 hours. The role of the acetic anhydride is to react with the water formed during the condensation reaction between the pyrylium salt and the aromatic amine, in order to shift the equilibrium towards the formation of the pyridinium salts of the general formula (B) (shown above). In the case of aminobenzolamide, this procedure is the only one which gave acceptable yields in pyridinium salts, probably due to the deactivating effect of the sulfamoylaminothiadiazole moiety on the amine group, which becomes poorly nucleophilic and unreactive towards these reagents. The precipitated pyridinium salts obtained were purified by treatment with concentrated ammonia solution (which also converts the eventually unreacted pyrylium salt to the corresponding pyridine which is soluble in acidic medium), reprecipitation with perchloric acid and recrystallization from water with 2-5% $HClO_4$.

Purification of Catalytic Domain of CA IX

The cDNA of the catalytic domain of hCA IX (isolated as described by Pastorek et al. [72]) was amplified by using PCR and specific primers for the vector pCAL-n-FLAG (from Stratagene). The obtained construct was inserted in the pCAL-n-FLAG vector and then cloned and expressed in *Escherichia coli* strain BL21-GOLD(DE3) (from Stratagene). The bacterial cells were lysed and homogenated in a buffered solution (pH 8) of 4 M urea and 2% Triton X-100, as described by Wingo et al. [116]. The homogenate thus obtained was extensively centrifuged in order to remove soluble and membrane associated proteins as well as other cellular debris. The resulting pellet was washed by repeated homogenation and centrifugation in water, in order to remove the remaining urea and Triton X-100. Purified CA IX inclusion bodies were denaturated in 6 M guanidine hydrochloride and refolded into the active form by snap dilution into a solution of 100 mM MES (pH 6), 500 mM L-arginine, 2 mM $ZnCl_2$, 2 mM EDTA, 2 mM reduced glutathione, 1 mM oxidized glutathione. Active hCA IX was extensively dialysed into a solution of 10 mM Hepes (pH 7.5), 10 mM Tris HCl, 100 mM $Na_2SO_4$ and 1 mM $ZnCl_2$. The amount of protein was determined by spectrophometric measurements and its activity by stopped-flow measurements, with $CO_2$ as substrate [44]. Optionally, the protein was further purified by sulfonamide affinity chromatography [44], the amount of enzyme was determined by spectrophometric measurements and its activity by stopped-flow measurements, with $CO_2$ as substrate [44].

CA I, II and IV Purification

Human CA I and CA II cDNAs were expressed in *Escherichia coli* strain BL21 (DE3) from the plasmids pACA/hCA I and pACA/hCA II described by Lindskog's group [54]. Cell growth conditions were those described in ref. [12], and enzymes were purified by affinity chromatography according to the method of Khalifah et al. [45]. Enzyme concentrations were determined spectrophotometrically at 280 nm, utilizing a molar absorptivity of 49 $mM^{-1}.cm^{-1}$ for CA I and 54 $mM^{-1}.cm^{-1}$ for CA II, respectively, based on $M_r$=28.85 kDa for CA I, and 29.3 kDa for CA II, respectively [53, 84]. CA IV was isolated from bovine lung microsomes as described by Maren et al, and its concentration has been determined by titration with ethoxzolamide [59].

Enzyme Assays

CA $CO_2$ Hydrase Activity Assay

An SX.18MV-R Applied Photophysics stopped-flow instrument has been used for assaying the CA $CO_2$ hydration activity assays [44]. A stopped flow variant of the Poker and Stone spectrophotometric method [76] has been employed, using an SX.18MV-R Applied Photophysics stopped flow instrument, as described previously [43]. Phenol red (at a concentration of 0.2 mM) has been used as indicator, working at the absorbance maximum of 557 nm, with 10 mM Hepes (pH 7.5) as buffer, 0.1 M $Na_2SO_4$ (for maintaining constant the ionic strength), following the CA-catalyzed $CO_2$ hydration reaction for a period of 10-100 s. Saturated $CO_2$ solutions in water at 20° C. were used as substrate [44]. Stock solutions of inhibitor (1 mM) were prepared in distilled-deionized water with 10-20% (v/v) DMSO (which is not inhibitory at these concentrations) and dilutions up to 0.01 nM were done thereafter with distilled-deionized water. Inhibitor and enzyme solutions were preincubated together for 10 min at room temperature prior to assay, in order to allow for the formation of the E-I complex. Triplicate experiments were done for each inhibitor concentration, and the values reported throughout the paper are the mean of such results.

CA Esterase Activity Assay

Initial rates of 4-nitrophenylacetate hydrolysis catalysed by different CA isozymes were monitored spectrophotometrically, at 400 nm, with a Cary 3 instrument interfaced with an IBM compatible PC [76]. Solutions of substrate were prepared in anhydrous acetonitrile; the substrate concentrations varied between $2.10^{-2}$ and $1.10^{-6}$ M, working at 25° C. A molar absorption coefficient $\epsilon$ of 18,400 $M^{-1}.cm^{-1}$ was used for the 4-nitrophenolate formed by hydrolysis, in the conditions of the experiments (pH 7.40), as reported in the literature [76]. Non-enzymatic hydrolysis rates were always subtracted from the observed rates. Triplicate experiments were done for each inhibitor concentration, and the values reported throughout the paper are the mean of such results. Stock solutions of inhibitor (1-3 mM) were prepared in distilled-deionized water with 10-20% (v/v) DMSO (which is not inhibitory at these concentrations) and dilutions up to 0.01 nM were done thereafter with distilled-deionized water. Inhibitor and enzyme solutions were preincubated together for 10 min at room temperature prior to assay, in order to allow for the formation of the E-I complex. The inhibition constant $K_I$ was determined as described in references [44, 76].

Membrane Permeance Assay: Ex Vivo Penetration Through Red Blood Cells

An amount of 10 mL of freshly isolated human red cells thoroughly washed several times with Tris buffer (pH 7.40, 5 mM) and centrifuged for 10 min were treated with 25 mL of a 2 mM solution of sulfonamide inhibitor. Incubation has been done at 37° C. with gentle stirring, for periods of 30-120 min. After the incubation times of 30, 60 and 120 min., respectively, the red cells were centrifuged again for 10 min, the supernatant discarded, and the cells washed three times with 10 mL of the above mentioned buffer, in order to eliminate all unbound inhibitor [81, 96, 98]. The cells were then lysed in 25 mL of distilled water, centrifuged for eliminating membranes and other insoluble impurities. The obtained solution was heated at 100° C. for 5 minutes (in order to denature CA-s) and sulfonamides possibly present have been assayed in each sample by three methods: a HPLC method [36]; spectrophotometrically [4] and enzymatically [76].

HPLC: A variant of the methods of Gomaa [36] has been developed by us, as follows: a commercially available 5 µm Bondapak C-18 column was used for the separation, with a mobile phase made of acetonitrile—methanol—phosphate buffer (pH 7.4) 10:2:88 (v/v/v), at a flow rate of 3 mL/min, with 0.3 mg/mL sulphadiazine (Sigma) as internal standard. The retention times were: 12.69 min for acetazolamide; 4.55 min for sulphadiazine; 10.54 min for benzolamide; 12.32 min for aminobenzolamide; 3.15 min for 71; 4.41 min for 76; 3.54 min for 89; and 4.24 min for 91. The eluent was monitored continuously for absorbance (at 254 nm for acetazolamide, and wavelength in the range of 270-310 nm in the case of the other sulfonamides.

Spectrophotometrically: A variant of the pH-induced spectrophotometric assay of Abdine et al. [4] has been used, working for instance at 260 and 292 nm, respectively, for acetazolamide; at 225 and 265 nm, respectively, for sulfanilamide, etc. Standardized solutions of each inhibitor have been prepared in the same buffer as the one used for the membrane penetrability experiments.

Enzymatically: the amount of sulfonamide present in the lysate has been evaluated based on hCA II inhibition measured with the esterase method, as described above [76]. Standard inhibition curves have been obtained previously for each sulfonamide, using the pure compound, which were used thereafter for determining the amount of inhibitor present in the lysate. Mention should be made that the three methods presented above led to results in good agreement, within the limits of the experimental errors.

Statistical analysis: Values are expressed ±standard error of measurement. Statistical significance was determined using an unpaired t-test with p<0.05 considered significant.

The following materials and methods were used for Examples 4-8.

Cell Culture

MDCK, SiHa, HeLa cells and their transfected derivatives were grown in DMEM with 10% FCS and buffered with 22.3 mM bicarbonate [103]. To maintain the standard conditions, the cells were always plated in 3 ml of culture medium at a density of $0.8-1\times10^6$ per 6 cm dish 24 hours before the transfer to hypoxia (2% $O_2$ and 5% $CO_2$ balanced with $N_2$) generated in a Napco 7000 incubator. Parallel normoxic dishes were incubated in air with 5% $CO_2$. At the end of each experiment, the pH of the culture medium was immediately measured, the medium was harvested for the determination of the lactic acid content with the standard assay kit (Sigma), the cells were counted to ensure that the resulting cultures were comparable, and then processed either for immunofluorescence or extracted for immunoprecipitation and/or immunoblotting.

Sulfonamide Synthesis and Treatment of Cells

Compound 6 sulfonamide [4-(2-aminoethyl)-benzenesulfonamide] was from Sigma-Aldrich. The membrane-impermeable Compound 39 [4-(2,4,6-trimethylpyridinium-N-methylcarboxamido)-benzenesulfonamide perchlorate] was prepared by reaction of homosulfanilamide with 2,4,6-trimethylpyrilium perchlorate [81]. Compound 92 [the fluorescent derivative of Compound 5 sulfonamide] was obtained from homosulfanilamide and fluorescein isothiocyanate [142]. CAIs showed the following $K_I$ values assessed by $CO_2$ hydration methods using the purified CA domain of CA IX: Compound 6 36 nM, Compound 39 38 nM and Compound 92 24 nM. The sulfonamides were dissolved in PBS with 20% DMSO at 100 mM concentration and diluted in a culture medium to a required final concentration just before their addition to cells. The cells were incubated for 48 hours in hypoxia and normoxia, respectively, the pH of the culture medium was measured and the binding of the FITC-labeled Compound 92 to living cells, washed three times with PBS, was viewed by a Nikon E400 epifluorescence microscope.

Cloning of CA IX Mutants and Transfection

Cloning of CA IX deletion mutants lacking either the N-terminal PG domain or the central CA domain was performed as described [73, 145]. MDCK and HeLa cell lines constitutively expressing CA IX protein or its mutants were obtained by cotransfection of recombinant plasmids pSG5C-CA IX, pSG5C-ΔCA and pSG5C-ΔPG with pSV2neo plasmid in 10:1 ratio using a GenePorter II transfection kit from Gene Therapy Systems. The transfected cells were subjected to selection in 500-1000 μg/ml G418, cloned, tested for CA IX and expanded. At least three clonal cell lines expressing each CA IX form were analyzed to eliminate the effect of clonal variation. The cells cotransfected with empty pSG5C and pSV2 neo were used as negative controls.

Indirect Immunofluorescence and Immunoblotting

Cells grown on glass coverslips were fixed in ice-cold methanol at −20° C. for 5 min and stained with CA IX-specific MAb M75 directed to the PG domain or V/10 directed to the CA domain followed by FITC-labeled secondary antibodies [73, 145]. For immunoblotting, cells were rinsed with PBS and extracted in RIPA buffer for 30 min on ice. Protein concentrations were quantified using the BCA kit (Pierce). The proteins (50 μg/lane) were resolved in 10% SDS-PAGE under reducing and non-reducing conditions, respectively, transferred to PVDF membrane and CA IX was detected with the specific MAbs as described [73].

Cell Biotinylation and Immunoprecipitation

Cells were washed with ice-cold buffer A (20 mM sodium hydrogen carbonate, 0.15 M NaCl, pH 8.0), incubated for 60 min at 4° C. with buffer A containing 1 mg of NHS-LC-Biotin (Pierce), then washed 5 times with buffer A and extracted in RIPA as described above. MAb V/10 (deposited at the BCCM™/LMBP Plasmid Collection Laboratorium, Gent, Belgium under Accession No. LMBP 6009CB) in 1 ml of hybridoma medium was bound to 25 μl 50% suspension of Protein-A Sepharose (Pharmacia) for 2 h at RT. Biotinylated extract (200 μl) was pre-cleared with 20 μl of 50% suspension of Protein-A Sepharose and then added to the bound MAb. Immunocomplexes collected on the Protein-A Sepharose were separated by SDS-PAGE, transferred to a PVDF membrane and revealed with peroxidase-conjugated streptavidin (1/1000, Pierce) followed by enhanced chemoluminiscence.

The following examples are for purposes of illustration only and are not meant to limit the invention in any way.

Example 1

Inhibition of the Tumor-Associated Isozyme IX with Aromatic and Heterocyclic Sulfonamides The inhibition of the tumor-associated transmembrane carbonic anhydrase IX (CA IX) isozyme has been investigated with a series of aromatic and heterocyclic sulfonamides, including the six clinically used derivatives acetazolamide, methazolamide, ethoxzolamide, dichlorophenamide, dorzolamide and brinzolamide. Inhibition data for the physiologically relevant isozymes I and II (cytosolic forms) and IV (membrane-bound) were also provided for comparison.

Chemistry. Sulfonamides investigated for the inhibition of the tumor-associated isozyme CA IX, of types 1-26 are shown in FIG. 4A-B. Compounds 1-6, 11-12, 20 and 26 are commercially available, whereas 7-10 [43], 13-19 [24, 79, 90, 97] and 21-25 [79] were prepared as reported earlier. The six clinically used compounds were also assayed, since no such data are available in the literature.

CA inhibition data. Inhibition data against four CA isozymes, CA I, II, IV and IX [44, 72, 116], with the above mentioned compounds I-26 and the six clinically used inhibitors, are shown in Table 1.

TABLE 1

CA I, II, IV and IX inhibition data with sulfonamides 1-26 and clinically used inhibitors.

| | $K_I$* (nM) | | | |
|---|---|---|---|---|
| Inhibitor | hAC I[a] | hCA II[a] | bCA IV[b] | hCA IX[c] |
| 1 | 45400 | 295 | 1310 | 33 |
| 2 | 25000 | 240 | 2200 | 238 |
| 3 | 28000 | 300 | 3000 | 294 |
| 4 | 78500 | 320 | 3215 | 305 |
| 5 | 25000 | 170 | 2800 | 103 |
| 6 | 21000 | 160 | 2450 | 33 |
| 7 | 8300 | 60 | 180 | 245 |
| 8 | 9800 | 110 | 320 | 264 |
| 9 | 6500 | 40 | 66 | 269 |
| 10 | 6000 | 70 | 125 | 285 |
| 11 | 5800 | 63 | 154 | 24 |
| 12 | 8400 | 75 | 160 | 39 |
| 13 | 8600 | 60 | 540 | 41 |
| 14 | 9300 | 19 | 355 | 30 |
| 15 | 6 | 2 | 5 | 38 |
| 16 | 164 | 46 | 129 | 34 |
| 17 | 185 | 50 | 144 | 20 |
| 18 | 109 | 33 | 72 | 31 |
| 19 | 95 | 30 | 72 | 24 |
| 20 | 690 | 12 | 154 | 16 |
| 21 | 55 | 8 | 17 | 14 |
| 22 | 21000 | 125 | 415 | 32 |
| 23 | 23000 | 133 | 438 | 30 |

TABLE 1-continued

CA I, II, IV and IX inhibition data with sulfonamides 1-26 and clinically used inhibitors.

| Inhibitor | $K_I^*$ (nM) | | | |
|---|---|---|---|---|
| | hAC I[a] | hCA II[a] | bCA IV[b] | hCA IX[c] |
| 24 | 24000 | 125 | 560 | 21 |
| 25 | 18000 | 110 | 450 | 22 |
| 26 | 135 | 40 | 86 | 26 |
| AAZ | 250 | 12 | 70 | 25 |
| MZA | 50 | 14 | 36 | 27 |
| EZA | 25 | 8 | 13 | 34 |
| DCP | 1200 | 38 | 380 | 50 |
| DZA | 50000 | 9 | 43 | 52 |
| BRZ | — | 3 | 45 | 37 |

[a]Human cloned isozymes, esterase assay method [76];
[b]Isolated from bovine lung microsomes, esterase assay method [76];
[c]Human cloned isozyme, $CO_2$ hydrase assay method [44, 72, 116].

We report here the first inhibition study of the tumor-associated, transmembrane isozyme CA IX with a series of aromatic and heterocyclic sulfonamides, including also the six clinically used derivatives acetazolamide, methazolamide, ethoxzolamide, dichlorophenamide, dorzolamide and brinzolamide. Inhibition data for the physiologically relevant isozymes I and II (cytosolic forms) and IV (membrane-bound) are also provided for comparison. Very interesting inhibition profile against CA IX with these sulfonamides has been detected, which is a promising discovery for the potential design of CA IX-specific inhibitors, with applications as antitumor agents. Several nanomolar CA IX inhibitors have been detected, both among the aromatic (such as orthanilamide, homosulfanilamide, 4-carboxy-benzenesulfonamide, 1-naphthalene-sulfonamide and 1,3-benzenedisulfonamide derivatives) as well as the heterocyclic (such as 1,3,4-thiadiazole-2-sulfonamide, benzothiazole-2-sulfonamide, etc.) sulfonamides investigated.

Example 2

The First Selective, Membrane-Impermeant Inhibitors Targeting the Tumor-Associated Isozyme IX Up to now no CA IX inhibition studies with this type of membrane-impermeant CAIs have been reported. Thus, we decided to explore some of the pyridinium derivatives of general formula (A) for their interaction with the catalytic domain of tumor-associated isozyme IX, recently cloned and purified by the inventors [33, 43, 114, 115, 117], as well as the cytosolic, physiologically relevant isozymes CA I, II and the membrane-anchored isozyme CA IV [88, 96].

The inhibition of the tumor-associated transmembrane carbonic anhydrase IX (CA IX) isozyme has been investigated with a series of positively-charged, pyridinium derivatives of sulfanilamide, homosulfanilamide and 4-aminoethyl-benzenesulfonamide. Inhibition data for the physiologically relevant isozymes I and II (cytosolic forms) and IV (membrane-bound) were also provided for comparison. This is the first report of inhibitors that may selectively target CA IX, due to their membrane-impermeability and high affinity for this clinically relevant isozyme.

CA Inhibition

Data of Table 2 clearly show that most of the compounds 27-70 act as efficient CA IX inhibitors, and that their affinity for this isozyme differs considerably as compared to affinities for the cytosolic isozymes CA I and II, and the other membrane-associated isozyme investigated, CA IV.

In a series of substituted-pyridinium derived sulfanilamides, homosulfanilamides and p-aminoethylbenzenesulfonamides, a large number of effective hCA IX inhibitors were detected. Some low nanomolar CA IX inhibitors were reported for the first time. Since these compounds are membrane-impermeant due to their salt-like character, and as hCA IX is present on the extracellular side of many tumors with poor clinical prognosis, compounds of this type target specifically this tumor-associate CA isozyme without affecting the cytosolic CAs known to play important physiological functions. Thus, compounds of this type may constitute the basis of new anticancer therapies based on CA inhibitors.

TABLE 2

Inhibition of isozymes hCA I, hCA II, bCA IV and hCA IX with the pyridinium salts 27-70.

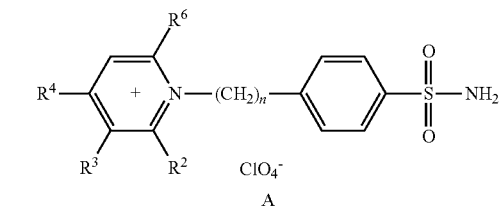

A

| Compound | R[2] | R[3] | R[4] | R[6] | hCA I[a] $K_I^*$ (μM) | hCA II[a] $K_I^*$ (nM) | bCA IV[b] $K_I^*$ (nM) | hCA IX[c] $K_I^*$ (nM) |
|---|---|---|---|---|---|---|---|---|
| 27 | Me | H | Me | Me | 10 | 150 | 290 | 165 |
| 28 | Me | H | Ph | Me | 7 | 60 | 211 | 48 |
| 29 | Et | H | Ph | Et | 6 | 60 | 182 | 43 |
| 30 | n-Pr | H | Ph | n-Pr | 10 | 120 | 194 | 178 |
| 31 | i-Pr | H | Ph | i-Pr | 5 | 50 | 90 | 160 |
| 32 | Me | H | Ph | Ph | 40 | 210 | 852 | 280 |
| 33 | Et | H | Ph | Ph | 43 | 400 | 1300 | 450 |
| 34 | n-Pr | H | Ph | Ph | 140 | 580 | 1483 | >500 |
| 35 | i-Pr | H | Ph | Ph | 125 | 440 | 2102 | >500 |

TABLE 2-continued

Inhibition of isozymes hCA I, hCA II, bCA IV and hCA IX with the pyridinium salts 27-70.

[Structure A: pyridinium salt with $R^2$, $R^3$, $R^4$, $R^6$ substituents, N-(CH$_2$)$_n$-phenyl-SO$_2$NH$_2$, ClO$_4^-$ counterion]

| Compound | $R^2$ | $R^3$ | $R^4$ | $R^6$ | hCA I$^a$ (μM) | hCA II$^a$ (nM) | bCA IV$^b$ (nM) | hCA IX$^c$ (nM) |
|---|---|---|---|---|---|---|---|---|
| 36 | n-Bu | H | Ph | Ph | 305 | 620 | 2155 | >500 |
| 37 | Ph | H | Ph | Ph | 290 | 510 | 2500 | >500 |
| 38 | Me | Me | Me | Me | 5 | 40 | 61 | 72 |
| 39 | Me | H | Me | Me | 7 | 50 | 92 | 38 |
| 40 | i-Pr | H | Me | Me | 6 | 50 | 80 | 42 |
| 41 | i-Pr | H | Me | i-Pr | 11 | 80 | 144 | 54 |
| 42 | Me | H | Ph | Me | 4 | 20 | 70 | 26 |
| 43 | Et | H | Ph | Et | 2 | 21 | 52 | 29 |
| 44 | n-Pr | H | Ph | n-Pr | 24 | 90 | 163 | 230 |
| 45 | i-Pr | H | Ph | i-Pr | 12 | 61 | 101 | 100 |
| 46 | Me | H | Ph | Ph | 32 | 121 | 161 | 64 |
| 47 | Et | H | Ph | Ph | 42 | 314 | 983 | 79 |
| 48 | n-Pr | H | Ph | Ph | 130 | 390 | 1260 | 85 |
| 49 | i-Pr | H | Ph | Ph | 112 | 370 | 1214 | 80 |
| 50 | n-Bu | H | Ph | Ph | 300 | 595 | 2104 | 135 |
| 51 | t-Bu | H | Ph | Ph | 110 | 321 | 1070 | >500 |
| 52 | Ph | H | Ph | Ph | 280 | 472 | 1956 | 120 |
| 53 | Ph | H | H | Ph | 280 | 493 | 1954 | 106 |
| 54 | Me | Me | Me | Me | 3 | 30 | 51 | 35 |
| 55 | Me | H | Me | Me | 4 | 21 | 60 | 14 |
| 56 | i-Pr | H | Me | Me | 2 | 15 | 32 | 31 |
| 57 | i-Pr | H | Me | i-Pr | 3 | 20 | 70 | 49 |
| 58 | Me | H | Ph | Me | 1 | 8 | 20 | 6 |
| 59 | Et | H | Ph | Et | 1 | 9 | 21 | 8 |
| 60 | n-Pr | H | Ph | n-Pr | 7 | 42 | 82 | 205 |
| 61 | i-Pr | H | Ph | i-Pr | 6 | 21 | 70 | 89 |
| 62 | Me | H | Ph | Ph | 18 | 103 | 144 | 37 |
| 63 | Et | H | Ph | Ph | 40 | 220 | 761 | 70 |
| 64 | n-Pr | H | Ph | Ph | 112 | 270 | 1055 | 84 |
| 65 | i-Pr | H | Ph | Ph | 94 | 350 | 864 | 78 |
| 66 | n-Bu | H | Ph | Ph | 290 | 544 | 2008 | 120 |
| 67 | t-Bu | H | Ph | Ph | 92 | 275 | 1000 | >500 |
| 68 | Ph | H | Ph | Ph | 270 | 419 | 1830 | 95 |
| 69 | Ph | H | H | Ph | 265 | 420 | 1905 | 81 |
| 70 | Me | Me | Me | Me | 2 | 10 | 21 | 8 |
| acetazolamide | | | | | 0.25 | 12 | 70 | 25 |
| methazolamide | | | | | 0.05 | 14 | 36 | 27 |
| dichlorophenamide | | | | | 1.2 | 38 | 380 | 50 |
| indisulam | | | | | 0.03 | 15 | 65 | 24 |

$^a$Human (cloned) isozymes; $^b$From bovine lung microsomes; $^c$Catalytic domain of the human, cloned isozyme.
*errors in the range of ± 10% of the reported value, from three different determinations.
For compounds 27-38: n = 0; 39-54: n = 1; 55-70: n = 2

Example 3

Design of Selective, Membrane-Impermeant Heterocyclic Sulphonamide Inhibitors Targeting the Human Tumor-Associated Isozyme IX A series of positively-charged sulfonamides were obtained by reaction of aminobenzolamide (5-(4-aminobenzenesulfonylamino)-1,3,4-thiadiazole-2-sulfonamide) with tri-/tetra-substituted pyrilium salts possessing alkyl-, aryl- or combinations of alkyl and aryl groups at the pyridinium ring. These new compounds are membrane-impermeant due to their salt-like character and were assayed for the inhibition of four physiologically relevant carbonic anhydrase (CA, EC 4.2.1.1) isozymes, the cytosolic hCA I and II, the membrane-anchored bCA IV and the membrane-bound, tumor associated isozyme hCA IX. The high affinity of these new derivatives for the tumor-associated isozyme CA IX and their membrane impermeability, make this type of CA inhibitors interesting candidates for the selective inhibition of only the tumor associated isozyme and not the cytosolic ones, for which they also show high potency.

Results

CA inhibition. Inhibition data against isozymes I, II, IV and IX with compounds 71-91 reported here are shown in Table 3.

TABLE 3

Inhibition of isozymes hCA I, hCA II, bCA IV and hCA IX with the pyridinium salts 71-91.

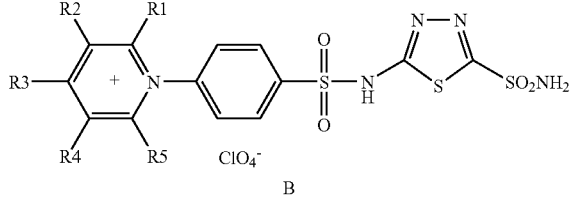

B

| | $R^1$ | $R^2$ | $R^3$ | $R^4$ | $R^5$ | hCA I[a] | hCA II[a] | bCA IV[b] | hCA IX[c] |
|---|---|---|---|---|---|---|---|---|---|
| 71 | Me | H | Me | H | Me | 4 | 0.26 | 2.1 | 3 |
| 72 | i-Pr | H | Me | H | Me | 4 | 0.39 | 3.0 | 5 |
| 73 | i-Pr | H | Me | H | i-Pr | 7 | 1.54 | 4.7 | 16 |
| 74 | t-Bu | H | Me | H | t-Bu | 11 | 3.13 | 9.4 | 34 |
| 75 | Me | H | Ph | H | Me | 3 | 0.20 | 2.0 | 6 |
| 76 | Et | H | Ph | H | Et | 4 | 0.21 | 2.3 | 9 |
| 77 | n-Pr | H | Ph | H | n-Pr | 9 | 3.45 | 8.1 | 35 |
| 78 | n-Bu | H | Ph | H | n-Bu | 10 | 4.62 | 10.3 | 40 |
| 79 | i-Pr | H | Ph | H | i-Pr | 5 | 1.61 | 4.1 | 30 |
| 80 | Me | H | Ph | H | Ph | 4 | 1.21 | 3.0 | 24 |
| 81 | Et | H | Ph | H | Ph | 5 | 1.14 | 3.8 | 29 |
| 82 | n-Pr | H | Ph | H | Ph | 8 | 3.90 | 6.0 | 40 |
| 83 | i-Pr | H | Ph | H | Ph | 6 | 3.74 | 4.5 | 32 |
| 84 | n-Bu | H | Ph | H | Ph | 8 | 4.95 | 8.4 | 45 |
| 85 | t-Bu | H | Ph | H | Ph | 12 | 4.11 | 7.0 | 43 |
| 86 | Ph | H | Me | H | Ph | 6 | 4.78 | 5.8 | 12 |
| 87 | Ph | H | Ph | H | Ph | 5 | 5.96 | 5.6 | 12 |
| 88 | Ph | H | H | H | Ph | 5 | 4.93 | 5.4 | 16 |
| 89 | Me | Me | Me | H | Me | 3 | 0.30 | 2.4 | 5 |
| 90 | Me | Me | Ph | H | Me | 3 | 1.24 | 5.2 | 15 |
| 91 | Me | $R^3, R^5 =$ $(CH_2)_9$; $R^4 = $Me | | | Me | 3 | 1.37 | 4.6 | 12 |
| aminobenzolamide | | | | | | 6 | 2.04 | 5.1 | 38 |
| acetazolamide | | | | | | 250 | 12 | 70 | 25 |
| methazolamide | | | | | | 50 | 14 | 36 | 27 |
| dichlorophenamide | | | | | | 1200 | 38 | 380 | 50 |
| indisulam | | | | | | 30 | 15 | 65 | 24 |

[a]Human (cloned) isozymes, esterase assay method [76].
[b]From bovine lung microsomes, esterase assay method [76].
[c]Catalytic domain of the human, cloned isozyme, $CO_2$ hydrase assay method [44].
*Errors in the range of ± 10% of the reported value, from three different determinations.

Ex vivo penetration through red blood cells. Levels of sulfonamides in red blood cells after incubation of human erythrocytes with millimolar solutions of inhibitor for 30-60 min (both classical as well as positively-charged sulfonamides were used in such experiments) are shown in Table 4 [4, 12, 36, 45, 53, 54, 58, 59, 84, 116, 118].

TABLE 4

Levels of sulfonamide CA inhibitors (µM) in red blood cells at 30 and 60 min, after exposure of 10 mL of blood to solutions of sulfonamide (2 mM sulfonamide in 5 mM Tris buffer, pH 7.4). The concentrations of sulfonamide has been determined by three methods: HPLC; electronic spectroscopy (ES) and the enzymatic method (EI) - see Experimental for details.

| | [sulfonamide], µM* | | | | | |
|---|---|---|---|---|---|---|
| | t = 30 min | | | t = 60 min | | |
| Inhibitor | HPLC[a] | ES[b] | EI[c] | HPLC[a] | ES[b] | EI[c] |
| AAZ | 136 | 139 | 140 | 160 | 167 | 163 |
| MZA | 170 | 169 | 165 | 168 | 168 | 167 |
| Benzolamide | 110 | 108 | 112 | 148 | 146 | 149 |
| Aminobenzolamide | 125 | 127 | 122 | 154 | 156 | 158 |
| 71 | 0.3 | 0.5 | 0.5 | 0.4 | 0.5 | 0.3 |
| 76 | 1.0 | 1.1 | 1.0 | 1.1 | 1.2 | 1.1 |
| 89 | 0.3 | 0.2 | 0.5 | 0.3 | 0.6 | 0.4 |
| 91 | 0.4 | 0.3 | 0.5 | 0.3 | 0.6 | 0.5 |

*Standard error (from 3 determinations) <5% by:
[a]the HPLC method [36];
[b]the electronic spectroscopic method [4];
[c]the enzymatic method [76].

The new compounds reported in the present work were characterized by standard chemical and physical methods (elemental analysis, within ±0.4% of the theoretical values; IR and NMR spectroscopy) that confirmed their structure (see Materials and Methods and Table 5 below for details) and were assayed for the inhibition of isozymes hCA I, hCA II, bCA IV and hCA IX.

TABLE 5

Elemental analysis data for the compounds described in Example 3

| | | Elemental analysis data (calc./found) | | |
|---|---|---|---|---|
| No | Formula | % C | % H | % N |
| 71 | $C_{16}H_{18}N_5O_4S_3{}^+ClO_4{}^-$ | 35.59/35.32 | 3.36/3.62 | 12.97/12.93 |
| 72 | $C_{18}H_{22}N_5O_4S_3{}^+ClO_4{}^-$ | 38.06/37.95 | 3.90/4.16 | 12.33/12.18 |
| 73 | $C_{20}H_{26}N_5O_4S_3{}^+ClO_4{}^-$ | 40.30/39.99 | 4.40/4.54 | 11.75/11.63 |
| 74 | $C_{22}H_{30}N_5O_4S_3{}^+ClO_4{}^-$ | 42.34/42.56 | 4.84/4.76 | 11.22/11.03 |
| 75 | $C_{21}H_{20}N_5O_4S_3{}^+ClO_4{}^-$ | 41.89/42.02 | 3.35/3.03 | 11.63/11.48 |
| 76 | $C_{23}H_{24}N_5O_4S_3{}^+ClO_4{}^-$ | 43.84/43.88 | 3.84/3.62 | 11.11/10.95 |
| 77 | $C_{25}H_{28}N_5O_4S_3{}^+ClO_4{}^-$ | 45.62/45.60 | 4.29/4.36 | 10.64/10.50 |
| 78 | $C_{27}H_{32}N_5O_4S_3{}^+ClO_4{}^-$ | 47.26/47.45 | 4.70/4.89 | 10.21/10.14 |
| 79 | $C_{25}H_{28}N_5O_4S_3{}^+ClO_4{}^-$ | 45.62/45.49 | 4.29/4.18 | 10.64/10.61 |
| 80 | $C_{26}H_{22}N_5O_4S_3{}^+ClO_4{}^-$ | 47.02/46.79 | 3.34/3.33 | 10.55/10.23 |
| 81 | $C_{27}H_{24}N_5O_4S_3{}^+ClO_4{}^-$ | 47.82/47.73 | 3.57/3.73 | 10.33/10.40 |
| 82 | $C_{28}H_{26}N_5O_4S_3{}^+ClO_4{}^-$ | 48.59/48.83 | 3.79/3.91 | 10.12/10.24 |
| 83 | $C_{28}H_{26}N_5O_4S_3{}^+ClO_4{}^-$ | 48.59/48.27 | 3.79/3.82 | 10.12/10.05 |
| 84 | $C_{29}H_{28}N_5O_4S_3{}^+ClO_4{}^-$ | 49.32/49.59 | 4.00/4.23 | 9.92/9.67 |
| 85 | $C_{29}H_{28}N_5O_4S_3{}^+ClO_4{}^-$ | 49.32/49.16 | 4.00/3.94 | 9.92/9.71 |
| 86 | $C_{26}H_{22}N_5O_4S_3{}^+ClO_4{}^-$ | 47.02/47.25 | 3.34/3.18 | 10.55/10.46 |
| 87 | $C_{31}H_{24}N_5O_4S_3{}^+ClO_4{}^-$ | 51.27/51.50 | 3.33/3.60 | 9.64/9.67 |
| 88 | $C_{25}H_{20}N_5O_4S_3{}^+ClO_4{}^-$ | 46.19/46.28 | 3.10/2.95 | 10.77/10.67 |
| 89 | $C_{17}H_{20}N_5O_4S_3{}^+ClO_4{}^-$ | 36.86/36.72 | 3.64/3.53 | 12.64/12.45 |
| 90 | $C_{22}H_{22}N_5O_4S_3{}^+ClO_4{}^-$ | 42.89/42.70 | 3.60/3.84 | 11.37/11.15 |
| 91 | $C_{24}H_{32}N_5O_4S_3{}^+ClO_4{}^-$ | 44.34/44.57 | 4.96/4.99 | 10.77/10.51 |

Conclusions

We report here a general approach for the preparation of positively-charged, membrane-impermeant sulfonamide CA inhibitors with high affinity for the cytosolic isozymes CA I and CA II, as well as for the membrane-bound ones CA IV and CA IX. They were obtained by attaching substituted-pyridinium moieties to aminobenzolamide, a very potent CA inhibitor itself. Ex vivo studies showed the new class of inhibitors reported here to discriminate for the membrane-bound versus the cytosolic isozymes. Correlated with the low nanomolar affinity of some of these compounds for the tumor-associated isozyme CA IX, this report constitutes the basis of selectively inhibiting only the target, tumor-associated CA IX in vivo, whereas the cytosolic isozymes would remain unaffected.

Characterization of Compounds 71-91 (For Preparation, see Materials and Methods Section)

1-N-[5-Sulfamoyl-1,3,4-thiadiazol-2-yl-(aminosulfonyl-4-phenyl)]-2,4,6-trimethyl-pyridinium perchlorate 71: white crystals, mp >300° C.; IR (KBr), cm$^{-1}$ (bands in italics are due to the anion): 595, 625, 664, 787, 803, 884, 915, 1100, 1150, 1190, 1200, 1285, 1360, 1495, 1604, 3065; $^1$H-NMR (D$_2$O), δ, ppm: 3.08 (s, 6H, 2,6-Me$_2$); 3.11 (s, 3H, 4-Me); 7.30-8.06 (m, AA'BB', 4H, ArH from phenylene); 9.05 (s, 2H, ArH, 3,5-H from pyridinium); in this solvent the sulfonamido protons are not seen, being in fast exchange with the solvent. Anal $C_{16}H_{18}N_5O_4S_3{}^+ClO_4{}^-$ (C, H, N).

1-N-[5-Sulfamoyl-1,3,4-thiadiazol-2-yl-(aminosulfonyl-4-phenyl)]-2-iso-propyl-4,6-dimethylpyridinium perchlorate 72, colorless crystals, mp 29o-1° C.; IR (KBr), cm$^{-1}$: 625, 680, 720, 1100, 1165, 1330, 1640, 3020, 3235; $^1$H-NMR (TFA), δ, ppm: 1.50 (d, 6H, 2Me from i-Pr); 2.80 (s, 3H, 6-Me); 2.90 (s, 3H, 4-Me); 3.49 (heptet, 1H, CH from i-Pr); 7.25-8.43 (m, AA'BB', 4H, ArH from 1,4-phenylene); 7.98 (s, 2H, ArH, 3,5-H from pyridinium). Anal $C_{18}H_{22}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-di-iso-propyl-4-methylpyridinium perchlorate 73, tan crystals, mp 278-9° C.; IR (KBr), cm$^{-1}$: 625, 685, 820, 1100, 1165, 1340, 1635, 3030, 3250; $^1$H-NMR (TFA), δ, ppm: 1.51 (d, 12H, 4Me from 2 i-Pr); 2.83 (s, 3H, 4-Me); 3.42 (heptet, 2H, 2CH from 2 i-Pr); 7.31-8.51 (m, AA'BB', 4H, ArH from 1,4-phenylene); 8.05 (s, 2H, ArH, 3,5-H from pyridinium). Anal $C_{20}H_{26}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-dimethyl-4-phenylpyridinium perchlorate 75, white crystals, mp >300° C.; IR (KBr), cm$^{-1}$: 625, 690, 770, 1100, 1170, 1330, 1635, 3030, 3260, 3330; $^1$H-NMR (TFA), δ, ppm: 2.62 (s, 6H, 2,6-(Me)$_2$); 8.10-9.12 (m, H, ArH from 1,4-phenylene, pyridinium and 4-Ph). Anal $C_{21}H_{20}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-diethyl-4-phenylpyridinium perchlorate 76, tan crystals, mp 267-8° C.; IR (KBr), cm$^{-1}$: 625, 695, 765, 1100, 1180, 1340, 1630, 3040, 3270, 3360; $^1$H-NMR (TFA), δ, ppm: 1.43 (t, 6H, 2 Me from ethyl); 2.82 (q, 4H, 2 CH$_2$ from Et); 7.68-8.87 (m, 11H, ArH from 1,4-phenylene, pyridinium and 4-Ph). Anal $C_{23}H_{24}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-di-n-propyl-4-phenylpyridinium perchlorate 77, colorless crystals, mp 235-7° C.; IR (KBr), cm$^{-1}$: 625, 695, 770, 1100, 1180, 1340, 1630, 3050, 3220, 3315; $^1$H-NMR (TFA), δ, ppm: 1.06 (t, 6H, 2 Me from propyl); 1.73 (sextet, 4H, 2CH$_2$ (β) from n-Pr); 2.84 (t, 4H, 2 CH$_2$ (α) from n-Pr); 7.55-8.71 (m, 11H, ArH from 1,4-phenylene, pyridinium and 4-Ph). Anal $C_{25}H_{28}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-di-isopropyl-4-phenylpyridinium perchlorate 79, white crystals, mp 278-9° C.; IR (KBr), cm$^{-1}$: 625, 690, 765, 1100, 1180, 1340, 1625, 3040, 3270, 3315; $^1$H-NMR (TFA), δ, ppm: 1.45 (d, 12H, 4 Me from i-Pr); 2.95 (heptet, 2H, 2 CH from i-Pr); 7.92-8.97 (m, 11H, ArH from 1,4-phenylene, pyridinium and 4-Ph). Anal $C_{25}H_{28}N_5O_4S_3{}^+ClO_4{}^-$ (C, H, N).

1-N-[5-Sulfamoyl-1,3,4-thiadiazol-2-yl-(aminosulfonyl-4-phenyl)]-2-methyl-4,6-diphenylpyridinium perchlorate 80, white crystals, mp 298-99° C.; IR (KBr), cm$^{-1}$: 625, 710, 770, 1100, 1170, 1345, 1625, 3040, 3245, 3350; $^1$H-NMR (TFA), δ, ppm: 2.75 (s, 3H, 2-Me); 7.53-8.70 (m, 16H, ArH from 1,4-phenylene, pyridinium and 4,6-Ph$_2$). Anal $C_{26}H_{22}N_5O_4S_3{}^+ClO_4{}^-$ (C, H, N).

1-N-[5-Sulfamoyl-1,3,4-thiadiazol-2-yl-(aminosulfonyl-4-phenyl)]-2-ethyl-4,6-diphenylpyridinium perchlorate 81, white crystals, mp 254-5° C.; IR (KBr), cm$^{-1}$: 625, 700, 770, 1100, 1180, 1340, 1620, 3040, 3250, 3350; $^1$H-NMR (TFA), δ, ppm: 1.52 (t, 3H, Me from ethyl); 2.97 (q, 2H, CH$_2$); 7.40-8.57 (m, 16H, ArH from 1,4-phenylene, pyridinium and 4,6-Ph$_2$). Anal $C_{27}H_{24}N_5O_4S_3{}^+ClO_4{}^-$ (C, H, N).

1-N-[5-Sulfamoyl-1,3,4-thiadiazol-2-yl-(aminosulfonyl-4-phenyl)]-2-n-propyl-4,6-diphenylpyridinium perchlorate 82, white crystals, mp 214-5° C.; IR (KBr), cm$^{-1}$: 625, 700, 770, 1100, 1180, 1340, 1620, 3030, 3270, 3350; $^1$H-NMR (TFA), δ, ppm: 1.03 (t, 3H, Me from propyl); 1.95 (sextet, 2H, β-CH$_2$ from n-Pr); 2.88 (t, 2H, α-CH$_2$ from n-Pr); 7.39-8.55 (m, 16H, ArH from 1,4-phenylene, pyridinium and 4,6-Ph$_2$). Anal $C_{28}H_{26}N_5O_4S_3{}^+ClO_4{}^-$ (C, H, N).

1-N-[5-Sulfamoyl-1,3,4-thiadiazol-2-yl-(aminosulfonyl-4-phenyl)]-2-iso-propyl-4,6-diphenylpyridinium perchlorate 83, white crystals, mp 186-8° C.; IR (KBr), cm$^{-1}$: 625, 700, 770, 1100, 1170, 1340, 1620, 3040, 3250, 3360; $^1$H-NMR (TFA), δ, ppm: 1.51 (d, 6H, 2 Me from i-propyl); 2.50-3.27 (m, 1H, CH from i-Pr); 7.32-8.54 (m, 16H, ArH from 1,4-phenylene, pyridinium and 4,6-Ph$_2$). Anal $C_{28}H_{26}N_5O_4S_3{}^+ClO_4{}^-$ (C, H, N).

1-N-[5-Sulfamoyl-1,3,4-thiadiazol-2-yl-(aminosulfonyl-4-phenyl)]-2-n-butyl-4,6-diphenylpyridinium perchlorate 84, white crystals, mp 241-3° C.; IR (KBr), cm$^{-1}$: 625, 710, 770, 1100, 1180, 1335, 1625, 3040, 3260, 3345; $^1$H-NMR (TFA), δ, ppm: 0.93 (t, 3H, Me from butyl); 1.12-2.14 (m, 4H, CH$_3$—CH$_2$—CH$_2$—CH$_2$ from n-Bu); 2.96 (t, 2H, α-CH$_2$ from n-Bu); 7.21-8.50 (m, 16H, ArH from 1,4-phenylene, pyridinium and 4,6-Ph$_2$). Anal $C_{29}H_{28}N_5O_4S_3{}^+ClO_4{}^-$ (C, H, N).

1-N-[5-Sulfamoyl-1,3,4-thiadiazol-2-yl-(aminosulfonyl-4-phenyl)]-2-tert-butyl-4,6-diphenylpyridinium perchlorate 85, white crystals, mp 203-5° C.; IR (KBr), cm$^{-1}$: 625, 705, 765, 1100, 1160, 1310, 1620, 3060, 3270; $^1$H-NMR (TFA), δ, ppm: 1.91 (s, 9H, t-Bu); 6.80-8.74 (m, 16H, ArH from 1,4-phenylene, 4,6-Ph$_2$ and 3,5-H from pyridinium). Anal $C_{29}H_{28}N_5O_4S_3{}^+ClO_4{}^-$ (C, H, N).

1-N-[5-Sulfamoyl-1,3,4-thiadiazol-2-yl-(aminosulfonyl-4-phenyl)]-2,4,6-triphenhyl-pyridinium perchlorate 87: pale yellow crystals, mp >300° C.; IR (KBr), cm$^{-1}$ (bands in italics are due to the anion): 625, 635, 703, 785, 896, 1100, 1150, 1204, 1355, 1410, 1520, 1600, 3065; $^1$H-NMR (D$_2$O), δ, ppm: 7.50-8.60 (m, 19H, ArH, 3Ph+C$_6$H$_4$); 9.27 (s, 2H, ArH, 3,5-H from pyridinium); in this solvent the sulfonamido protons are not seen, being in fast exchange with the solvent. Anal $C_{31}H_{24}N_5O_4S_3{}^+ClO_4{}^-$ (C, H, N).

1-N-[5-Sulfamoyl-1,3,4-thiadiazol-2-yl-(aminosulfonyl-4-phenyl)]-2,6-diphenylpyridinium perchlorate 88, yellow crystals, mp 218-20° C.; IR (KBr), cm$^{-1}$: 625, 705, 765, 1100, 1160, 1335, 1615, 3050, 3260; $^1$H-NMR (TFA), δ, ppm: 6.75-8.43 (m, 17H, ArH from 1,4-phenylene, 2,6-Ph$_2$ and 3,4,5-H from pyridinium). Anal $C_{25}H_{20}N_5O_4S_3{}^+ClO_4{}^-$ (C, H, N).

1-N-[5-Sulfamoyl-1,3,4-thiadiazol-2-yl-(aminosulfonyl-4-phenyl)]-2,3,4,6-tetramethylpyridinium perchlorate 89, tan crystals, mp >300° C.; IR (KBr), cm$^{-1}$: 625, 800, 1100, 1165, 1330, 1630, 3030, 3305; $^1$H-NMR (TFA), δ, ppm: 2.62 (s, 3H, 4-Me); 2.74 (s, 3H, 3-Me); 2.88 (s, 6H, 2,6-(Me)$_2$); 7.21-8.50 (m, AA'BB', 4H, ArH from 1,4-phenylene); 7.93 (s, 1H, ArH, 5-H from pyridinium). Anal $C_{17}H_{20}N_5O_4S_3{}^+ClO_4{}^-$ (C, H, N).

Example 4

Ectopic Expression of CA IX Leads to Increased Acidification of Extracellular pH in Hypoxia Expression of CA IX in tumor cells is induced by hypoxia simultaneously with various components of anaerobic metabolism and acid extrusion pathways. Such simultaneous induction complicates the determination of the contribution of CA IX to the overall change in pHe. Therefore, the inventors used MDCK immortalized canine kidney epithelial cells that do not express endogenous CA IX, but were stably transfected to express the human CA IX protein in a constitutive manner. Levels of CA IX in MDCK-CA IX transfectants were comparable between the hypoxic cells maintained for 48 hours in 2% $O_2$ and the normoxic cells incubated in 21% $O_2$ (data not shown). Immunofluorescence analysis indicated that CA IX was predominantly localized at the cell surface, although the membrane staining in hypoxic cells was less pronounced due to hypoxia-induced perturbation of intercellular contacts [103]. Hypoxic incubation led to the expected extracellular acidification in the CA IX-positive as well as CA IX-negative cell cultures when compared to their normoxic counterparts (FIG. 7A). However, upon mutual comparison of the hypoxic cells it was evident that pHe was significantly decreased in the cells containing CA IX. Taking into account a steady, hypoxia-independent level of CA IX in MDCK-CA IX cells, that finding indicated that hypoxia activated the catalytic performance of CA IX, which resulted in enhanced pHe acidification.

To exclude the possibility that hypoxia-induced acidification was caused by an increased production of lactic acid, the inventors determined the corresponding lactate concentrations in the media from both CA IX-negative and CA IX-positive transfectants (FIG. 7B). In accord with the literature, production of lactic acid was significantly higher in the cells maintained in hypoxia than in the normoxic cells. However, there were practically no differences between the lactate production in cultures of CA IX-positive and CA IX-negative cells, suggesting that the excessive pHe decrease observed in hypoxia could be explained by the activation of CA IX.

Example 5

Sulfonamides Inhibit CA IX-Mediated Acidification of pHe and Bind to Hypoxic MDCK-CA IX Cells The three representative CA IX-selective inhibitors shown in FIG. 8A were tested in accordance with the concepts of the subject invention. Compound 6 is a strong inhibitor of CA IX, whereas it is less efficient against the widely distributed cytoplasmic CA II and the plasma membrane-anchored CA IV [114], Compound 39 is practically membrane-impermeable [81] and Compound 92 [FITC derivative of homosulfanilamide (Compound 5)] has a big moiety favoring its interaction with the CA IX active site, which is assumed to form a larger cavity than in CA II [135]. All three sulfonamides were able to reduce the extracellular acidification of MDCK-CA IX cells in hypoxia and their effect on the normoxic pHe was negligible (FIG. 8B). Moreover, in fluorescence analysis (treated MDCK-CA IX cells incubated in normoxia or hypoxia for 48 hours), FITC-labeled Compound 92 was detected only in hypoxic MDCK-CA IX cells, but was absent from their normoxic counterparts and from the mock-transfected controls (data not shown). Cytoplasmic accumulation of Compound 92 was possibly related to a hypoxia-induced internalization of CA IX described earlier [103]. Lack of the fluorescence signal in CA IX-negative MDCK cells confirmed the selectivity of the inhibitor, which did not bind to other potentially present CA isoforms and indicated that only the hypoxic MDCK-CA IX cells contain the catalytically active CA IX with the enzyme center accessible to inhibitor.

Example 6

Intact CA IX Catalytic Domain is Required for the Extracellular Acidification in Hypoxia In addition to the enzyme domain (CA), the extracellular part of CA IX contains an N-terminal proteoglycan-related region (PG) that is absent from the other CAs and seems implicated in cell adhesion [146]. To examine involvement of those CA IX domains in pHe control, the inventors produced deletion variants of CA IX, in which either the PG region (ΔPG) or a large portion of the CA domain (ΔCA) was removed [FIG. 9A]. Immunofluorescence analysis using two MAbs, namely the PG-specific M75 for ΔCA and CA-specific V/10 for ΔPG, has shown that both deleted proteins were transported to the plasma membrane (data not shown). The mutants were expressed at levels comparable with the wild-type CA IX, as analyzed by immunoblotting of ΔCA and ΔPG proteins under both reducing and non-reducing conditions for their molecular weight and a capacity to form oligomers (data not shown). Interestingly, ΔCA was unable to form oligomers possibly due to the absence of two out of four cysteines (C174 and C336) required for the proper S—S bonding. As judged from the molecular weights, ΔPG mutant appeared to assemble into dimeric and tetrameric complexes, rather then into trimers.

Elimination of a large part of the CA domain perturbed the acidification capacity of CA IX, whereas removal of the PG region had no such effect (FIG. 9B). That differential behavior could be reasonably assigned to the absence versus presence of the catalytic activity of CA IX, because the cells expressing these variants produced similar levels of lactic acid (FIG. 9B). It also indicates that the CA domain is both necessary and sufficient for the enzyme activity, and that the PG and CA portions of CA IX can be functionally separated, although they may still cooperate in response to diverse physiological factors. Based on the knowledge that the extracellular acidosis interferes with the cell adhesion, the enzyme activity carried out by the CA domain might influence the adhesion-related properties of PG region and vice versa. Indeed, CA IX was shown to destabilize E cadherin-mediated intercellular adhesion in transfected MDCK cells, which was particularly dramatic in the hypoxic monolayer [103] in conditions accompanied by CA IX-mediated extracellular acidosis described herein.

Example 7

FITC-Labeled Compound 92 Sulfonamide Binds to and Increases pHe of Hypoxic Tumor Cells To see whether the phenomenon of CA IX-mediated acidification is applicable to tumor cells with endogenous CA IX, the effect of FITC-labeled Compound 92 sulfonamide [FITC derivative of homosulfanilamide, Compound 5] on the pHe of the cervical carcinoma cells HeLa and SiHa, respectively, was examined. Under hypoxia, tumor cells coordinately express elevated levels of multiple HIF-1 targets, including CA IX [139]. In addition, activity of many components of the hypoxic pathway and related pH control mechanisms, such as ion transport across the plasma membrane, are abnormally increased in order to maintain the neutral intracellular pH [86]. This explains the considerably decreased pHe of the hypoxic versus normoxic HeLa and SiHa cells (FIG. 10). The acidosis was partially reduced by Compound 92 inhibitor, in support of the idea that activation of CA IX is just one of many consequences of hypoxia. Moreover, FITC-labeled Compound 92 accumulated in the hypoxic HeLa and SiHa cells that contained elevated levels of CA IX, but not in the normoxic cells with a diminished CA IX expression. [HeLa and SiHa cells plated on coverslips were treated with FITC-labeled Compound 92 sulfonamide during 48 hour incubation in normoxia and hypoxia, washed with PBS and inspected under the fluorescence microscope (data not shown). CA IX expression levels were measured by immunoblotting analysis with M75 MAb.] As indicated by CA IX's ability to bind Compound 92 and mediate its accumulation in hypoxia, CA IX expressed in the hypoxic tumor cells was catalytically active.

Example 8

Expression of ΔCA Mutant in HeLa Cells Reduces pHe Acidification in Hypoxia

Based on the assumption that the enzyme-dead ΔCA mutant could abolish the function of the endogenous CA IX, the inventors generated HeLa-ΔCA transfectants. As determined by immunofluorescence and immunoblotting analysis (using V/10 MAb to detect endogenous CA IX protein or M75 MAb to visualize both CA IX and ΔCA mutant), the HeLa-ΔCA cells contained ΔCA but not CA IX under normoxia, expressed both proteins under hypoxia, and under non-reducing conditions exhibited an atypical band presumably corresponding to mixed oligomers composed of both CA IX and ΔCA (data not shown). No significant differences in pHe were observed between the normoxic HeLa-mock and HeLa-ΔCA cells. On the other hand, HeLa-ΔCA transfectants treated by hypoxia produced less acidic medium than the control HeLa-mock cells (FIG. 11), suggesting that the inactive ΔCA deletion variant interfered with the activity of the wild-type protein, and further supporting the role of CA IX. Altogether, the data strongly implies that the acidification of the extracellular pH in hypoxic tumor cells does involve CA activity, and that CA IX directly participates in the phenomenon.

DISCUSSION

In the context of the experimental results described herein that place CA IX among the direct contributors to the hypoxic microenvironment, it is tempting to propose possible means of CA IX's action. MN/CA IX is considered to participate in this phenomenon by catalyzing hydration of carbon dioxide to generate bicarbonate ions that are then transported into cell interior and protons that acidify extracellular pH. There are some indications given by the data obtained with the physiologically relevant CA isoforms II and IV that physically interact with anion exchangers (AE) to form a metabolon that facilitates bicarbonate transport in differentiated cells [140, 141]. It seems plausible that CA IX could work as an extracellular component of the similar metabolon in tumor cells. Assembly and/or activation of such metabolon would be especially meaningful in low oxygen conditions, because a highly efficient transport of bicarbonate is required particularly in hypoxic cells for the buffering of intracellular pH and biosynthetic reactions. According to such a model, enhanced conversion of $CO_2$ to bicarbonate by the hypoxia-activated CA IX would be coupled with the increased production of extracellular protons contributing to acidosis. Data obtained as disclosed herein fit well with such a proposal. Further supportive hints come from the studies of von Hippel-Lindau tumor suppressor protein (pVHL), the main negative regulator of HIF-1, which can down-regulate CA IX (obviously as a direct HIF-1 target) and can also reduce the transport activity of AEs [128, 131].

Downstream effects of CA IX can be at least partially anticipated on the basis of the known connections between the acidic pHe and certain features of the tumor phenotype [86, 124, 125, 126, 130, 132]. Moreover, as a part of the hypoxic acidification machinery, CA IX might facilitate a nucleolar sequestration of pVHL and activation of HIF, which is a recently described pH-dependent mechanism proposed to serve a protective role in reoxygenated cells [Mekhail et al., 2004]. In such case, HIF-mediated increase in the level and activity of CA IX resulting in enhanced acidification might create a feedback loop leading to a prolonged HIF activation, which is certainly an attractive possibility requiring experimental proof.

In conclusion, the instant disclosure provides the first direct evidence for the role of CA IX in acidification of the extracellular pH. The findings of the inventors significantly improve the view of CA IX as a molecule, whose levels and catalytic activity are regulated by the oxygen availability, and open new possibilities for its better understanding and clinical exploitation. Inhibition of the MN/CA IX catalytic activity resulting in reduced extracellular acidification may have direct anticancer effects or may modulate efficiency of those conventional chemotherapeutic drugs whose uptake is pH-dependent.

Budapest Treaty Deposits

The hybridoma VU-M75 was deposited on Sep. 17, 1992 with the American Type Culture Collection (ATCC) now at 10810 University Blvd., Manassus, Va. 20110-2209 (USA) and assigned Accession No. HB 11128. The deposit was made under the provisions of the Budapest Treaty on the International Recognition of Deposited Microorganisms for the Purposes of Patent Procedure and Regulations thereunder (Budapest Treaty). Maintenance of a viable culture is assured for thirty years from the date of deposit. The hybridoma will be made available by the ATCC under the terms of the Budapest Treaty, and subject to an agreement between the Applicants and the ATCC which assures unrestricted availability of the deposited hybridoma to the public upon the granting of a patent from the instant application. Availability of the deposited strain is not to be construed as a license to practice the invention in contravention of the rights granted under the authority of any Government in accordance with its patent laws.

Similarly, the hybridoma cell line V/10-VU which produces the V/10 monoclonal antibodies was deposited on Feb. 19, 2003 under the Budapest Treaty at the International Depository Authority (IDA) of the Belgian Coordinated Collections of Microorganisms (BCCM) at the Laboratorium voor Moleculaire Biologie-Plasmidencollectie (LMBP) at the Universeit Gent, K.L. Ledeganckstraat 35, is B-9000 Gent, Belgium [BCCM/LMBP] under the Accession No. LMBP 6009CB.

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method of selectively imaging activated MN/CA IX expressed in hypoxic tissues in a patient, comprising:
   a) administering to said patient a specific inhibitor of activated MN/CA IX, wherein said specific inhibitor of activated MN/CA IX is an MN/CA IX-specific antibody that binds the activated form of MN/CA IX's CA domain and not the inactive form of MN/CA IX's CA domain, and said antibody is linked to an imaging agent; and
   b) if activated MN/CA IX is present in said hypoxic tissues, detecting the binding of said MN/CA IX-specific antibody, wherein binding of said MN/CA IX-specific antibody indicates the presence of activated MN/CA IX in said tissues.

2. A diagnostic/prognostic method for a preneoplastic/neoplastic disease associated with abnormal MN/CA IX expression, comprising determining whether MN/CA IX is activated in a vertebrate sample, comprising:
   a) contacting said sample with a specific inhibitor of the activated form of MN/CA IX's CA domain, wherein said specific inhibitor of the activated form of MN/CA IX's CA domain is an MN/CA IX-specific antibody that binds the activated form of MN/CA IX's CA domain and not the inactive form of MN/CA IX's CA domain, and
   b) detecting or detecting and quantifying binding of said specific inhibitor of the activated form of MN/CA IX's CA domain in said sample;
   wherein binding of said inhibitor to MN/CA IX indicates that said bound MN/CA IX in said sample is activated.

3. The method of claim 2 wherein said activated MN/CA IX is hypoxia-activated.

4. The method of claim 2, wherein said MN/CA IX-specific antibody, that is a specific inhibitor of the activated form of MN/CA IX's CA domain, is conjugated to a label or a visualizing means, wherein said detecting or detecting and quantifying binding comprises detecting or detecting and quantifying said label or said visualizing means on cells in said sample, and wherein said detecting or said detecting and quantifying at a level above that for a control sample is indicative of hypoxic precancerous or cancerous cells that abnormally express activated MN/CA IX in said sample.

5. The method of claim 4, wherein said label is fluorescein isothiocyanate.

6. The method of claim 4, further comprising detecting the binding of a second antibody that specifically binds to a MN/CA IX domain other than the carbonic anhydrase domain.

7. The method of claim 4, wherein said method is used as an aid in selection of patient therapy.

8. The method of claim 7, wherein said binding to activated MN/CA IX is detectable at a level above that for a control sample, and said method is used in the decision to use hypoxia-selective therapy.

9. The method of claim 8, wherein said hypoxia-selective therapy comprises the use of drugs that are toxic only under hypoxic conditions.

10. The method of claim 9, wherein said hypoxia-selective therapy comprises the use of tirapazamine or AQ4N.

11. The method of claim 7, wherein said binding to activated MN/CA IX is not detectable at a level above that for a control sample, and said method is used in the decision to use radiotherapy or non-hypoxia-selective chemotherapy.

12. A method that is diagnostic, or diagnostic and prognostic for precancer or cancer associated with overexpression of activated MN/CA IX comprising contacting a mammalian sample with a specific inhibitor of activated MN/CA IX, wherein said specific inhibitor of activated MN/CA IX is an MN/CA IX-specific antibody that specifically binds to the activated form of MN/CA IX's CA domain and does not bind the inactive form of MN/CA IX'S CA domain, said antibody conjugated to a label or a visualizing means, and detecting, or detecting and quantifying binding of said MN/CA IX-specific antibody to cells in said sample by detecting, or detecting and quantifying said label or said visualizing means on cells in said sample, wherein said detection, or said detection and quantitation at a level above that for a control sample is indicative of precancerous or cancerous cells that overexpress activated MN/CA IX in said sample.

13. The method of claim 12 wherein MN/CA IX activated by hypoxic conditions is detected, or detected and quantitated, and the mammal from whom the sample was taken is considered to have a poor prognosis, and decisions on treatment for said mammal are made in view of the presence of said hypoxic conditions.

* * * * *